(12) United States Patent
Cheriton

(10) Patent No.: US 11,630,679 B2
(45) Date of Patent: Apr. 18, 2023

(54) USING A LANE-STRUCTURED DYNAMIC ENVIRONMENT FOR RULE-BASED AUTOMATED CONTROL

(71) Applicant: OptumSoft, Inc., Menlo Park, CA (US)

(72) Inventor: David R. Cheriton, Palo Alto, CA (US)

(73) Assignee: OptumSoft, Inc., Vero Beach, FL (US)

( * ) Notice: Subject to any disclaimer, the term of this patent is extended or adjusted under 35 U.S.C. 154(b) by 385 days.

(21) Appl. No.: 16/795,236

(22) Filed: Feb. 19, 2020

(65) Prior Publication Data

US 2020/0264900 A1    Aug. 20, 2020

Related U.S. Application Data

(60) Provisional application No. 62/807,694, filed on Feb. 19, 2019.

(51) Int. Cl.
| | | |
|---|---|---|
| *G06F 9/44* | (2018.01) | |
| *G06F 9/448* | (2018.01) | |
| *B60W 30/18* | (2012.01) | |
| *G16H 50/20* | (2018.01) | |
| *G06Q 40/04* | (2012.01) | |
| *G06F 9/46* | (2006.01) | |
| *G06F 9/50* | (2006.01) | |

(52) U.S. Cl.
CPC ..... *G06F 9/4494* (2018.02); *B60W 30/18163* (2013.01); *G06F 9/46* (2013.01); *G06F 9/5038* (2013.01); *G06Q 40/04* (2013.01); *G16H 50/20* (2018.01)

(58) Field of Classification Search
CPC ..................................................... G06F 9/4494
USPC ........................................................... 718/100
See application file for complete search history.

(56) References Cited

U.S. PATENT DOCUMENTS

| | | | |
|---|---|---|---|
| 4,754,410 A | 6/1988 | Leech | |
| 10,671,076 B1 * | 6/2020 | Kobilarov | ............. G08G 1/166 |
| 2016/0070260 A1 | 3/2016 | Levien | |
| 2016/0231746 A1 * | 8/2016 | Hazelton | ............. G05D 1/0274 |
| 2019/0041819 A1 * | 2/2019 | Frazer | ................. G05B 13/021 |
| 2020/0247412 A1 * | 8/2020 | Wang | .................... G02B 27/01 |
| 2020/0276988 A1 * | 9/2020 | Graves | .................. G06N 3/006 |

* cited by examiner

*Primary Examiner* — Timothy A Mudrick
(74) *Attorney, Agent, or Firm* — Van Pelt, Yi & James LLP

(57) ABSTRACT

Specifications are input, comprising: a plurality of lanes in an environment for a controlled system; a plurality of lane maneuvers associated with the plurality of lanes; a plurality of lane subconditions associated with the controlled system; and a rule set comprising a plurality of rules, wherein a rule in the rule set specifies a rule condition and a rule action to take when the rule condition is satisfied, wherein the rule condition comprises a corresponding set of lane subconditions, and wherein the rule action comprises a corresponding lane maneuver. The controlled system is automatically navigated dynamically, at least in part by: monitoring the plurality of lane subconditions; evaluating rule conditions associated with the plurality of rules in the rule set to determine one or more rules whose corresponding rule conditions has been met; and executing one or more lane maneuvers that correspond to the one or more determined rules.

18 Claims, 21 Drawing Sheets

64-bit known/value block representation

```
602 ─┐
     └─ UniLink : Element {
            connectsTo : Interface::Ptr;
            lossOfSignal : Subcondition {
                → connectsTo:::lossOfSignalIn;
            }
604 ─┐  }
     └─ Link : Element {
            component : UniLink[2];
            cableBroken : Subcondition {
                `actionLabel =
        "reportCableBreak";
                → component::lossOfSignal;
            }
        }
606 ─┐ }
     └─ Interface {
            lossOfSignalIn : Subcondition {
                → parent::lossOfSignalIn$;
            }
            connectedToBy : Interface {
                `inverse = UniLink::connectsTo;
            }
608 ─┐  }
     └─ Switch : Element {
            component: Interface[X];
            lossOfSignalIn$ :: Subcondition {
                `observedBy = (signalIn==0);
            }
        }
```

FIG. 6

USING A LANE-STRUCTURED DYNAMIC ENVIRONMENT FOR RULE-BASED AUTOMATED CONTROL

CROSS REFERENCE TO OTHER APPLICATIONS

This application claims priority to U.S. Provisional Patent Application No. 62/807,694 entitled USING A LANE-STRUCTURED DYNAMIC ENVIRONMENT FOR RULE-BASED AUTOMATED CONTROL filed Feb. 19, 2019 which is incorporated herein by reference for all purposes.

BACKGROUND OF THE INVENTION

Automatically navigating a controlled system dynamically may provide many benefits such as reducing labor expense, enhancing human safety, and improving resource efficiency of the controlled system. Examples of controlled systems include those that control behavior of a self-driving physical vehicle, an automatic stock trading platform, or an automatic medical diagnosis and treatment application.

A dynamic environment such as a vehicular roadway, a stock market, and a medical patient presents an immense set of complexities for automatic navigation. Currently it is challenging to design an automatic navigator that can effectively wrestle with these complexities. These complexities cause problems because of the high cost of computing resources such as processing power, memory, storage, and network resources, and/or slow response in terms of latency and/or throughput.

BRIEF DESCRIPTION OF THE DRAWINGS

Various embodiments of the invention are disclosed in the following detailed description and the accompanying drawings.

FIG. 6 is an illustration of an embodiment of a simple model of a computer network.

DETAILED DESCRIPTION

Figure 1:
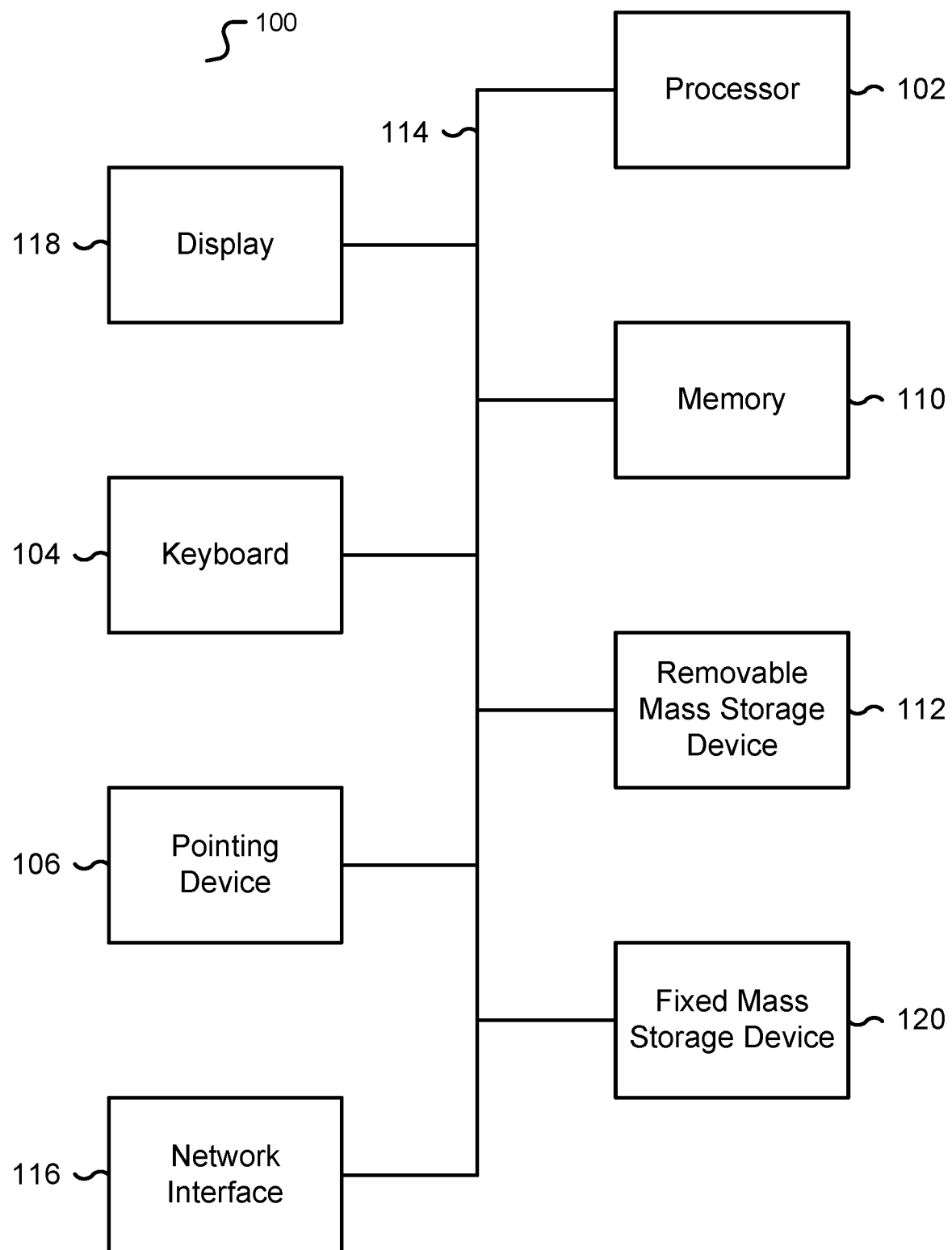
FIG. 1 is a functional diagram illustrating a programmed computer/server system for approximate matching in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Using a lane-structured dynamic environment for rule-based automated control is disclosed. Traditionally rule-based systems may be thought of as suitable for dynamic environments, for example using motion planning for self-driving vehicles, but motion planning contains a plurality of expensive operations to handle the complexity of self-driving. These expensive operations may degrade safety because of the expense in latency or reaction, degrade efficiency of a route navigation because of the expense of speed, or increase navigation power/energy requirements because of the expense in processing power, memory, storage, and/or network resources.

Using a concept of a "lane" to simplify the dynamic environment is disclosed. As referred to herein, a lane is a discretized directional path segment that the controlled system can transit through under certain conditions through an N-dimensional space while complying with non-dynamic constraints. An example of a lane is a lane in a road, but as described below there are other environments where the abstraction of a lane works including the stock market environment as described below and a medical application environment as described below. Thus, using lanes to impose structure on a dynamic environment such that a rule-based system may effectively automatically navigate a controlled system through the environment is disclosed. Throughout this specification, the examples of a self-driving vehicle, stock trading, and/or medical domain/applications may be given for illustrative purposes, but the principles, techniques, and systems described herein may be generalized to other applications without limitation.

FIG. 1 is a functional diagram illustrating a programmed computer/server system for approximate matching in accordance with some embodiments. As shown, FIG. 1 provides a functional diagram of a general purpose computer system programmed for automatically navigating a controlled system dynamically in accordance with some embodiments. As will be apparent, other computer system architectures and configurations may be used for automatic navigation.

Computer system 100, which includes various subsystems as described below, includes at least one microprocessor subsystem, also referred to as a processor or a central processing unit ("CPU") (102). For example, processor (102) can be implemented by a single-chip processor or by multiple cores and/or processors. In some embodiments, processor (102) is a general purpose digital processor that controls the operation of the computer system 100. Using instructions retrieved from memory (110), the processor (102) controls the reception and manipulation of input data, and the output and display of data on output devices, for example display and graphics processing unit (GPU) (118).

Processor (102) is coupled bi-directionally with memory (110), which can include a first primary storage, typically a random-access memory ("RAM"), and a second primary storage area, typically a read-only memory ("ROM"). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor (102). Also as is well known in the art, primary storage typically includes basic operating instructions, program code, data, and objects used by the processor (102) to perform its functions, for example programmed instructions. For example, primary storage devices (110) can include any suitable computer-readable storage media, described below, depending on whether, for example, data access needs to be bi-directional or uni-directional. For example, processor (102) can also directly and very rapidly retrieve and store frequently needed data in a cache memory, not shown. The processor (102) may also include a coprocessor (not shown) as a supplemental processing component to aid the processor and/or memory (110).

A removable mass storage device (112) provides additional data storage capacity for the computer system 100, and is coupled either bi-directionally (read/write) or uni-directionally (read only) to processor (102). For example, storage (112) can also include computer-readable media such as flash memory, portable mass storage devices, holographic storage devices, magnetic devices, magneto-optical devices, optical devices, and other storage devices. A fixed mass storage (120) can also, for example, provide additional data storage capacity. One example of mass storage (120) is an eMMC or microSD device. In one embodiment, mass storage (120) is a solid-state drive connected by a bus (114). Mass storages (112), (120) generally store additional programming instructions, data, and the like that typically are not in active use by the processor (102). It will be appreciated that the information retained within mass storages (112), (120) can be incorporated, if needed, in standard fashion as part of primary storage (110), for example RAM, as virtual memory.

In addition to providing processor (102) access to storage subsystems, bus (114) can be used to provide access to other subsystems and devices as well. As shown, these can include a display monitor (118), a communication interface (116), a touch (or physical) keyboard (104), and one or more auxiliary input/output devices (106) including an audio interface, a sound card, microphone, audio port, audio recording device, audio card, speakers, a touch (or pointing) device, and/or other subsystems as needed. Besides a touch screen and/or capacitive touch interface, the auxiliary device (106) can be a mouse, stylus, track ball, or tablet, and is useful for interacting with a graphical user interface.

The communication interface (116) allows processor (102) to be coupled to another computer, computer network, or telecommunications network using a network connection as shown. For example, through the communication interface (116), the processor (102) can receive information, for example data objects or program instructions, from another network, or output information to another network in the course of performing method/process steps. Information, often represented as a sequence of instructions to be executed on a processor, can be received from and outputted to another network. An interface card or similar device and appropriate software implemented by, for example executed/performed on, processor (102) can be used to connect the computer system 100 to an external network and transfer data according to standard protocols. For example, various process embodiments disclosed herein can be executed on processor (102), or can be performed across a network such as the Internet, intranet networks, or local area networks, in conjunction with a remote processor that shares a portion of the processing. Throughout this specification "network" refers to any interconnection between computer components including the Internet, Bluetooth, WiFi, 3G, 4G, 4GLTE, GSM, Ethernet, TCP/IP, intranet, local-area network ("LAN"), home-area network ("HAN"), serial connection, parallel connection, wide-area network ("WAN"), Fibre Channel, PCI/PCI-X, AGP, VLbus, PCI Express, Expresscard, Infiniband, ACCESS.bus, Wireless LAN, HomePNA, Optical Fibre, G.hn, infrared network, satellite network, microwave network, cellular network, virtual private network ("VPN"), Universal Serial Bus ("USB"), FireWire, Serial ATA, 1-Wire, UNI/O, or any form of connecting homogenous, heterogeneous systems and/or groups of systems together. Additional mass storage devices, not shown, can also be connected to processor (102) through communication interface (116).

An auxiliary I/O device interface, not shown, can be used in conjunction with computer system 100. The auxiliary I/O device interface can include general and customized interfaces that allow the processor (102) to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: flash media such as NAND flash, eMMC, SD, compact flash; magnetic media such as hard disks, floppy disks, and magnetic tape; optical media such as CD-ROM disks; magneto-optical media such as optical disks; and specially configured hardware devices such as application-specific integrated circuits ("ASIC"s), programmable logic devices ("PLD"s), and ROM and RAM devices. Examples of program code include both machine code, as produced, for example, by a compiler, or files containing higher level code, for example, a script that can be executed using an interpreter.

The computer/server system shown in FIG. 1 is but an example of a computer system suitable for use with the various embodiments disclosed herein. Other computer systems suitable for such use can include additional or fewer subsystems. In addition, bus (114) is illustrative of any interconnection scheme serving to link the subsystems. Other computer architectures having different configurations of subsystems may also be utilized.

A rule-based system is an intuitively appealing approach for structuring an automated control system because normal manual approach to control is often specified in terms of rules. For example, within the application domain of self-driving cars, manual driving is governed by rules including the rules of the road and the rules of safe driving. Similarly, in an automatic stock trading system, there are rules associated with trading, both imposed by the market platform itself as well as the financial institution running the trading applications. Similarly, medical treatments for diseases or disorders generally follow a prescribed set of rules, for example, a patient should not be prescribed to take medicine X if already taking medicine Y.

When applying a rule-based system ("RBS") to automation control, a first issue to address is that the rules for manual/human operation are often stated in terms of constraints, rather than the condition:action formulation used in an automated RBS. For example, a standard driving rule is: Do not exceed the speed limit. This rule does not indicate the speed at which the vehicle should be traveling, but leaves it to the judgment of the human driver. This example is a constraint in the sense that it states that the speed of the vehicle is always less than or equal to the speed limit. A constraint is referred to herein as a statement and/or condition that the system should work to make true. With an automated system, rules need to provide this judgment. That is, there needs to be rules in a condition:action format that cause the system to respond to conditions of rules becoming true to trigger actions that achieve this constraint.

In a simple formulation, a basic rule may easily be formulated as:

```
if( speed > speedLimit ) {
    slowdown( );
}
```

However, in reality, the conditions for slowing down are much more complex, including the potential presence of a dynamic obstacle that suddenly appears in the direction the vehicle is headed, a traffic light ahead, entering a relative sharp turn, and so on. The realistic condition for when a vehicle should slow down may be quite complex and hard to get right.

A similar complication occurs in a stock trading application. An initial rule may be: Do not allow the portfolio to have more than X percent of its value in a single stock. However, the condition:action rules to accomplish this may be more complex. In particular, a rule for increasing a stock position or selecting the amount to buy may need to avoid having the amount exceed this X percent of the value of the portfolio. However, if the value of one stock goes up significantly or the value of the rest of the portfolio falls significantly, it is possible that this X percent threshold is again exceeded and needs corrective action. The exact action may be dependent on various factors, including which of these scenarios is causing this constraint to be of concern. As a note of clarification, the term "vehicle" is used in an investment context to denote a particular investment category as an "investment vehicle".

Another challenge is actions in dynamic environments/applications are not instantaneous acts, but may require taking place over a period of time during which conditions can change. For example, in a medical application, triggering the action to start having the patient take a particular medicine does not immediately produce results. Moreover, even after initiating this treatment, the condition of the patient could suddenly change, calling for a different treatment plan. As referred to herein, "suddenly" means relative to the time required for the selected treatment to have effect. Thus, the rule set may be further complicated by needing to take into account actions that have initiated some behavior but have not completed.

Another challenge for RBS is these applications may have an unbounded number of actions to be taken and thus an unbounded number of conditions to evaluate to select these actions, and/or these conditions may be changing rapidly and unpredictably. For example, a self-driving vehicle operating in an environment in which there are many other independently controlled vehicles has to implement the constraint of not colliding with these other vehicles even though it cannot predict the behavior of these other vehicles. Similarly, in an automated stock trading system, the prices of the stocks themselves may vary significantly outside of the control of the control system.

A control system may implement actions that respond to these dynamic changes to try to maintain the constraints that are specified for the control system. One challenge is specifying the logic for this control that is correct, efficient, and reliable, when there may be an unbounded number of dynamic scenarios that may arise and thus an unbounded number of cases to consider in the control logic. This challenge is further complicated by the fact that actions in many cases may not be performed instantaneously, so the environment may change further during the execution of an action.

There is often a basis for a top-level plan based on the knowledge of the environment, referred to as "route guidance" herein and in a navigational context. For example, an autonomous vehicle ("AV") may use conventional vehicle navigator technology based for example on GPS ("global positioning system") to generate a plan that follows a reasonable sequence of roads and intersections to the destination. In a financial environment, an automated trading platform may navigate a portfolio through a stock market. The stock market is itself a dynamically changing collection of stocks, over time. In a medical environment, a medical treatment plan may navigate a patient back to health.

In essence, the route guidance module produces a sequence of waypoints that correspond to key roads and actions at intersections. Similarly, there may be a top-level plan for automatic stock trading, based on P/E ratio, different indexes, trading strategies, and so on, with the waypoints being the open of trading in the morning to the close of trading at the end of the day, at least in a day trading application.

However, this type of top-level plan does not necessarily take into account the specific dynamic aspects of the environment that may occur between the waypoints. For example, an AV entering to an intersection where it is to turn left needs to switch to the left turn lane before the intersection and then negotiate the turn while complying with the constraint that the vehicle must avoid colliding with other vehicles and obstacles even though it cannot accurately predict what other vehicles and dynamic obstacles can do while it is executing this plan. Similarly, there may be stock market changes, such as change in interest rate, that may not be predicted and may call for a rapid reaction plus constraints such as not becoming overweighted in a particular industrial sector. As referred to herein, this form of navigation is a "dynamic navigation" because it takes into account dynamic elements in the environment.

Traditional approaches in autonomous driving have focused on implementing dynamic navigation by generating a short-term plan, sometimes called "motion planning", to navigate from one waypoint to another while obeying constraints, taking into account these constraints and the dynamic conditions in the environment. Then, the control system, on a moment by moment basis, has to implement control to follow this short term plan. That is, the complex task of determining a path that complies with all the constraints is modularly separated from the control mechanism for carrying out this short-term plan.

A problem with this motion planning/short-term planning approach is that a new dynamic condition may arise unexpectedly that makes the current plan infeasible. For example, a short-term plan may be for an AV to drive straight for the next 500 meters, change to the left turn lane, and then turn left at the intersection. However, a box may fall off the vehicle in front of the AV, suddenly creating a new unexpected obstacle to the vehicle, making this plan unacceptable because it fails to avoid an accident that an attentive human driver could avoid, namely by steering around the box. At the point of an unexpected event of this nature, because of its dependence on the short-term plan, the system may be unable to react until a new short-term plan is generated. As an example in the stock trading domain, an explosion at an oil refinery could change the prospects for certain dependent investments, requiring quick but unplanned changes to the portfolio.

One approach is to generate multiple short-term plans so that the system can switch to another short-term plan when an unanticipated event occurs. However, there may still be a delay to re-evaluate whether these alternative short-term plans are still valid relative to the new scenario, given the dynamic event that invalidated the current short-term plan. Moreover, it is infeasible in general to have sufficient alternative short-term plans such that there is always an acceptable alternative, so there is still the possibility of a system ending up with no short-term plan to follow for the new scenario, and thus a significant delay to react to the dynamic event. Put another way, short-term planning may make sense for a static abstraction environment like a game of chess but does not allow fast response in the real world.

The cost of generating a short-term plan is significant because it requires motion planning through a collection of other objects, some of which are also dynamic, for example objects in motion. Here, motion planning may be viewed as defining a path through an N-dimensional space such that all the constraints on the vehicle are satisfied all along the path. For other objects in motion and relevant to these constraints, it is further necessary to predict their behavior over time to verify that the plan is non-colliding at a later time t with each object's position at that time t, not just its current position. This prediction adds to the expense but also necessarily adds to its uncertainty with a probability of being wrong, further raising the possibility that the plan ends up being infeasible because of some unpredicted behavior or event. For example, a vehicle in the left lane up ahead of this vehicle could suddenly slow down, placing that other vehicle as an obstacle to this vehicle changing lanes as planned. In essence, the short-term planning approach in a dynamic environment leads to significant overhead in generating and regenerating these plans, then after selecting a current plan results in poor worst-case latency in reacting to dynamic events that invalidate the current plan, especially if one or more dynamic events invalidate all the precomputed plans.

In addition to these challenges, traditional uses of RBS have struggled because of the inefficiency of executing rule-based systems and the unmanageable complexity of the rules as they are extended to handle realistic scenarios.

A technique for reacting quickly to the dynamically changing environment without incurring the overhead of generating short-term plans or courses of action is disclosed. Embodiments implementing the technique include self-navigating vehicles, an automatic stock trading platform, medical treatment or other applications that exercise control or recognition in a dynamic environment. As referred to herein the term "automated dynamic navigation" is defined as the process of determining and maintaining a course or trajectory to a goal location. This trajectory may occur in a generalized N-dimensional space and the "determining" step includes navigating a path through this space that is consistent with the constraints imposed on the controlled system.

A control system implementing automatic dynamic navigation for a controlled system (or "vehicle" as referred to herein) through a dynamic "lane"-structured environment using a rule-based system where the triggered action is to dynamically select and execute a "lane maneuver" to achieve this navigation is disclosed. That is, navigation is achieved by executing new lane maneuvers and discontinuing existing lane maneuvers in response to rule triggering, where the rule conditions are responsive to changes in the environment and the vehicle.

As referred to herein, a "lane maneuver" is an action performed over time that controls the vehicle relative to lanes. For example, a simple maneuver is maintaining the vehicle's speed in the center of the current lane. In one embodiment, a maneuver is an action that is performed independent of dynamic changes to the environment during the time of the action. For example, a lane change to the right adjacent lane is a maneuver for an AV.

Lanes. A lane is a discretized directional path segment that the controlled vehicle may transit under certain conditions through the N-dimensional space in which it is contained from the lane start to its end while complying with non-dynamic constraints. For example, a physical road in the self-driving car application are discretized or divided into physical lanes or path segments that are each wide enough and smooth enough for the vehicle to transit. For example, on a two-lane road in the US, the vehicle is expected to stay in the right-hand lane except when passing. Without limitations and as detailed below, lanes are an abstract concept that may be applied to physical lanes in the AV application but may also be applied to other dynamic environments like stock trading and medical applications.

Lanes impose structure on the environment or space to be navigated. That is, rather being able to drive anywhere, the vehicle is constrained to drive in one lane or switch to another and then drive in that lane. For example, on a six-lane divided highway, the vehicle either drives in the rightmost lane, the middle lane or the leftmost lane, except when it is changing lanes. Thus, the lane concept reduces the choices for action in the short-term. For example, a vehicle may either proceed in the current lane or else switch to another. As a side note, it may be possible to specify a lane-structured environment in which it is impossible for a vehicle to get from one destination to another but it is not useful to do so.

The lane structuring restricts the choices that a vehicle has to navigate. For example, in the self-driving car case, a vehicle may have to navigate with respect to lanes, for example follow the current lane, switch to an adjacent lane, or turn into a lane on another road at an intersection.

The restrictions of lanes may mean that some navigation plans that could otherwise be executed may not be considered or supported. For instance, if a road is completely blocked, it may be physically possible for the vehicle to go "off-road" and still get to the destination in an unconstrained navigation. However, with lane-structured navigation, unless a lane is provided around the blockage, the vehicle is forced to stop and may not make it to the destination without manual intervention.

Lane-structuring also may mean that the vehicle dynamic navigation may also assume that other vehicles use lane-structured navigation as well. For example, the vehicle control may assume that an approaching vehicle may remain in the lane it is in and not suddenly deviate into the current vehicle's lane. By making this assumption, lanes may allow some driving that would not otherwise be feasible. For example, consider the constraint: the vehicle should not have a closing velocity V with another vehicle at distance D that exceeds the vehicle's ability to slow down by V within the time to travel D. This constraint is restricted to just other vehicles in the same lane as the current vehicle. This restriction to lane-based behavior is precisely what allows a driver to assume it is safe to continue driving in the current lane when there is a fast approaching vehicle in the adjacent lane.

The lane restriction is critical for safe navigation because it is physically impossible to handle many common scenarios without dependence on lanes and associated vehicle behavior. For example, an oncoming vehicle on a two-lane road is normally in its own lane traveling at say 65 miles per hour. It is physically impossible for a controlled vehicle to avoid a collision if this oncoming vehicle suddenly veers into its lane, given the high closing speed. If there were no lanes, a vehicle could not travel at any significant speed if oncoming vehicles could choose to navigate to anywhere on the road at any time. Similarly, the vehicle passing parked cars cannot physically avoid a collision if a supposedly parked car suddenly pulls out into its lane.

In the case of on-road vehicle navigation using high-definition (HD) maps, the lane information is available to the vehicle a priori to driving in this area. The vehicle then needs to perform localization to maintain the location of this vehicle on the HD map. There are existing techniques to use GPS, dead reckoning and visual or other lane marking indications to achieve localization of the vehicle with high accuracy.

Figure 2:
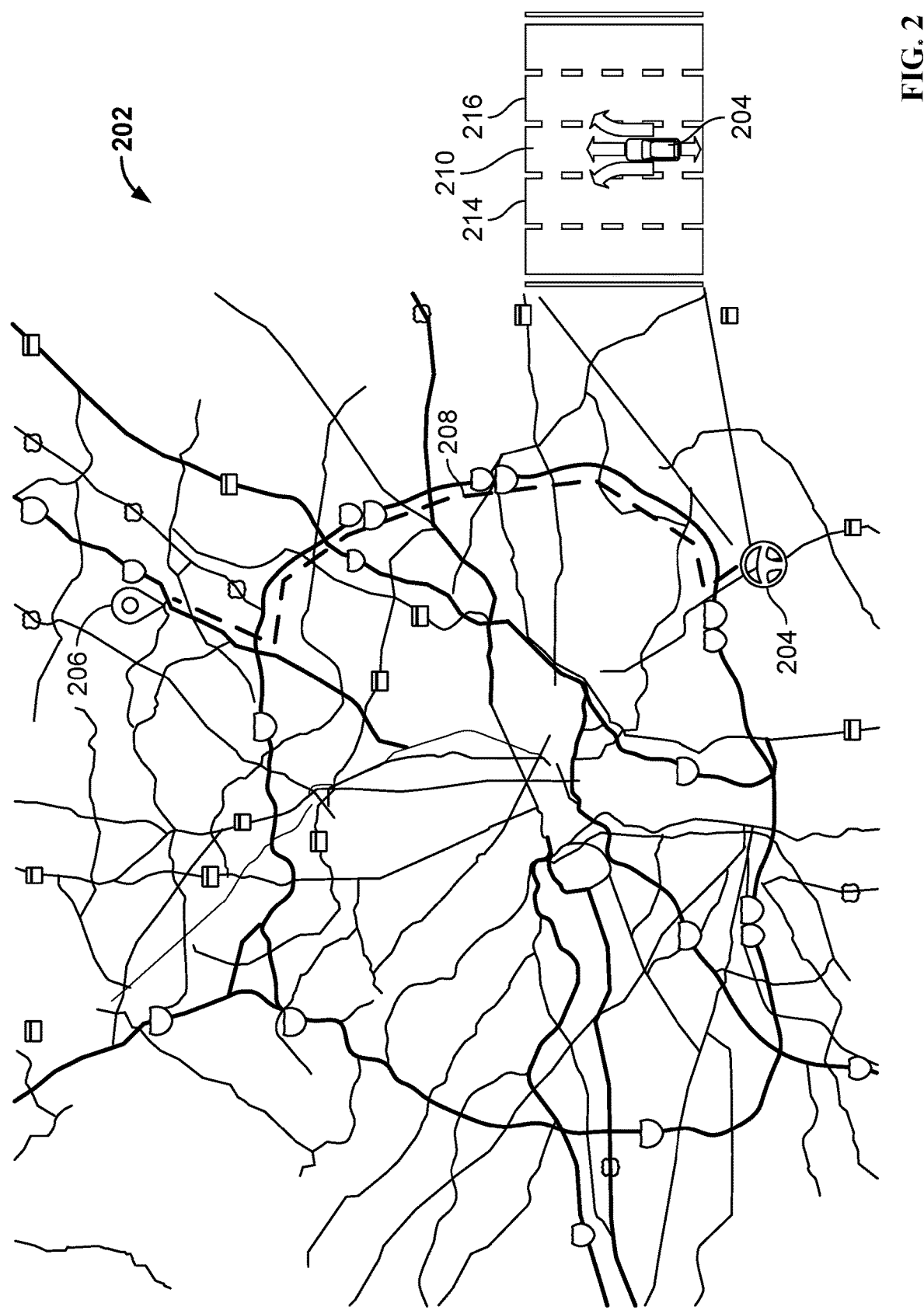
FIG. 2 is an illustration of lanes in an autonomous vehicle application example.

FIG. 2 is an illustration of lanes in an autonomous vehicle application example. Map (202) illustrates an AV (204) with a location goal (206). An example of a top-level plan (208) includes a series of waypoints as it navigates on and off various highways, roads, and transition roads like on-ramps and off-ramps. Along this plan, the AV (204) travels in a current lane (210) with two adjacent lanes (214), (216).

Lanes in Other Domains/Applications. In a stock trading domain, there are lanes based on classification of stocks into different industry segments. Commonly, other market participants do not suddenly switch all investments into another random set of stocks. Instead, certain dynamic events such as oil refinery explosions, interest rate changes, and other examples are known to impact particular "lanes" or industry segments. Therefore, a portfolio may react to dynamic events by recognizing that each event only impacts one or more lanes of investment, and the constraints associated with those lane(s). For instance, a major explosion at an oil refinery might negatively impact the company operating the refinery, but benefit other companies in the oil refinery "lane", and negatively impact other companies are highly dependent on oil, such as companies in the transportation "lane".

Unlike the self-navigating vehicle case, the automatic stock trading application may have hierarchical "lanes", a top hierarchy of consumer products, a mid-level hierarchy of the dry goods sector, and a lower-level hierarchy of particular stocks/companies. It may also have multiple investment themes that correspond to effectively controlling multiple vehicles/subvehicles at the same time, complying with constraints between these, such as avoiding being long in too many companies that are growth phase companies across every "lane" of an investment theme.

Figure 3A:
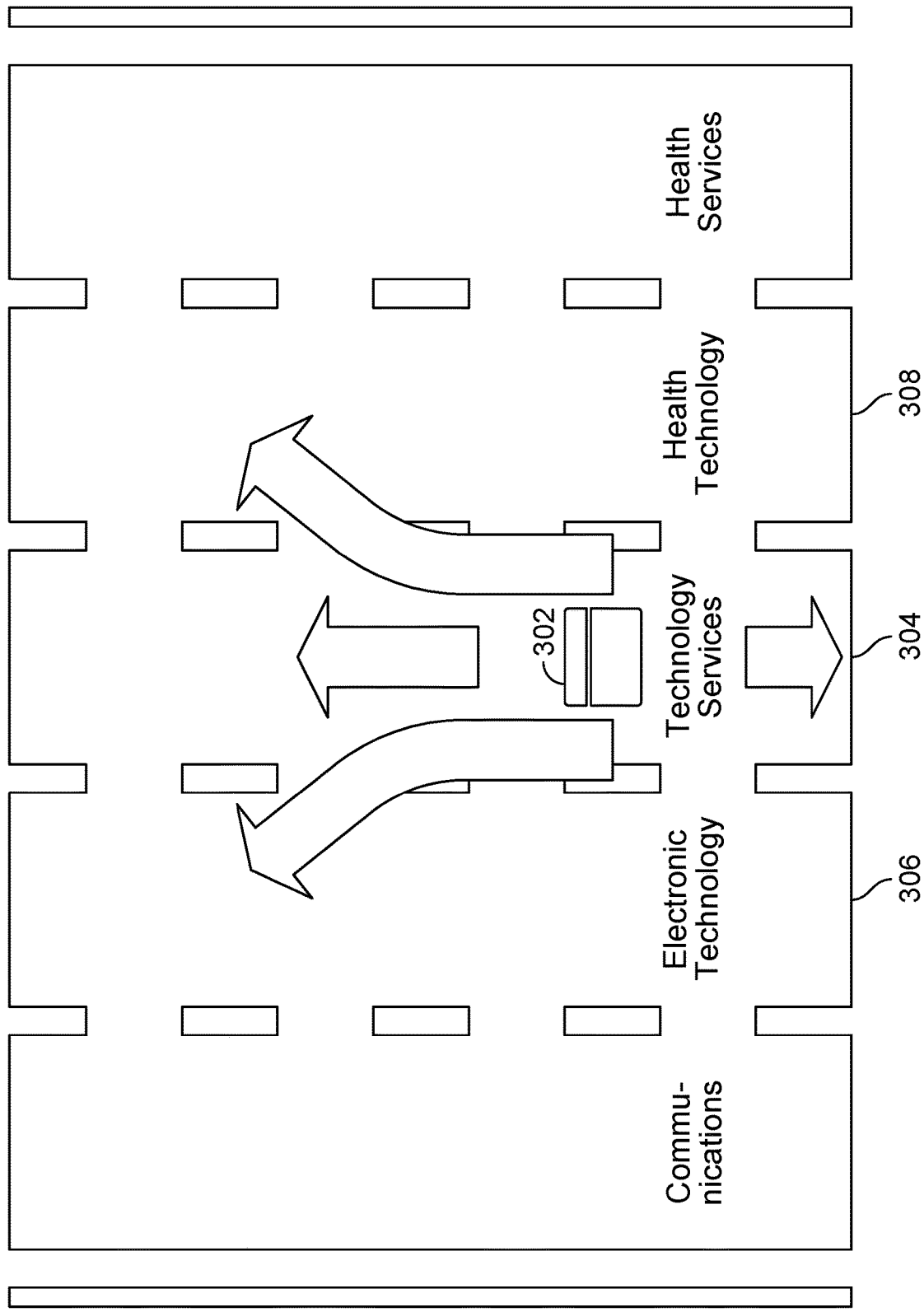
FIGS. 3A, 3B, and 3C illustrate an example of hierarchical lanes for stock trading.
Figure 3B:
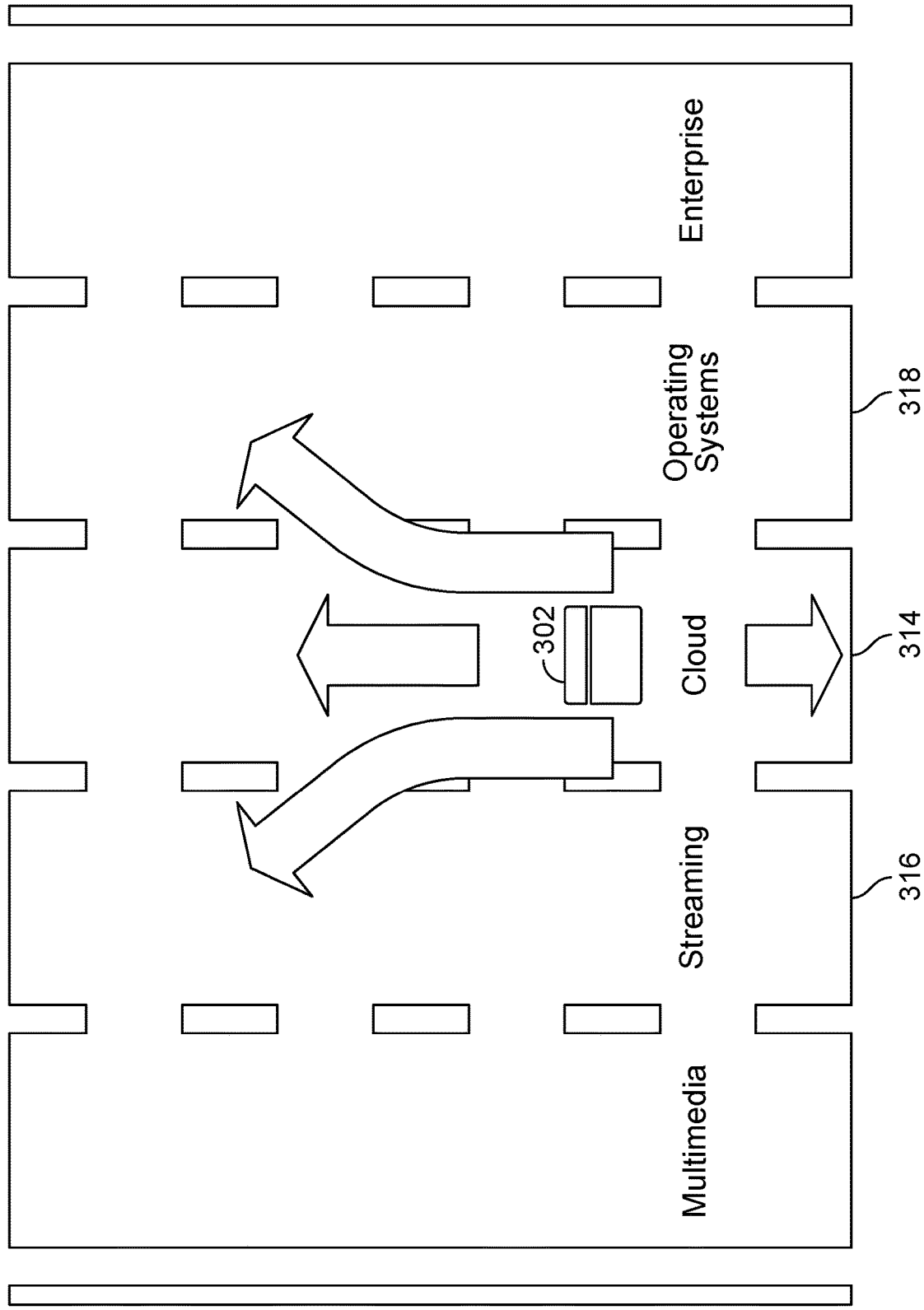
Figure 3C:
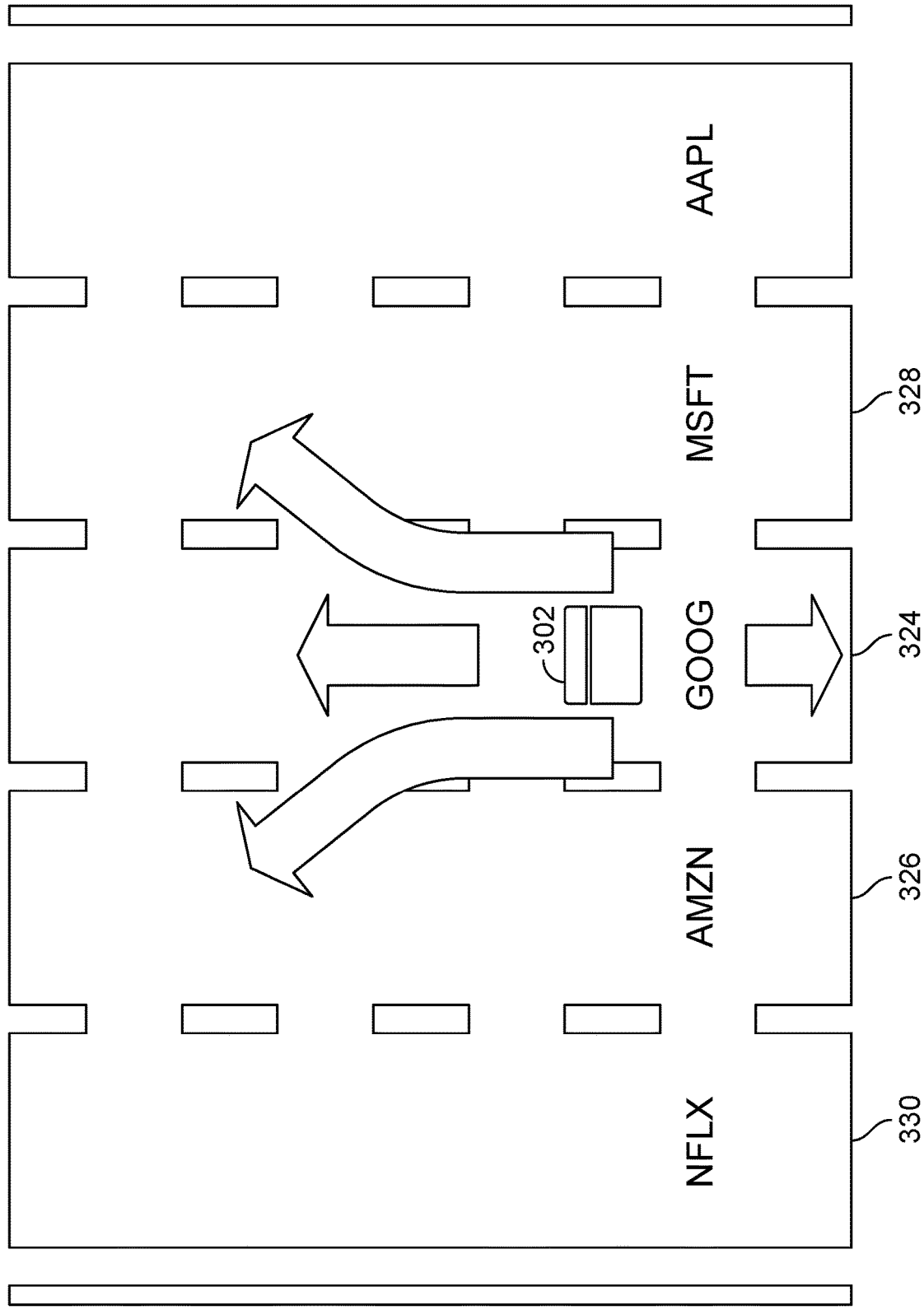

FIGS. 3A, 3B, and 3C illustrate an example of hierarchical lanes for stock trading. In FIG. 3A, the vehicle/app (302) is currently in a "technology services" top hierarchy lane (304), which is adjacent to the "electronic technology" top hierarchy lane (306) and the "health technology" top hierarchy lane (308). In other words, from lane 304, the vehicle/app may move to an adjacent lane such as lane (306)/(308). In FIG. 3B, the vehicle/app (302) is currently in a "cloud sector" mid-hierarchy lane (314) in the "technology services" top hierarchy lane. "Cloud sector" mid-hierarchy lane 314 is adjacent to the "streaming" mid-hierarchy lane (316) and the "operating systems" mid-hierarchy lane (318). In FIG. 3C, the vehicle/app (302) is currently in a "GOOG" lower-level hierarchy lane (324) in the "cloud sector" mid-hierarchy lane in the "technology services" top hierarchy lane. Lane (324) is adjacent to the "AMZN" lower-level hierarchy lane (326) and the "MSFT" lower-level hierarchy lane (328).

In this vein, stock trading may be viewed as navigating multiple investment vehicles/subvehicles at the same time with constraints between these vehicles, complying with these inter-vehicle constraints as well as constraints between the environment and each of the vehicles.

Figure 3D:
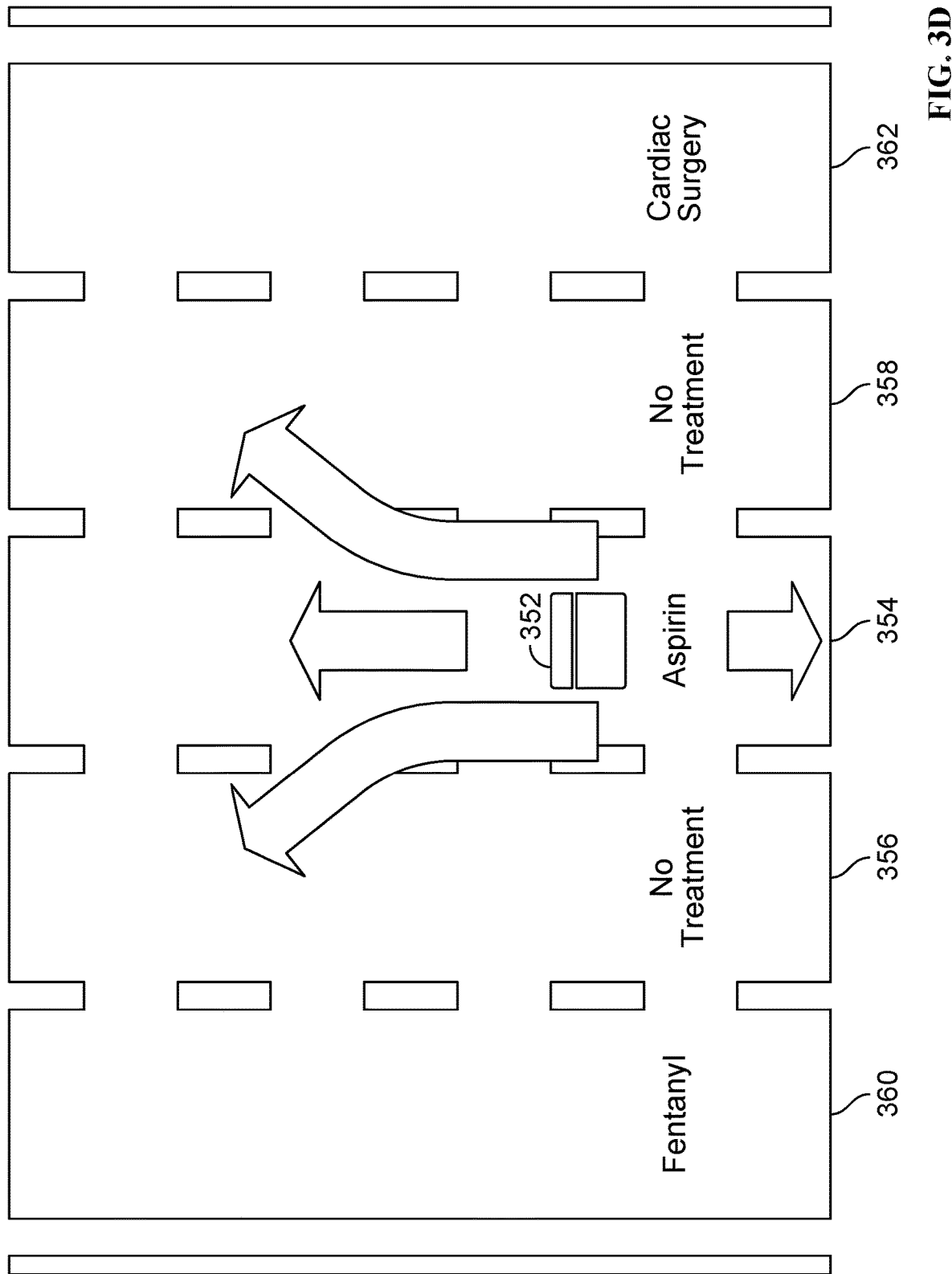
FIG. 3D illustrates an example of hierarchical lanes for a medical application.

FIG. 3D illustrates an example of hierarchical lanes for a medical application. The vehicle/app (352) is currently in an "aspirin treatment regime" lane (354), which is adjacent to two lanes of "no treatment regime" (356), (358), indicating the period it takes for a patient to stop an old treatment regime before starting a new one. One "no treatment regime" lane (356) is adjacent to a "fentanyl treatment regime" lane (360) indicating one possible new treatment, where the other "no treatment regime" lane (358) is adjacent to a "cardiac surgery treatment regime" lane (362). Without limitation, the illustrations of FIGS. 3A, 3B, 3C, and 4 are meant to draw parallels with the AV application of FIG. 2 by displaying lanes in two-dimensions, like a physical roadway. By conceiving in more than two dimensions, the same principles may be generalized to, for example, a three-dimensional set of lanes where the "no treatment regime" lanes (356), (358) are the same lane and other treatment regimes (354), (360), (362), etc. are all adjacent to the "no treatment regime". Without limitation, an N-dimensional space may be used for other applications.

Generic Lane View. In a most general formulation, a lane is generally a constrained directional path in the N-dimensional space that the "vehicle" is travelling that is adequate in the absence of dynamic obstacles for the vehicle to travel from one end to the other without violating vehicle constraints including static vehicle constraints. A lane may have certain dynamic and static characteristics and behaviors. For example, a lane corresponding to a particular patient treatment plan in a medical application may entail particular side-effects and may have a bounded time of application. Navigation entails following the current lane as well as switching to a different lane from time to time as appropriate to achieve the desired objective, such as to cure the patent. The vehicle, a patient in this medical application example, is not allowed to change to an arbitrary other lane from its current lane. Instead, it is only allowed to switch to adjacent lanes to the current lane.

The notion of "adjacency" is defined in application-specific terms and constraints. In particular, a lane L0 is adjacent to another lane L1 when it is feasible to execute a lane maneuver from L0 to L1 subject to some dynamic conditions. For example, referring to FIG. 3D, a patient being treated with Fentanyl, and thus in the lane (360), may not directly switch from this lane or treatment to an aspirin treatment lane (354) without going through the "no treatment" lane (356). This is required because there may be a bad interaction between drugs if the patient has some Fentanyl in their system when they start taking aspirin. Moreover, the patient is only allowed to switch from the Fentanyl lane if their symptoms have stabilized. The designation of adjacency between lanes is part of a lane-structured environment.

Lane Maneuvers. A "lane maneuver" is referred to herein as an action that takes place in terms of one or more lanes. For example, change-to-right-lane is a maneuver that changes the vehicle from the current lane to an adjacent lane on the right. Thus, as above, an "adjacent lane" is referred to herein as a lane that may be reachable from the current lane with a lane maneuver, similar to the physical two-dimensional lane in driving. In this sense, the lanes and their adjacencies serve to discretize the environment so the number of maneuvers is also conveniently finite and implementable. For example, a change of lanes to an adjacent lane is one of a small number of maneuvers and is straight-forward implement.

A maneuver can in many cases be a static, precomputed solution relative to the lanes. For example, a 'change lanes' maneuver is static where the lanes are a standard width—a simplified and standard motion plan may be used, perhaps parameterized by the speed of the vehicle. Moreover, a maneuver does not have to take into account dynamic events or obstacles. Therefore, an AV may take instantaneous action to perform a selected maneuver when a new maneuver is selected without having to generate the maneuver sequence or procedure dynamically.

Figure 4:
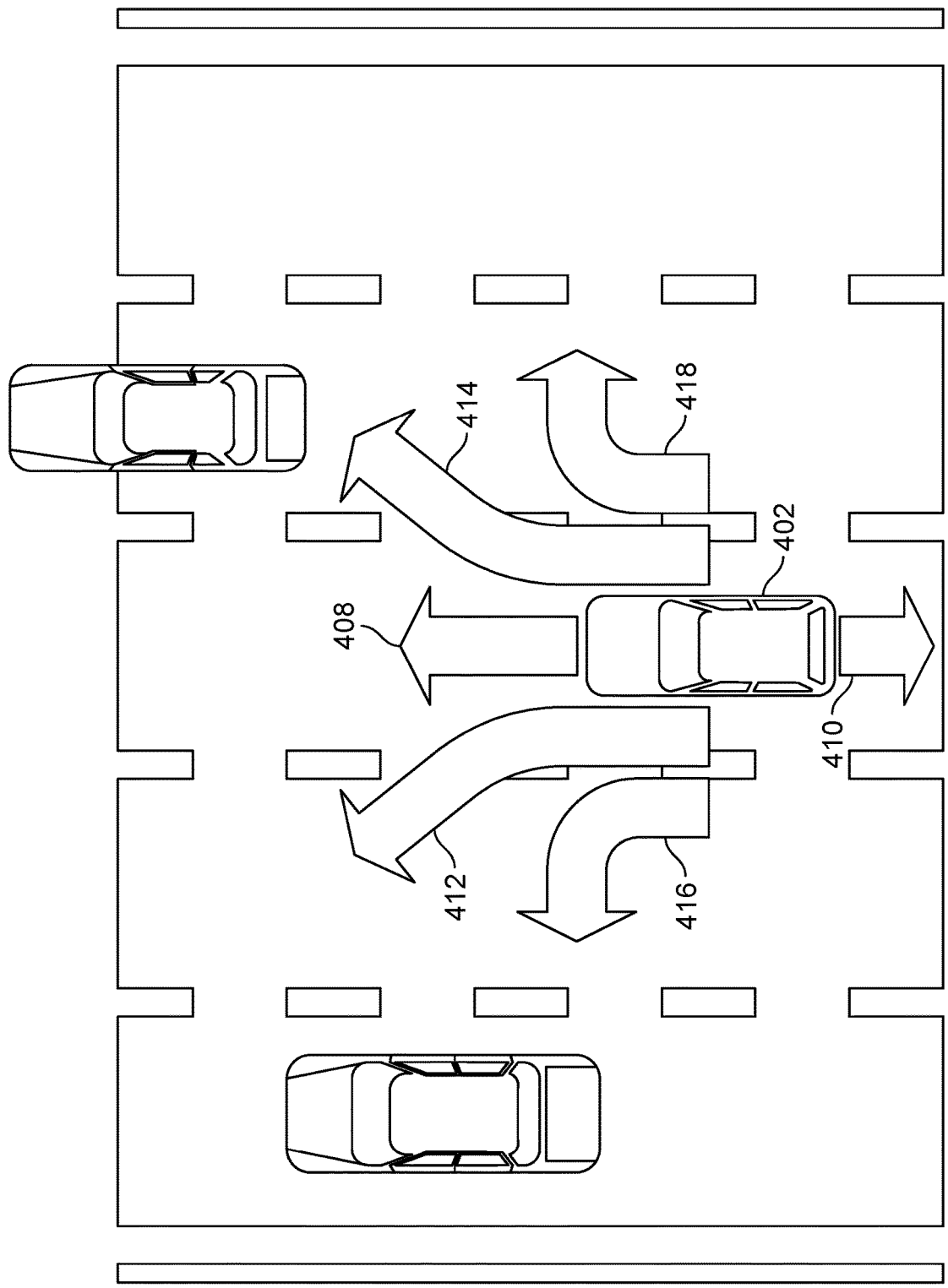
FIG. 4 is an illustration of lane maneuvers for an autonomous vehicle example.

FIG. 4 is an illustration of lane maneuvers for an autonomous vehicle example. In general, there is normally a bounded number of actions that the controlled system can perform, especially when actions are qualified by parameters. For example, a factory robot can reach forward, lift up, lift down, and so on. Similarly, as shown in FIG. 4 a vehicle (402) may slow down (410), speed up (408), change lanes to the left (412), change lanes to the right (414), perform a left turn (416), perform a right turn (418), and so on. These actions are a bounded set of actions, possibly parameterized by the speed, road conditions, and so forth. So, the maneuvers may be preset in the controlling software and/or implemented in hardware (e.g., hard-wired), and thus performed with quick response.

The lane structuring may be used to dramatically reduce the number of actions to consider at any given time. For instance, consider a flat plain that stretches from point A to point B. Without any lanes, there are an unbounded number of potential paths to take between A and B. With one lane in each direction between point A and B, the actions are reduced to staying in the driving lane (slowing down, speeding up or maintaining speed), changing to the other lane to pass, and changing back to the driving lane after passing.

In a medical context, there are a bounded number of lane maneuvers because there are established sequences in treatment that are known to safe. For example, the doctor should never prescribe a sudden change in treatment plan to one that is not known to be a safe change to make. In a stock trading domain, there are a bounded number of actions or maneuvers to perform, such as sell at market, stop-loss, and so on. Moreover, a stock portfolio that is required to have 10 percent of its assets in high-tech large cap growth cannot replace one such stock in the portfolio with an arbitrary other stock. Instead, referring to, for example FIG. 3C, if the portfolio has a large holding in AMZN (326), it can only replace this stock with GOOG (324) or NFLX (330) because these stocks are adjacent to AMZN (326). As mentioned earlier, this example of adjacency is illustrated in two dimensions. In reality, there can be many different stocks that are adjacent to AMZN, which easily handled in an N-dimension space.

It is not strictly necessary for the maneuvers to allow a vehicle or a robot to navigate in every possible scenario in which navigation is strictly possible; human drivers cannot either. For example, consider a zig-zagged collection of static obstacles and dynamic objects moving in some rapid pattern through an intersection or similar. It may be theoretically possible to safely navigate through this intersection but few humans would be able to navigate this situation. The situation is highly unusual so the inability to handle automatically would be acceptable, given the economic value of being able to safely drive in the actual real world scenarios of interest.

Thus, there are a set of basic lane maneuvers, for example in the AV context: maintaining speed in current lane, slowing down, speeding up, changing to right lane, changing to left lane, right turn, left turn, and so on. These maneuvers may be refined to more specific maneuvers. For example, slowing down may be refined to: emergency braking, hard braking, gradually braking and deceleration/cutting the throttle. The lane structure implies a relatively small set of base maneuvers that may be refined to a larger more sophisticated set.

By contrast, without the lane structure, there are an unbounded number of possible actions. Moreover, the number of conditions is at least the number of actions, so the number of rule conditions is also excessive unless the number of actions/maneuvers is severely restricted. In particular, without lanes, either an unbounded number of actions results such as "move right by 1 inch", "move right by 2 feet", "move right by 3 yards", and so forth, or else the action is parameterized without limit or without a meaningful limit. For example, if the action is to move right by X feet, a very large value may have a different realization than a small value, so is hard to implement per se. By contrast, with lanes, changing lane to right is used for a small movement, but to go a significant distance to the right, the vehicle turns to the right and then follows the lane going right and then may turn left to continue forward.

In one embodiment, lane maneuvers are implemented to be "preemptable" as referred to herein as when a new maneuver may be triggered immediately even though another maneuver is being executed. The new maneuver is able to take over and execute its maneuver, taking into account the intermediate state of the vehicle based on the previous maneuver. For example, the maneuver of changing to a passing lane and accelerating may be triggered previously but before this action is completed, a dynamic obstacle is detected that triggers the maneuver to slow down and return to the driving lane. This maneuver recognizes the current position of the vehicle with respect to the driving lane and adjusts its steering actions based on the offset of the vehicle relative to the driving lane. In particular, if the vehicle has only slightly departed from the driving lane at the point that this new maneuver is triggered, the steering action may need to be less aggressive than if the vehicle is already fully in the passing lane.

Lane Subconditions. A "lane subcondition" is referred to herein as an input that indicates the state of one or more of the lanes relative to this vehicle or other objects. For example, hasRightLaneClear is a subcondition that is true if the right lane relative to this vehicle is clear of obstacles. It is a lane subcondition as it is tied to the state of a lane.

Just as the lane structure reduces the number of lane maneuvers, it also reduces the number of lane subconditions that are required. This is because the only actions are relative to lanes as lane maneuvers, so it is acceptable to only consider subconditions relative to the lanes. That is, if the only choice of actions is one of the lane maneuvers, the condition for selection of a lane maneuver should be adequate if expressed in terms of lane subconditions. With lanes, the conditions of interest are reduced down to those that should trigger each of these actions. For instance, the action of slowing down in the current driving lane has a small number of subconditions tied to the state of the current driving lane and possibly the adjacent lanes as well as the current position of vehicle in the current lane.

Lane subconditions are often easier to determine from the sensors on the vehicle because most or all of the relevant subconditions are associated with the current lane or adjacent lanes and relative to the vehicle. For example, has-RightLaneClear subcondition is relative to the vehicle and can be sensed by sensors on the vehicle including cameras, microwave, radar, and lidar, on the right-hand side of the vehicle. A lane subcondition is also local to a controlled vehicle, making it easier to sense accurately.

The lane structure also allows the exclusion of subconditions that may cause false positive reactions. For example, without lanes, a vehicle may want to sense whenever there is an object that has a high closing speed to this vehicle. With lanes, on a two-lane highway that curves slightly, an on-coming vehicle in the opposite lane may appear to have such a high closing speed: With the lane structure, the vehicle may recognize there is an on-coming vehicle in the opposite lane and only use this subcondition to preclude passing in the opposite lane and not otherwise react to it.

It is possible to hypothesize a scenario in which lane subconditions are not adequate. For example, a rock may drop off a tall cliff adjacent to the road, dropping directly onto the vehicle. With additional subconditions that are driven off of aerial sensors, it may be possible to avoid this collision. However, these are extreme and unusual circumstances that are beyond what human/manual drivers could typically handle. Nevertheless, it may be feasible to extend sensors on the vehicle to detect subconditions that are relevant above the lanes and thus treat these as additional lane subconditions, as required in this extreme example.

With lane structuring of the environment, RBS navigation is realized by having rule conditions, as lane subconditions, triggering the rule actions, as lane maneuvers. For example, in the application of a self-driving car, one subcondition may be that the current lane is blocked ahead. Another two subconditions may be the adjacent left lane and the adjacent right lane are free. A final subcondition may be that a right hand turn is coming up. With this set of subconditions, it is reasonable for the vehicle to select the maneuver of switching to the right lane, rather than braking or switching to the left lane. That is, the rule for the above may be implemented as:

if(laneIsBlocked and rightTurnImminent and rightLaneClear) {changeToRightLane( );
    }

Note that the subcondition of the leftLaneClear is not required for this rule and so is not included in the lane subcondition.

In general, the lane-structured environment results in a relatively bounded set of maneuvers and a relatively bounded set of subconditions to consider, so the rule set is of reasonable size to design, verify and execute.

Route Guidance. To incorporate route guidance into this rule structure, the route guidance input may be treated as dynamic events/inputs based on the changing position of the vehicle. For example, as an AV travels down the lane of a highway, it may dynamically enter a portion of the highway in which the route guidance determines it is close to an exit on the right that it needs to take, according to the route guidance. A conventional vehicle navigational system would generate an indication of an exit coming in say 0.5 miles.

In one embodiment, there is a subcondition value defined that corresponds to "right exit in less than 0.5 miles" that may be set as an input at that point, based on information from the route guidance system. There can be similar subcondition values for "right exit in less than 0.1 miles" and at other distances.

By having the rules triggered by both external object subconditions as well as these route guidance subconditions, the vehicle may be navigated to avoid obstacles as well as navigated towards the desired destination by the same mechanism. In particular, in the case of a subcondition "right exit in less than 0.5 miles" being set to true, a rule may trigger to change to the rightmost lane if other subconditions indicate it is safe to switch to this lane. Similarly, when the right lane leads to the freeway exit, a subcondition may be set that causes the maneuver of following the freeway exit lane. In this way, the dynamically changing position of the vehicle is triggering subconditions from the route guidance system that trigger maneuvers that achieve the desired navigation of the vehicle to the destination, in the absence of interfering obstacles.

It is possible that dynamic events cause the vehicle to not follow the route guidance. For example, a severe congestion of vehicles in the right lane may make it infeasible to reach the upcoming exit in time. In this case, the vehicle navigates past this exit. The route guidance system then recomputes the route to take, the same as may arise with a human driver that fails to execute the route provided by the route guidance.

Developing a Lane-Structured Rule set. A first step in developing a lane-structured navigational rule set is defining the vocabulary of lane maneuvers that the vehicle may execute. These maneuvers can be quite simple, such as maintain the current lane, change to the right lane, change to the left lane, and so forth. Unrelated to this first step, note that there is a separate task of implementing each maneuver in the vehicle control system. This task entails implementing a procedure per maneuver, possibly using traditional techniques.

The second step is identifying, for each lane maneuver, conditions under which this maneuver should be triggered. Each such condition may be expressed as a Boolean expression in terms of lane subconditions, which are refined down to observable subconditions. For example, to repeat an earlier example, the condition to change to the right lane is expressed as a conjunction of lane subconditions:

```
if(laneIsBlocked and rightTurnImminent and rightLaneClear)  {
    changeToRightLane( );
}
``` where the laneIsBlocked and rightLaneClear subconditions are determined by a vehicle sensor system and the rightTurnImminent subcondition is perceived in some sense by a route guidance system based on input from the vehicle localization system and the static map of the area. Note that the "rightTurnImminent" is considered a lane subcondition because it is based on the localization of the vehicle in the lane, that is where it is, plus the route guidance. Note further that there is required to be definition of a lane structuring model that includes the possible adjacencies as well as these lane subconditions. For example, the above example assumes that the adjacent lanes can be generically and fully designated as "right lane" and "left lane".

Similar to lane maneuvers, lane subconditions may be refined from basic ones to more sophisticated specific lane subconditions so that the lane subconditions are adequate to express the rule condition for triggering each refined maneuver. For example, the rule set designer may recognize that the "changeToRightLane" is too general and not adequate for safe driving. For example, a situation where there is sudden blockage in front of the vehicle that is in very close proximity may call for an emergency maneuver such as "swerveToRightLane" whereas a change of lanes just to prepare for making a right turn may have no such urgency. Thus, the "laneIsBlocked" may be refined to subconditions such as "imminentUnknownLaneBlockage", "vehicleInFrontSlowing", and "vehicleInFrontBraking", for example.

Conversely, the rule set designer may start with a rule that calls for an emergency stop when there is a sudden blockage in front of the vehicle that is in very close proximity. The refinement is to recognize that it may be preferred to swerve into the right lane if the right lane is clear. Consequently, the rule set designer can add the "swerveToRightLane" and "swerveToLeftLane" maneuvers, then refining the existing rule conditions between these maneuvers based on whether the right or left lanes are clear. In general, the refinement of lane maneuvers to address different driving situations calls for the refinement of lane subconditions to allow the rules for these maneuvers to be expressed properly.

Ternary Fault Scenario Representation Overview and Embodiment. In one embodiment, this rule set is expressed as embedded into an object model as instructed using a ternary fault scenario representation. An illustrative application of ternary fault scenario representation is automatic root cause analysis (ARCA). A "symptom" is referred to herein as a named and/or defined state of some component of a monitored system that is important to distinguish one fault scenario from another. In one embodiment, a symptom value corresponding to an "unknown" value corresponding to a symptom value that is not known, and a "don't care" value, also referred to as an extraneous value corresponding to a symptom not needed for a particular analysis are used.

In one embodiment, each symptom value is restricted to being one of: true, false, or unknown. Thus, a symptom value is referred to herein as being a "ternary" value. In one embodiment, the unknown and the "don't care" values are designated by the same value, distinguished as one or the other based on the context of usage. For example, for an AV application the "vehicleInFrontSlowing" subcondition may be unknown in the event the AV is in foggy conditions, or "vehicleInFrontSlowing" subcondition may be "don't care" in the event the AV is parallel parking by reversing.

Overview of Automated Root Cause Analysis (ARCA). Complex monitored systems may have numerous sources of faults and even the mechanisms for monitoring such a system are subject to failures as well. For example, a temperature sensor monitoring a refrigeration system can fail, either permanently or intermittently, indicating incorrect temperatures for the system being monitored.

Component dependencies may introduce further complexity, for example, the cooling coils in a refrigeration system depend on correct operation of the compressor to provide condensed refrigerant. These dependencies arise from the interconnection of these components. As described above, the failure of one component may lead to another indicating a fault condition/symptom. Consequently, when one component has a fault, it may lead to cascading faults in the components that are dependent on the faulting component, making the task of determining the actual root cause fault difficult. In some cases, the root cause may not even be present among the alerts provided to the operator.

For example, if a cable fails between two computer network switches, there may be a flood of alerts from the switches at either end of the cable. However, there is typically no alert directly indicating the cable break because there are no sensors directly on the cable able to detect a cable breakage. A complex system may also be implemented in multiple layers, creating another set of dependencies. These layer dependencies are another source of alerts. For example, the above cable failure may cause the transport layer to indicate it has sessions timing out because no acknowledgements are being received. Similarly, a misconfiguration at the IP layer may cause alerts at the TCP/transport layer and routing layer to be generated.

Traditionally, these extra alerts are referred to as symptoms of a root cause fault. Generating a large number of these symptoms as alerts makes determining the actual root cause more difficult.

By using efficient matching of symptoms without requiring the use of statistical correlation between faults or impractical/costly large training datasets, an efficient way of encoding the principles of operation, the dependencies and causations, and the potential root causes that are known for an engineered system as a result of its engineered design is described. This efficiency reduces storage costs and/or decreases power consumption for processors in order to determine root cause analysis. This efficient way allows root cause analysis to be performed automatically and efficiently.

Figure 5A:
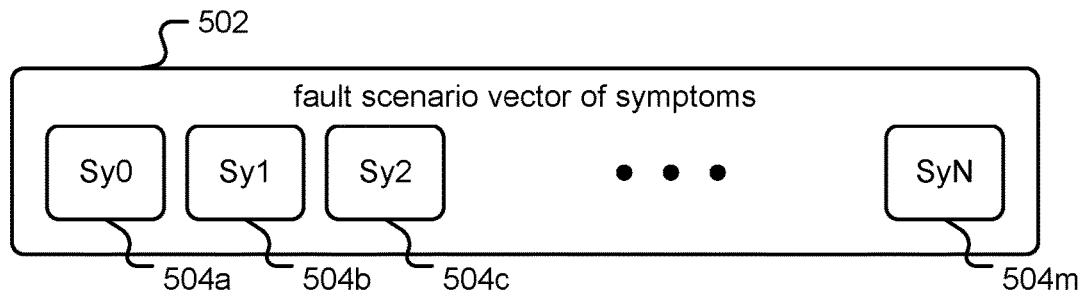
FIG. 5A is an illustration of an example of a fault scenario vector of symptoms.

Symptoms and Fault Scenarios. FIG. 5A is an illustration of an example of a fault scenario vector of symptoms. One example of a symptom, noPower, is a symptom indicating that there is no power coming to the monitored system. The state of a symptom may be a known value or a special indication that it is unknown and/or "don't care." The term "don't care" is commonly used in digital logic to indicate that the associated item is extraneous/not required. The ability for the processing to indicate "don't care" for a given symptom allows analysis to proceed even when that aspect of the state of the system is not actually known.

A "fault scenario" is referred to herein as a collection of symptom values that indicates the known and unknown fault state of a monitored system. Logically a fault scenario represents the state and/or potential partial state of the system from the standpoint of observed/determined symptoms that something is wrong or not wrong with the system. It may not indicate the full state of the system. For example, with a vehicle, the fault scenario may not necessarily indicate the position, velocity, and so forth of the vehicle, only the state of the symptoms, that is, the aspects that are needed to perform root cause analysis of faults.

As shown in FIG. 5A, in one embodiment, a fault scenario is represented as an array of values (502), where each entry (504a-m) corresponds to a specified symptom. For example, symptom Sy0 (504a) is a first entry, symptom Sy1 (504b) is a second entry, and so forth. In one embodiment, there may be multiple symptoms associated with the same metric. For example, there may be different symptoms for a temperature sensor being slightly high, moderately high, and extremely high. In one embodiment, there may be symptoms associated with the same metric based on different levels of derivative. For example, a symptom may be associated with a metric having a first derivative that is zero for too long, that is, it is constant, often indicating that the input sensor has failed. A symptom may be associated with the first derivative being too high, meaning that it is changing too quickly.

There may be additional symptoms associated with a metric that indicate that the metric is out-of-range or behaving incorrectly. In this case, the out-of-range symptom is set at the same time as a symptom indicating the metric is too high or too low, for instance. This "aggregate" form of symptom may allow a fault scenario to be specified in terms of "out of range," rather than having to cover both "too low" and "too high."

A match operator is defined between two fault scenarios s0 and s1 to return true bool isMatching=match (s0,s1);

if every symptom entry in s0 is either "don't care" or else matches as the value in the corresponding entry in s1. Note that the match operation is not commutative; match(a,b) may not necessarily be equal to match (b,a).

Figure 5B:
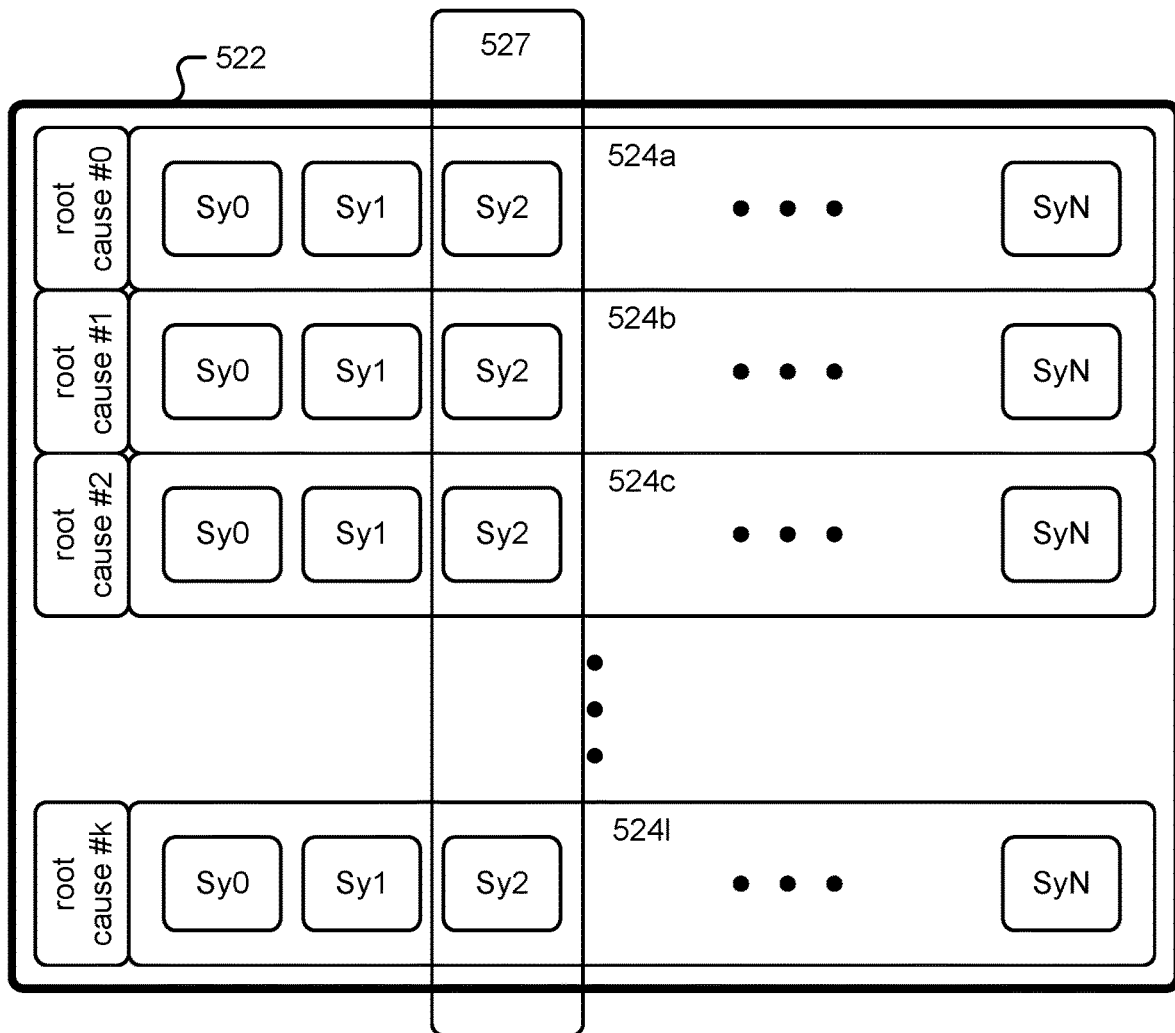
FIG. 5B is an illustration of an example root cause table.

Root Cause Table. FIG. 5B is an illustration of an example root cause table (RCT). An RCT is a table in which each row is a fault scenario that is labeled with an associated root cause. In this context, an unknown value for a symptom in such a fault scenario is interpreted as "don't care." For example, for a root cause "front obstacle," symptoms in the row may be: vehicleInFront as true, movingForward as true, and all other symptoms indicated as "don't care."

In one embodiment, an RCT contains a row for every failure or event that can be the root cause, where each row indicates the symptoms that must be true for this to be the root cause, those that must be false, and the rest set as indicating "don't care." Note that specifying more symptoms as specific values, rather than "don't care" beyond the absolute minimal for a given root cause can result in a root cause not being identified or matched because extra symptoms may not be known or are the opposite of that specified for the row. Consequently, it is important to specify the minimal set of known symptoms required to diagnose the system to the particular root cause associated with the row in the table. If a given root cause may have multiple identifying sets of symptoms, there are multiple rows in the RCT, as a row per set. A given root cause may have multiple corresponding rows because one row corresponds to a minimal set of symptoms and others correspond to the minimal set with additional symptoms that provide greater confidence in the root cause. For example, in the case of a power supply failure to a switch, the minimal set may just contain the "lossOfPower" symptom from the switch's current sensor while additional rows may contain that symptom plus "lossOfSignal" symptoms from the directly attached switches to the failed switch.

In one embodiment, each RCT row is represented in the same way as a fault scenario. As such, it may be referred to herein as a "potential fault scenario." As shown in FIG. 5B, an RCT (522) comprises k+1 rows (524a-524l), each row associated with a specific root cause with N symptoms per row. For example, root cause #0 is associated with the first row (524a). The values of the symptoms (504a-m) in each row (524a) are different from the other rows (524b-524l), each corresponding to a potential fault scenario for the associated root cause, as indicated by the root cause labeled #0 through #k.

In contrast to a potential fault scenario, the fault scenario determined from a monitored system is referred to herein as an "actual fault scenario". There may be multiple actual fault scenarios for a monitored system. One actual fault scenario may be a more detailed fault scenario for a particular subsystem compared to another. Another source of multiple actual fault scenarios is uncertainty regarding the faults. For example, one scenario may have a symptom corresponding to the temperature of the system being too low whereas another may have a symptom indicating that the temperature sensor has failed. In the latter case, it may indicate the temperature sensor-dependent symptoms as unknown.

As described above, ternary symptom values are used so that a symptom is represented as a "known" bit indicating known or unknown by being true or false respectively, and a second "value" bit that indicates true or false, which is only interpreted as such if the known bit is set to true. The quaternary nomenclature of [a, b] is used, again such that an interpretation of [0,1] that is allowable is that an associated symptom is not known to be true. Thus [0,0] which may correspond to unknown differs from [0,1] which may be interpreted as not known to be true. Note that a [0,1] symptom in an entry in an RCT (522) may match to an input being false or unknown unlike [0,0], which just does not match to true. Again, [0,1] may not necessarily be treated the same as [0,0] and/or not allowed.

Binary, ternary, and quaternary representation. In one embodiment, a value has three or more states, including the values of "true," "false," and "don't care." In one embodiment, ternary subcondition values are used so that a subcondition is represented as a "known" bit indicating known or unknown by the bit value being true or false respectively, and a second "value" bit that indicates true or false, which is only interpreted as such if the "known" bit is set to true.

A quaternary representation using two bits to represent a ternary value is referred to herein as [a, b] wherein a is whether a state is known (0=unknown, 1=known) and b is a value associated with the state (0=false, 1=true). With this convention, an interpretation of [0,1] that is allowable is that an associated subcondition is "not known to be true." Compare [0,0], which may correspond to the state of unknown, with [0,1], which may be interpreted as "not known to be true" (An alternate convention may be that [0,0] is "not known to be false".) Completing the possibilities, a [1,0] may correspond to be "false" and [1,1] may correspond to be "true" . . . " Note that a [0,1] subcondition may match to an input that is false or unknown, and is unlike [0,0], which does not match any input to true. Thus [0,1] may not necessarily be treated the same as [0,0] and/or may not be allowed in an internal and/or consistent representation.

In one embodiment, a value has two states that allow for different matching behavior for different columns of the table. For a value with binary states, in many applications an object has a symptom or else the clients "don't care," for example an object representing isOverheating (that is, whether a unit is overheating). A "true" for isOverheating indicates a symptom for a particular issue, but there may be many root causes that are not related to whether the unit overheats and is thus "don't Care". Recognizing this, an alternative approach is to have two values per entry rather than three, corresponding to "true" and "don't care." A corresponding match operator output table is:

|  | Table Entry | |
| --- | --- | --- |
| Input | "don't care" | "true" |
| "don't care" | match | no-match |
| "true" | match | match |

This reduces the number of bits required per entry from two bits for a ternary representation to one bit for binary representation, as is thus half as expensive in memory.

There are cases in which there is a need to match on both an entity having a symptom S1 as well in a separate rule/root cause, not having a symptom, such as S1 is false. For this case, an extra symptom S2 may be explicitly introduced that corresponds to the negation of S1, for example a symptom S1 may be lossOfPower and S2 may be hasPower. Then, a row that requires lossOfPower may have the corresponding table entry for symptom S1 set to "true" and S2 set to "don't care." Conversely, a row that requires hasPower may have that corresponding table entry for S2 set to "true" and the S1 entry set to "don't care." Thus, if for example ten percent of the symptoms require negation, a 1-bit approach would still be less expensive in space than the 2-bit approach, that is, an extra 10 percent space but not 100 percent more.

In one embodiment, a combination of S1 and S2 both being true may correspond to "unknown." That is, if the input sets both S1 and S2 then the symptom is treated as "unknown." Representing a state as "unknown" may be more useful in applications than a "not known to be true" interpretation of a fourth value. There is no change or extension to the above matching for this "unknown" support to work. The S1 and S2 entries in a row both specify true, and the input specifies these entries as true as well, so it matches on "unknown."

There are also symptoms that are effectively a discrete enumeration of values, such as very cold, cold, cool, normal, warm, hot, and very hot. These seven values may be represented in three bits in a normal binary representation. However, with the above "true"/"don't care" binary approach, one would need six symptoms for the positive and the negation as separate symptoms for each bit. In particular, the above 7 enumerations can be represented in 3-bits using a normal Boolean representation, e.g. 001 could designate "very cold". However, because the true/don't care embodiment does not explicitly handle false, another 3 bits or symptoms are required are required to specify false, i.e. 0. Therefore, the 001 encoding for "very cold" would be indicated the six symptoms [X,X,1,1,1,X] here "X" designates "don't care" and the first 3 entries correspond to true or 1 values and the second 3 entries correspond to the false or 0 entries. Alternately, seven separate symptoms for a "one-hot" representation of these seven values may be used, where the "one-hot" representation is referred to herein as a group of bits wherein legal combinations of values are only those with a single "true" bit and all the others not "true".

In one embodiment, a specific set of columns used by symptoms representing such an enumeration of multiple symptom values is used. In this case, specific columns are designated as being matched as "true"/"false," as opposed to "true"/"don't care" to represent the enumeration in three columns, rather than six or seven. There is still a need for a "don't care" value so that a row that does not care about the value of this enumeration symptom may indicate this. Thus, the designation of a column value width is allowed and one value reserved to indicate "don't care," for example, all zeros. In this case, a logical column width of three bits may be designated so [0,0,0] may correspond to "don't care", while the remaining seven combinations of values represent the seven different symptom states respectively." Therefore, this enumeration may be represented in three bits, yet still allows "don't care" to be specified in rows that do not care about the enumeration symptom.

Therefore, this additional extension allows the table designation of logical column width and treating the all zeros case as "don't care." Then, the columns corresponding to isOverheating or S1, S2 may be tagged as one-bit width whereas the columns corresponding to the above enumeration would be tagged as one logical column of three bits.

In one embodiment, an efficient representation of column width is having a bit per column that is set if the next column is also part of a logical column/entry spanning multiple columns. Equivalently, the bit may indicate a continuation of the previous column. Thus, the columns corresponding to the enumeration may be tagged as [1,1,0], wherein the last bit indicates that there is no continuation beyond the third column to indicate three-bit columns that form one logical column/entry.

Generally, the table may designate column widths as well as the matching behavior for a logical column. As an example of this more general case, the table may designate a logical column as being five bits wide and the matching behavior being a test for "greater than." That is, the input may match on this entry if its value in these five bits was a binary value that was greater than the value in the table entry, except treating the table entry as "don't care" if it is zero or as "unknown" if it is all ones. As another example of specified matching behavior, it may designate the matching behavior as the logical OR of the input across these columns. By having one bit in the logical column that indicates whether the symptom is relevant to this row and excluding that from the OR, the all zeros value in a table entry may be treated as "don't care."

In one embodiment, hardware instructions such as the "ANDN" or logical AND NOT instruction in the Intel and AMD instruction set may be used with a binary representation. Hardware instructions are generally faster to execute and more efficient to program than their software counterparts. The ANDN instruction performs a bitwise logical AND with an inverted first operand and a second operand, for example, with the result of mismatch for two operands inBlock and tableBlock as follows:

mismatch=~inBlock & tableBlock with corresponding output table:

|  | tableBlock | |
| --- | --- | --- |
| inBlock | "don't care" = 0 | "true" = 1 |
| "don't care" = 0 | mismatch = 0 | mismatch = 1 |
| "true" = 1 | mismatch = 0 | mismatch = 0 | and thus if mismatch is the complement of match,

|  | tableBlock | |
| --- | --- | --- |
| inBlock | "don't care" = 0 | "true" = 1 |
| "don't care" = 0 | match | mismatch |
| "true" = 1 | match | match |

Figure 5C:
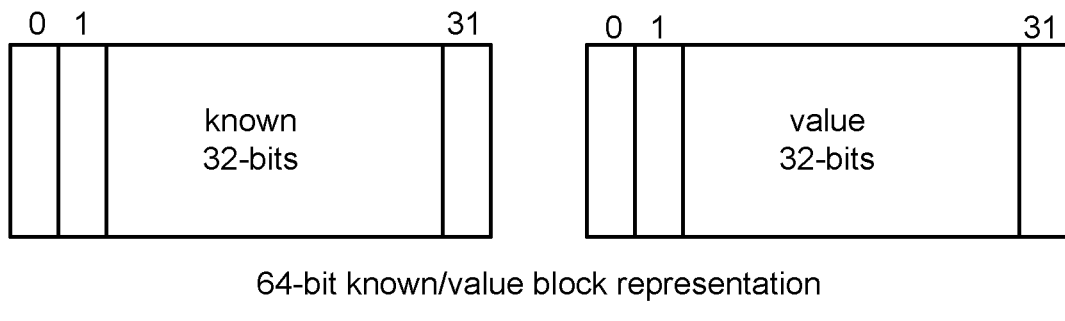
FIG. 5C is an illustration of an example of a 64-bit block representation of known and value bits.

FIG. 5C is an illustration of an example of a 64-bit block representation of known and value bits. In one embodiment, a fault scenario is represented as blocks of bits that are partitioned into a sequence of "known" bits and a sequence of value bits. For example as shown in FIG. 5C, an implementation uses 64-bit blocks, wherein the first 32 bits are "known" bits and the second 32-bits are value bits. Referring to FIG. 5C, if the i-th known bit is 1, the i-th value bit indicates if the corresponding symptom is true or false; otherwise the actual value is not known and the i-th value bit is not meaningful. This embodiment allows efficient determination of the "known" bits in a block. It also means that a block need not be stored if all the symptoms in a block are unknown or "don't care." That is, absence of an explicit storage of a block is interpreted as that block containing only "don't care" values.

Figure 5D:
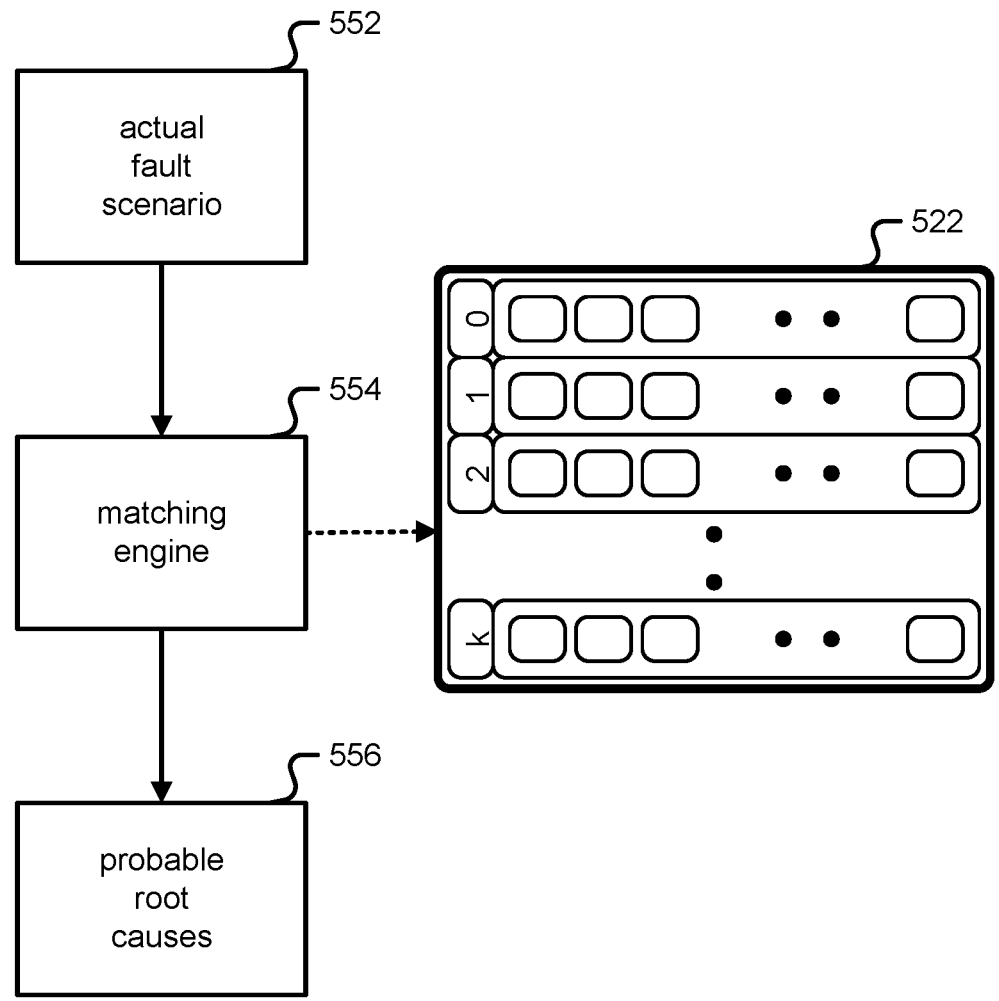
FIG. 5D is an illustration of an example of a root cause analysis technique.

Root Cause Analysis. FIG. 5D is an illustration of an example of a root cause analysis technique. Actual root causes associated with a given actual fault scenario (552) are determined by using a matching engine (554) to match the given actual fault scenario against each row in the RCT (522), and indicating the ones that match as probable root causes. That is, if a fault scenario matches a row such that each entry matches by the above match(a,b) operator, the root cause associated with that row is output as a probable root cause (556) associated with this symptom, as shown in FIG. 5D.

This matching is essentially "ternary matching" but unlike the ternary matching provided by a ternary content-addressable memory (T-CAM), the input fault scenario is also ternary. A T-CAM may however be used as part of an efficient/hardware system of matching. There may be multiple simultaneous root cause failures in a monitored system. Therefore, it is possible that the matching matches multiple rows in the RCT, one per root cause. For example, a motor may fail at the same time that a temperature sensor has failed by indicating completely unrealistic readings. There may be multiple rows that map to the same root cause. This handles the case in which a root cause failure may be indicated by different sets of symptoms.

In one embodiment, the row representation does not explicitly store "don't care" entries. That is, the absence of an explicit designation or representation of an i-th symptom is interpreted as "don't care" for the i-th symptom. In one embodiment, symptoms are aggregated into blocks that are associated with logical units or components of a monitored system. For example, an embodiment may use the 64-bit block of known/value bits described earlier. Thus, if a component is not relevant to a particular root cause, the entire block need not be stored. Each row may then require a relatively small amount of storage. Typically, most rows are relatively sparse because only a small subset of symptoms is relevant to a particular fault so only a small percentage of that row is actually stored, with the rest by default being "don't care."

The representation of arbitrary fault criteria is achieved by using multiple symptoms. For example, one root cause is evidenced by a temperature being very high, yet another is evidenced by it being high, and another evidenced by it being slightly high. That is, there may be a symptom entry in each row for each of these levels.

A key element is indicating the symptoms that are known to be false as a symptom, that is no fault, as well as what is known to be true, that is a fault is present, while still allowing for unknown or "don't care." The false case effectively filters out symptoms that are due to another reason, for example the compressor is not working, but actually there is no power, which is the root cause. Thus, a subsystem SSi that is dependent on a number of other subsystems may need to have all these other systems known to be working before a fault in subsystem SSi may be reliably identified as a root cause.

In one embodiment, the system may record if any symptoms changed in an actual fault scenario since its last matching and only re-match the actual fault scenario to the RCT (522) if so. This check avoids the overhead of re-matching when there is no change to the actual fault scenario.

In one embodiment, the frequency of re-matching is configurable according to application requirements. For example, ARCA matching may be configured to be performed every 30 minutes in a refrigeration system to minimize the cost of the matching because a fault does not result in immediate problems and the resulting delay in detecting a fault does not significantly impact the meantime to repair. This low rate of matching assumes that a fault that is transient enough to appear and then disappear before the matching takes place, and thus is not present in the actual fault scenario at the time of the matching is not critical to detect.

Figure 5E:
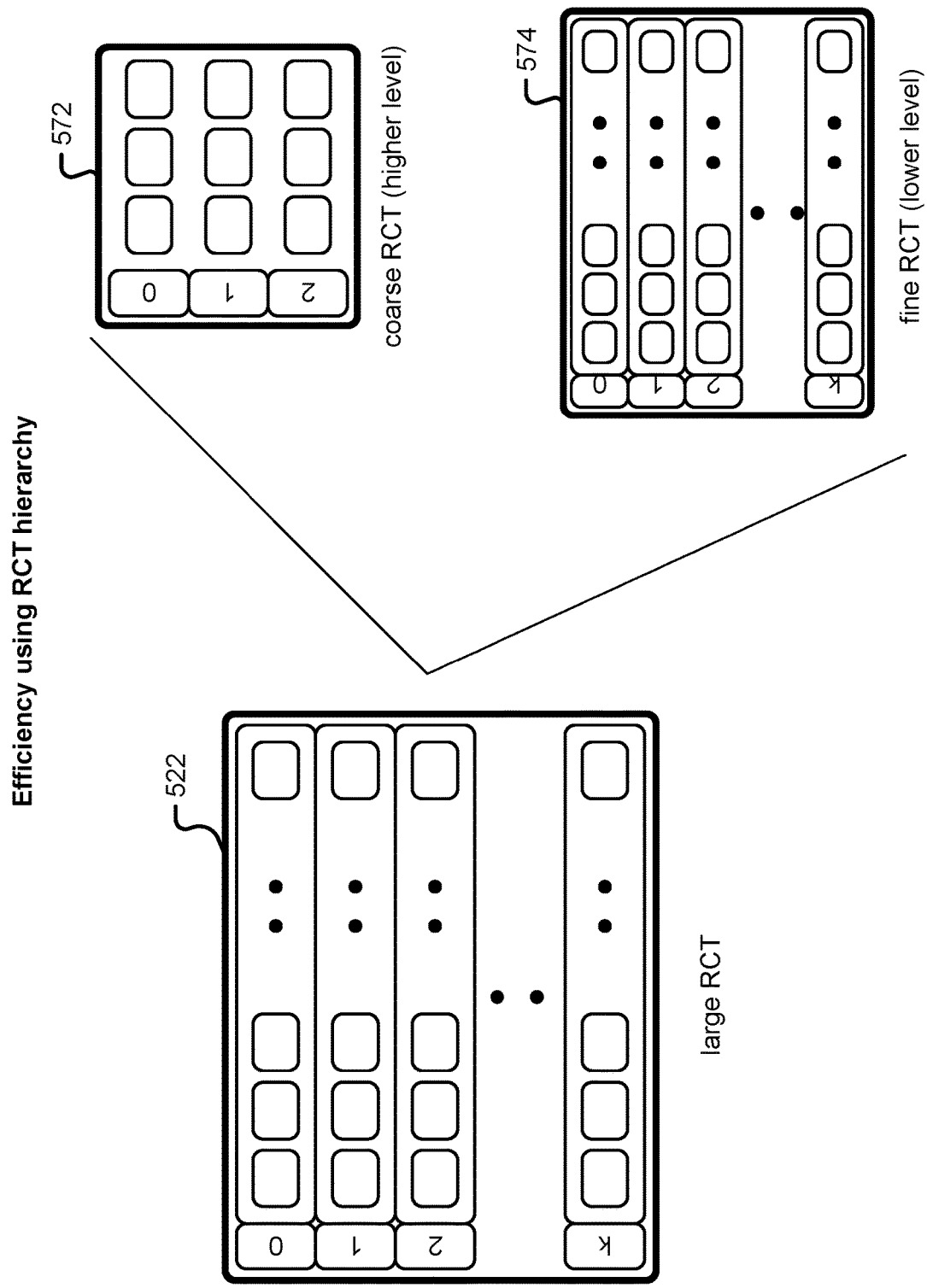
FIG. 5E is an illustration of an example of an RCT Hierarchy.

RCT Hierarchy. FIG. 5E is an illustration of an example of an RCT Hierarchy. In one embodiment, there may be a hierarchy of RCTs corresponding to different levels of root cause analysis. For example, a refrigeration system RCT (522) may be partitioned such that it has a top-level RCT (572) that "root causes" the high-level reason that the system is not performing well, which could be one of: 1) not maintaining the desired temperature, and 2) consuming excessive energy. Once this top-level RCT (572) indicates one of these causes, a next level of monitoring and corresponding RCT (574) may be automatically deployed, depending on the specific cause, to provide a more specific root cause for the top-level root cause. For example, if the top-level root cause for not performing well is excessive energy consumption, additional telemetry and analysis can be deployed to detect the symptoms of low coolant, icing on the coolant coils, supercycling of the compressor, failure of the current sensor, and other possible root causes of the excessive energy consumption. This next level root cause may be sufficient to indicate the necessary repair to the system. Alternatively, a next level of RCT (574) and processing can be automatically dispatched based on the root cause determined at this second level.

This hierarchical processing may reduce the resources consumed by root cause analysis in the case in which the system is operating normally. It also may reduce the resources required to root cause a specific failure if the next level of root cause analysis only needs to handle a subset of possible symptoms based on the indication of the root cause at the higher level. For example, using the above case of a refrigeration system, knowing that the problem with the system is excessive power consumption, the next level root cause analysis processing that is actually deployed may require a smaller RCT (574) and less telemetry and processing compared to this level of root cause analysis that is configured to detect both failure to maintain configured temperature as well as excessive power consumption. Alternately, if both top-level symptoms are arising, there may be no such savings. However, it is feasible to run the two instances of this detailed root cause analysis in parallel as separate processes, which is time efficient.

Generally, the root cause analysis matching may be performed in parallel by partitioning the RCT across multiple parallel threads and collecting the output of each. Because the matching does not modify the actual fault scenario or the RCT and because the matching is order-independent across the rows, the only synchronization required between the threads is on the output to the aggregated root cause set.

Multi-layer, partitioning, and this hierarchal approach reduces the size of the RCT significantly. For example, in a network application, if a higher-level RCT such as basic connectivity only considers four symptoms per node of a network rather than 256, the RCT may be reduced in size by a factor of almost 64. The size may be further reduced by only having coarse-grained root causes in the basic RCT. For instead, a large number of specific problems for a link may be handled at this level by a simple "link-problem" as the root cause, which when identified may cause the dispatch of a more detailed ARCA using the full set of possible specific link issues.

Besides reducing the size of the RCT that needs to be actively accessed in the common case in which there are no faults, this smaller RCT is more efficient to process. Also, with sufficient reduction in size, the fault scenario vector may potentially fit into a hardware T-CAM so that matching may be done in hardware. In one embodiment, where there are multiple similar independent units to root cause, such as with multiple roof-top-units (RTU) in the case of an HVAC application, a single RTU RCT may be used to pass a fault scenario vector for each separate RTU into the T-CAM in sequence, to detect faults in each RTU.

A benefit of such a hierarchical approach is that the basic ARCA is expected to be the common case, namely when the equipment is performing correctly, so the T-CAM may be very efficiently handling the common case, and the detailed ARCA may be reserved for when there is actually a problem. Another benefit is that the more basic ARCA allowed by the hierarchical approach may mean that less telemetry is being collected when there are no faults, which again may be the common case. Thus, a hardware implementation, for example using a T-CAM or equivalent, which may currently be realized using SRAM, is practical and attractive in some applications.

Returning to automated navigation of lane-structured dynamic environments, each lane subcondition is realized as a "symptom" of the ternary fault representation techniques described above, and each lane maneuver corresponds to a "root cause".

A rule set is compiled into a representation that a rule engine can efficiently execute. For example, the rule conditions for the rule set can be compiled into a code realization or a table with a column per observable subcondition and each row associated with a rule, and thus maneuver, similar to what was discussed earlier in FIG. 5B. The entry in a given row (524), say row R, and a given column (527), say column C, is set to that corresponding to the subcondition C in the condition associated with rule R. Then, the rule engine can periodically match the updated computed or observed subconditions against the table using the ternary fault representation techniques described above to determine the one or more maneuvers to perform.

By using an efficient matching mechanism, possibly including specialized hardware support like the TCAM, the matching may be performed in the order of a subsecond period, allowing new maneuvers to be triggered very quickly in response to dynamic events, and/or providing fast response times to dynamic events.

Automatic Generation of an Efficient Rule Set Implementation. Broadening the discussion to how to compile the rules into an efficient rule condition evaluation mechanism, automatic generation of a rule set implementation is based on and derived from a set of key observations. An example of an AV recognizing a stop sign is one example detailed below.

A first key observation is that rules may be divided into two categories as referred to herein:
 const rules—those that do not generate any external output or external action when triggered; and
 non-const rules—those that directly cause external output or an external action.

The terms "const" and "non-const" come from C++ nomenclature, referring to whether the rule logically changes state, including external state, or not.

In traditional RBS terminology and implementation, there is an internal working memory. The actions that a rule may take include adding, removing or modifying a fact in this working memory, as well as possibly performing some external action/output. A const rule is a rule that only acts on this working memory. A non-const rule takes some action that is visible outside the rule engine. If a rule set includes a rule that both updates internal working memory as well as generates an external action or output, it may be split into two rules, each with the same condition, with one that does the former, and thus is "const", and the other than just performs the external action, with some indication to the conflict resolution to perform both rules when they match.

A second key observation is that a const rule may be viewed as a logical implication. In particular, a rule is structured as "condition→action". For a const rule the action is simply adding a fact F to the working memory. Thus, the const rule may be regarded as "condition→F". That is, the truth of this condition implies the condition F being true, where the condition F is a Boolean expression that corresponds to the "fact" when it is true. As referred to herein, the term "imply" and "implication" is used in the logical sense that A implies B means that if A is true then B is true.

A third key observation is that the set of "rule conditions" associated with the rule set is the difficult aspect to maintain and to evaluate in execution. This is because the rule conditions may evolve to be quite complex expressions yet the actions are typically quite limited and relatively simple and are often specified as a separate procedure that performs the action. Using the example from above to illustrate, there are a limited number of actions that a vehicle may perform, such as braking, accelerating, and/or turning. It is the condition, such as that outlined previously for proceeding at an intersection, that is complex.

As referred to herein, the term "condition" is conventionally used when it is a condition expression, which when true indicates that the condition is present. The terms "condition" and "subcondition" are used herein in the same way, namely both for the Boolean expression as well as for the state in which this Boolean expression is true.

A fourth key observation is that a rule set may be rewritten to an equivalent rule set such that each rule condition is a conjunction of Boolean subconditions. In particular, if an original rule condition has at the top-level a disjunction, this may be rewritten as multiple rules, one for each subcondition in the disjunction. For instance, if the rule is:

(SC0∥ SC1∥ SC2)→action3;

it may be rewritten as three rules, namely:

SC0→action3;
SC1→action3;
SC2→action3;

Thus, if any of these three original subconditions are true, the action is triggered.

Other conventional Boolean transformations allow each rule condition in the rewritten rule set to be a conjunction. That is, a rule condition may be rewritten as a conjunction of subconditions, for instance:

(SC0 && SC1 && SC2)→action14;

indicating if subconditions SC0, SC1 and SC2 are all true, the scenario with these subconditions/features is the case so the system may perform the action labeled action14.

A fifth key observation is that a rule condition is trying to achieve a matching of facts or inputs to a given scenario in an application-specific model. For instance, in a particular application domain, such as a self-driving vehicle, the rule condition may correspond to seeing a stop sign, and the subconditions are: SC0-red in color, SC1-octagonal shape and SC2-inscribed with "STOP". Thus, the key focus is on specifying each rule condition as recognizing a scenario or scenarios in the application domain that calls for performing the associated action. Stated another way, a non-const rule may be viewed as logically inferring from its rule condition that its associated action is appropriate.

As referred to herein, the term "model" refers to the computer science model which is an object-oriented representation of a system or entity. This usage of "model" distinguishes over using the same term to refer to a mathematical equation-based specification of a system. In particular, object models that specify elements and their relationships are discussed. As used herein, the rule set maintainer such as a system administrator or programmer may consider adding an additional arbitrary subcondition SC3, that is a Boolean expression. However, in reality, the only subcondition(s) that may make sense to specify are one(s) that aid in matching a given scenario. In conventional terminology, as used with ML and image interpretation, SC0, SC1, SC2 and SC3 are features or represent features of this scenario, used to classify this scenario. They represent a feature in the sense that the subcondition specifies that a given expression in terms of sensor inputs is true of the scenario. For example, the subcondition may be "isApproachingIntersection".

A subcondition SC3 may be important to add to a rule condition RC0 if this rule condition is ambiguous with respect to another rule. For otherwise, the rule condition RC0 may be under-specified. On the other hand, adding SC3 to RC0 is unnecessary and increases rule condition evaluation cost if RC0 is not ambiguous relative to other rule conditions. That is, adding the SC3 to the rule condition may make it over-specified.

A sixth key observation is that this matching on features or so-called feature classification may be transformed into the problem of root cause analysis by treating features as symptoms and by considering the classes into which features are classified as root causes, that is the root cause for the image that is detected is an object in the image of the corresponding classification. For example, the root cause of the symptoms/features of red, octagonal and inscribed with "STOP" is the object in the image being a stop sign.

More generally, an RBS may be transformed into the problem of root cause analysis by treating:

each subcondition of a non-const rule as a symptom;
the const rules as symptom propagation. That is, if condition→fact is a const rule, then the "symptom" corresponding to this condition propagates to the "fact", which is also a symptom, that is specified by the rule; and
the root cause as a label that is separately mapped to an action to be performed.

Conversely, root cause analysis may be regarded as feature classification in which the features are symptoms and the output classification identifies a particular root cause or root causes. As described above, root cause analysis may also be viewed as a rule-based system in which each action of a non-const rule is "output this root cause" and each const rule is treated as specifying symptom propagation.

A rule set RS, transformed as above, may be embedded in an object model by:

for each element mentioned in a subcondition in RS, introducing an element and the corresponding element type, if not already defined, for example a network switch element;
for each attribute mentioned in a subcondition in RS, introducing this attribute in the corresponding element type, if not already present. This includes attributes that correspond to relationships between objects. In one embodiment, this is done by manually and/or automatically defining and/or modifying the object-oriented model;
for each non-const rule, introducing a corresponding symbolic subcondition in the appropriate element type that is labelled with an indication of the corresponding action, and specified to imply the subconditions that constitute the conjunction which defines this rule condition. Each subcondition is defined in the most relevant element type, that is namely the one in which this subcondition is true of. For example, specifying in a network model, the condition of "cableBreak" in the context of a Link element type. Another example may be a symbolic subcondition of "seeing a stop sign" introducing implications such as "red", "octagonal" and words "STOP";
for each const rule, specifying the subcondition implications specified by this const rule. In particular, if this rule is "A→B", specifying implication of subcondition A in its element type to B in either the same element type or a separate element type to which this element type is related in some way; and
specifying subconditions that may be determined directly from element attributes as an observable.

FIG. 6 is an illustration of an embodiment of a simple model of a computer network. The model of FIG. 6 is expressed in a object-oriented programming language syntax, illustrating this embedding of rules.

As shown in FIG. 6, there is an element type for each of: Unilink (602), Link (604), Interface (606), and Switch (608), corresponding to the typical components at the physical layer of a computer network. Each element type has a subcondition specified inside its scope. For instance, the Link type (604) has the subcondition named cableBroken. This subcondition also has an actionLabel specified, making it the rule condition for the rule associated with this actionLabel.

This subcondition also includes the statement component::lossOfSignal; meaning that this subcondition implies the subcondition Unilink::lossOfSignal in each Unilink component of Link. In general, in this syntax, the implication statement indicates the relationship followed by the subcondition inferred in the receiving element from this subcondition. The relationship is an attribute of the element, such as, in this example, the Link::component attribute which is an array of Unilink objects.

The Interface element (606) similarly contains a lossOfSignalIn subcondition that is implied by this earlier statement, and then in turn implies this subcondition to its parent Switch (608) as the lossOfSignalIn. The "$" symbol indicates a parameter that is replaced by the name of the element. So, for example, if this interface is eth3, the $ is replaced by eth3 as part of this inference. The lossOfSignalIn subcondition in Switch is indicated as observableBy an expression namely signalIn==0. This means that this subcondition may be detected by or equal to an expression in terms of attributes of the type. These attributes are typically set by a monitoring system that is receiving this information as real-time telemetry from the switch. A variable or attribute that appears in an observable subcondition and that may change is referred to herein as an input attribute.

In one embodiment, implication may be instead be specified in the form of inference. For instance,

```
signalLoss : Subcondition {
    <= modem::lossOfSignal;
}
``` specifies that the signalLoss subcondition may be inferred from a lossOfSignal subcondition in the modem that this current element type depends on. This "infer" form is equivalent to an implication specified from the modem to the current element in this example. However, inference is useful in specification because an element is not typically specified with the knowledge of all the elements that depend on it. In this case, the dependent element may specify inference, thereby avoiding this logical compromise in the specification. For example, an invertible relationship may be one between server to client to indicate a propagation of a problem from server to all its clients. Thus, if a client is detecting a problem with the server, it may also be inferred the server has a problem.

Note that the attribute Interface::connectedToBy is indicated as an inverse to the Unilink::connectedTo relationship. In general, every relationship across which a subcondition implication is specified is required to have an inverse relationship. In the case of certain standard relationships, such as component, the inverse is implicit or known, namely parent in this case.

Figure 7:
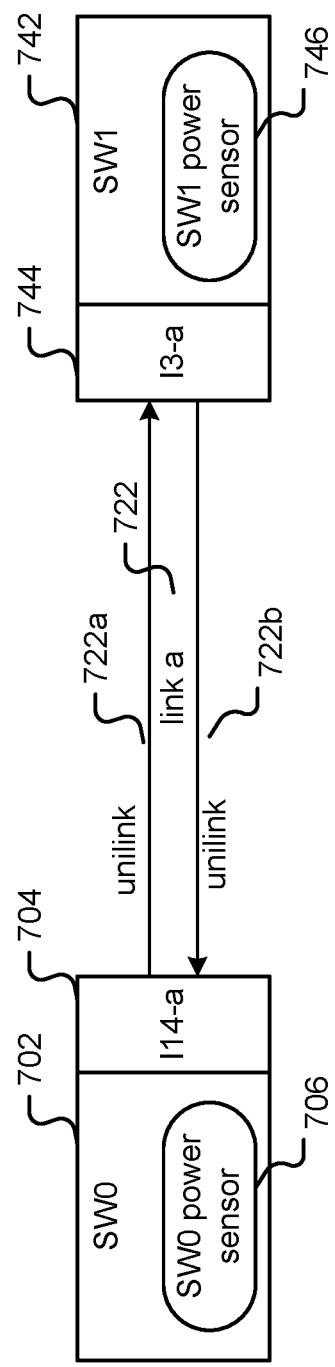
FIG. 7 is an illustration of an embodiment of an instance of a network created with element types.

FIG. 7 is an illustration of an embodiment of an instance of a network created with element types. For example, the element types of FIG. 6 are shown in FIG. 7. In FIG. 7, there are two switches, switch0/SW0 (702) and switch1/SW1 (742), each an instance of the Switch type described earlier. Each switch SW0 (702) and SW1 (742) is shown with one component interface, I14-s/eth14 (704) and I3-a/eth3 (744) respectively, and a power sensor for the switch, SW0 (706) and SW1 (746), respectively. Not shown in FIG. 7 may also be power sensors for the network interfaces (704), (744) if they are discretely powered.

In a real network, there may typically be multiple interfaces per switch and potentially many more switches. The Link (722) between these two connected interfaces is modeled as two component unidirectional links (722*a*, (722*b*), each an instance of Unilink. This level of detail allows the directionality of implication to be specified. It also allows for modeling faults such as one direction of a link failing while the other direction continues to function.

This simple model illustrates how a rule condition may be specified in an element type such as a Link (722) on which there may be no telemetry because there are no sensors on a link (722). Nevertheless, the associated subcondition may imply subconditions in intermediate elements such as unidirectional links and then to the connected interfaces to their parent switch, at which point they imply subconditions that are observable.

In one embodiment, the input rule set is specified in a model as illustrated in FIG. 6. Thus, the partitioning into const and non-const rules is just a matter of recognizing that each const rule is specified as an implication from one subcondition to one or more other subconditions for example in the same element or over a relationship to another element, and each non-const rule is specified as the rule condition resulting from the conjunction of the observable subconditions reached by implication from the subcondition labelled with its action.

In the following, the rule set is assumed as either input as embedded in a model as above or else is automatically transformed and embedded into this model as part of the input processing using the algorithm described herein. As referred to herein, "embedding" means specified inside the object model from a physical placement standpoint as shown in FIG. 6. For example, with a unilink element, a subcondition is lossOfSignal, implying that a loss of signal input to an element it connectsTo points at an interface, as shown in the object model in FIG. 6. The object-oriented model in FIG. 6 builds up context and maintains relationships between objects as important.

Model-based Generation Based on Root Cause Analysis Techniques. Building on the observation of relationship to automatic root cause analysis, there are traditional techniques to automatically generate a root cause table (RCT) from a high-level model of elements, relationships between these elements, symptoms and symptom propagation across these relationships from a root cause to observable symptoms. This approach may also be used with suitable extension to generate a ternary RCT as described above. The ternary matching is important to avoid having to specify subconditions for every input attribute.

In one embodiment, a model is similar to that illustrated in FIG. 6, and similar to the RCT reference instead of a conventional rule set. This model captures the key element or objects of the application domain and their subconditions, also known as features and/or symptoms. For example, in a self-driving application, the model may include vehicles, roads, intersections, driving signs, pedestrians, and so on.

The subconditions are expressed in terms of actual inputs to the model such as vehicle-stopped or computed from inputs such as vehicle-over-speedlimit, computed based on the speed limit for the given region of travel and the speed of the vehicle, determined by wheel rotational velocity and possibly positional information. The actions are specified in the model as illustrated in FIG. 6.

In one embodiment, a compiler module automatically translates this model, as an intermediate stage into a collection of directed acyclic graphs (DAGs), each rooted at a subcondition that is the rule condition for a non-const rule. The leaves of each DAG are subconditions expressed in terms of input attributes.

Figure 8A:
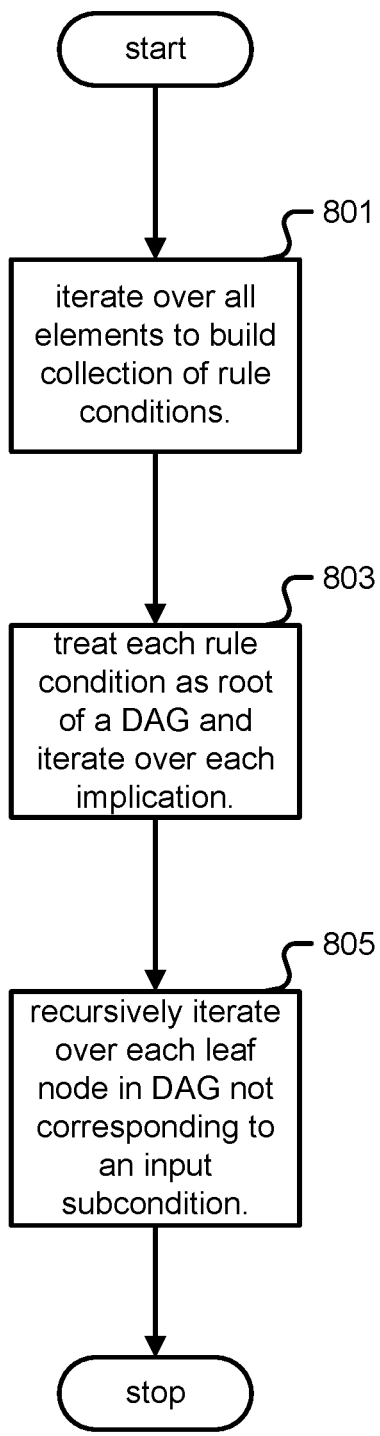
FIG. 8A is an illustration of an embodiment of a process for performing automatic translation.

FIG. 8A is an illustration of an embodiment of a process for performing automatic translation. In step (801), all elements in the model are iterated over to build a collection of rule conditions. In step (803), for each rule condition RC in this collection, the rule condition RC is treated as the root of a DAG and all the implications associated with this rule condition RC are iterated over, adding each link and edge in the DAG for each with the source end corresponding to the rule condition and the destination end corresponding to the target or right-hand side of the implication. In step (805), each leaf node in the DAG that does not correspond to an input subcondition is recursively iterated over, including adding additional nodes and links as in step (803), and terminating when each leaf node corresponds to an input subcondition, and reporting an error if a leaf node does not have an implication that corresponds to an input attribute and does not correspond itself to an input attribute.

Figure 8B:
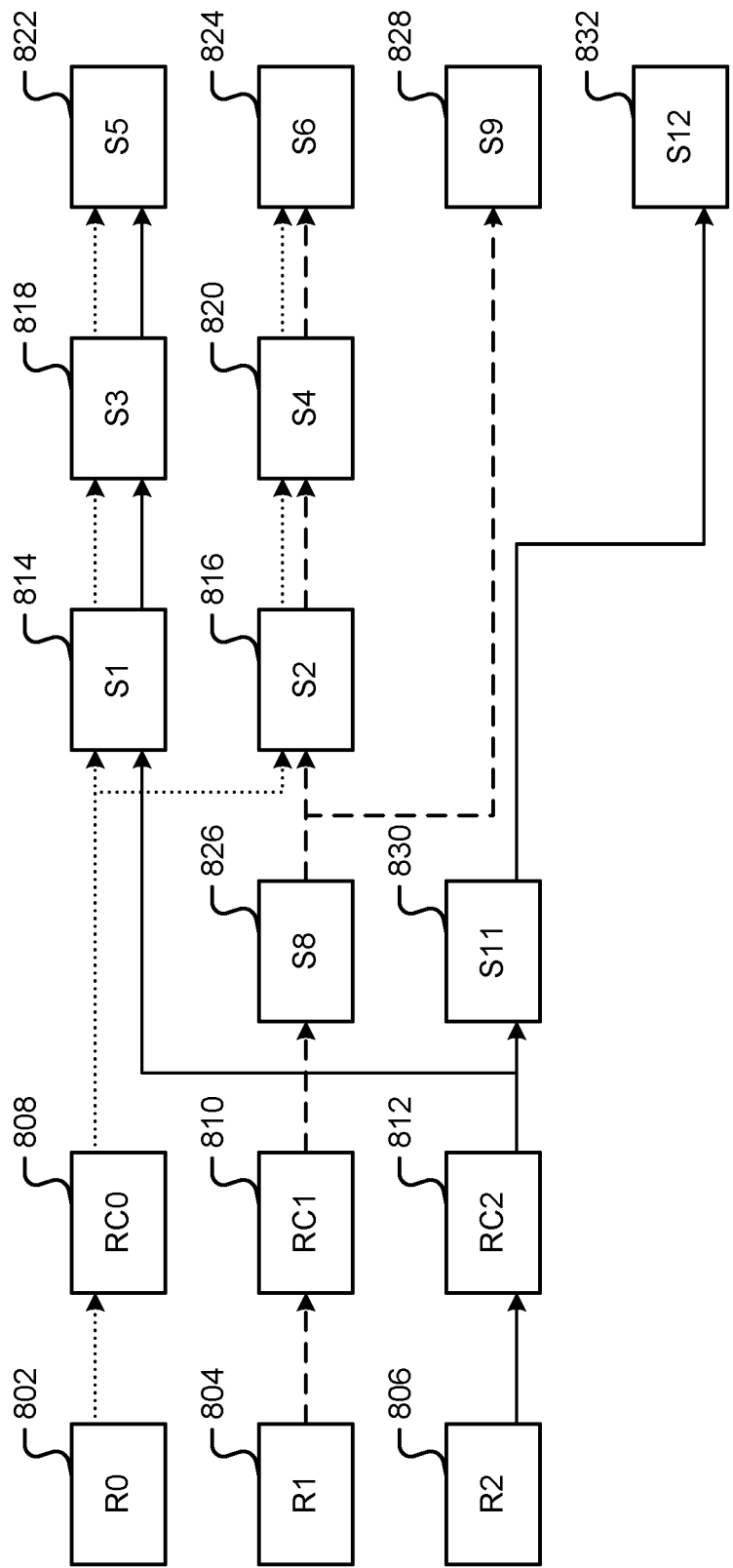
FIG. 8B is an illustration of a collection of DAGs for a network example.

FIG. 8B is an illustration of a collection of DAGs for a network example. In FIG. 8B, there are three rules R0 (802), R1 (804), and R2 (806). Each rule has an associated rule condition RC0 (808), RC1 (810), and RC2 (812). Each rule condition implies the truth of one or more subconditions that are the components of this condition as a conjunction. For example, RC0 (808) implies the truth of S1 (814) and S2 (816). S1 (814) implies the truth of subcondition S3 (818) which implies the truth of subcondition S5 (822). S2 (816) implies the truth of subcondition S4 (820) which implies the truth of subcondition S6 (824). Similarly, RC1 (810) implies the truth of S8 (826), which in turn implies the truth of both S2 (816) and S9 (828). Similarly, RC2 (812) implies the truth of both S1 (814) and S11 (830). S11 (830) implies the truth of S12 (832). Put another way, DAGs are derived to reflect implications.

In one embodiment, this processing is an adaptation of other works such as ARCA works, by replacing "symptom" with "subcondition" and replacing the root cause designation with an action designation. Considering the self-driving application again, the rule "remain stopped on entering intersection at a green light because of blocked" has a rule condition in the element AV (for autonomous vehicle) that implies in the traffic light detector the subcondition "isGreen" and implies in the intersection detector the subcondition "isEntering", and implies in the obstacle detector the subcondition "IsBlocked". The rule condition is then generated as the conjunction of these the subconditions being true. In C++-like pseudo-code, the generated rule may be specified as:

```
                    if((trafficLightDetector-
>color( )==green) &&
    (intersectionDetector->position( )==entering)&&
```

```
    (obstacleDector( )->state( )==blocked))    {
        remainStoppedEnteringGreenBlockedIntersection( );
    }
```

This generation is based on the observation that a row of a RCT is specifying the root cause as the conjunction of observable/observable symptoms, so by the above translation, the condition for a rule is the conjunction of the corresponding input subconditions. Thus, Table 1 is an RCT representing the DAGs of FIG. 8B:

TABLE 1

Root Cause Table for Example in FIG. 8B.

| Root Cause | Symptom S5 | Symptom S6 | Symptom S9 | Symptom S12 |
| --- | --- | --- | --- | --- |
| RC0 | 1 | 1 | x | x |
| RC1 | x | 1 | 1 | x |
| RC2 | 1 | x | x | 1 |

Separating Actions from Condition Evaluation. In one embodiment, the action for a non-const rule is specified indirectly by specifying a scenario label or an action label in the model in place of the root cause name, and providing a separate mapping of scenario label to action. In this embodiment, using the above example again, the rule may be:

```
            if((trafficLightDetector->color( )==green) &&
                (intersectionDetector->position( )==entering)&&
                (obstacleDetector( )->state( )==blocked))    {
                output("enteringGreenBlockedIntersection");    }
``` so the label is "enteringGreenBlockedIntersection".

After the rule evaluation is performed, the label that is output is matched to the associated action. In this case, the actionMap may map to the action "remainStopped". In C++-like pseudo code, one realization may be:

```
actionObject = actionMap("enteringGreenBlockedIntersection");
actionObject->performAction( );
``` where the "actionObject" is a C++ object that has a virtual function performAction that is overridden in each derived type of this object to perform the desired action.

In this case, the actionMap may map to an object of a derived type that overrides the performAction procedure to perform the action of "remainStopped". This indirection means the matching identifies the scenario with a label, and scenario is mapped to the action. Consequently, the same action implementation may be shared across multiple scenarios. In fact, this example may be refined by having a "comeToStop" action, which may be applied in many different scenarios which do not necessarily involve intersections, traffic lights or blockage. For example, there may be a roadworker holding up a stop indicator prior to some construction that narrows the road to one lane. The same action may be invoked in this scenario as well as many others.

For clarity of explanation, the action mapping is shown as a textual label mapping. However, in internal implementation, the label may be a pointer to the associated action object, so the mapping is essentially just a virtual function call in C++ terminology.

For simplicity of explanation, the performAction function is shown without any parameters. However, in one embodiment, there may be a "scenario" object that is associated with the matched scenario that is passed to the performAction function, that is actionObject→performAction (scenario); where "scenario" is a description of the scenario. For example, the "comeToStop" action needs to be parameterized on the distance to the blockage as well as the speed of the vehicle. This extra information may allow the action procedure to determine whether it needs to brake hard or whether gradual braking is sufficient.

Thus, a compiled result from FIG. 8B includes a table that is matched against to perform rule condition evaluation and/or generated code that explicitly evaluates the rule conditions. In one embodiment, the generated code is parameterized in terms of the elements and inputs involved in the rule conditions. Thus a compiled result may be a table which tends to an automatic poll driven, memory intensive operation, say being polled every five minutes. A complied result may also or alternately be generated code which tends to an interrupt and/or symptom driven codebase that parameterizes code via code generation, and may be triggered by symptoms, for example.

To perform conflict resolution, as is traditionally specified in an RBS, one embodiment creates a matchset of matched action labels as a result of condition evaluation. Then, if there are multiple entries in this set, indicating multiple rules are being triggered, it applies conflict resolution to this set to select the subset of actions to perform. Considerable other references exist on techniques to select actions, including priority, time matched, and based at least in part on probabilities as described herein.

Action Selection based on Probability. A traditional approach, used with Bayesian networks and machine learning, is to associate probabilities with the inputs, and pass these probabilities through a computational network to compute the output with the highest probability. For example, a temperature sensor may be considered over threshold with some probability P and under threshold by the complement probability 1-P, where P reflects the uncertainty that the sensor is not reporting the current temperature.

There are several problems in associating probabilities with inputs.

First, these input probabilities are not known and perhaps not practically knowable, given they may depend on many factors, including the age of the component, the way it was installed and the make/model of the component. This is particularly problematic in ARCA due to reasonably infrequent failure events. For example, it may be infeasible to have data on how frequently a given make and model of temperature sensor fails such that it reports an incorrect temperature crosses the threshold for that set for a particular system, given this event may only be detected by having one or more redundant temperature sensors with which to compare the normal or in-service temperature sensor. That is, it would require a second monitoring device per sensor and record the frequency with which is discrepancy arose, an expensive redundancy not done often in practice.

Second, different inputs are often not completely independent because there may often be a dependence or correlation between different inputs given they are part of the same system under diagnosis. This dependence could be expressed in probabilities as a conditional probability between two inputs. However, such a conditional probability is even more difficult to know, given it involves samples across a pair of elements. Moreover, the actual conditional probability may vary over time and/or space based on various factors, including the actual values of the different sensor values, the age of the system, its mode of operation and so on.

Finally, the output of such systems is generally provided as the root cause with the highest probability, as computed from these input probabilities, and thus is a single root cause, given only one may have the highest probability. In fact, these probabilistic computations may generate a large number of potential diagnoses, and rank them by probability. However, it is not clear how to filter these diagnoses sensibly based on computed probabilities, given the difficulties with using input probabilities mentioned earlier. For instance, if the operator only considers potential root causes with probability greater than 0.7, a reasonable concern is to ask how a user may have confidence that the actual root cause has at least that probability. That is, how may a user reason that this particular threshold is the right one to include the actual root cause without arbitrary numbers or requiring repetition to gain a manual, qualitative intuition for the system.

A manual approach to root cause analysis traditionally uses qualitative evaluation of symptoms and human "common sense" so is not very adaptable to an automated root cause analysis system. Similarly, these manual "by hand" approaches lack a computational framework for dealing with uncertainty, further making them difficult to automate.

An example of a traditional ARCA is DellEMC's SMARTS program, which may apply probabilities on input. It does not appear to generate multiple root cause matches, when it may use the closest match based on Hamming distance. The use of a Hamming distance would typically give only one top match except for ties. Given the use of a Hamming distance as an arbitrary measure, it is not necessarily clear what semantics or value to attach in relativity to the second-closest match, third closest match, and so on.

An efficient automated means to generate a set of likely root cause failures that correspond to the symptoms of the system under diagnosis is shown herein, including by specifying and/or pre-specifying a multiplicity of potential fault scenarios. As referred to herein, a potential fault scenario may correspond to a set of symptoms that are expected when a given fault in the system occurs. As referred to herein, a symptom is an observable value or value range, or value computable from observable values relevant to identifying a fault or counter-indicative to a fault. Unlike SMARTS which may apply probabilities on input, the techniques herein associate probabilities with output, expressed for example as confidence levels. As referred to herein, a confidence level for a potential fault scenario is the probability for the scenario fault in the system given the set of symptoms of the potential fault scenario.

For example, a symptom may be "loss of signal" being reported by a computer network switch on a particular one of its interfaces. When the monitoring of the system detects a set of symptoms from the actual system being monitored, referred to herein as an actual fault scenario, this actual fault scenario is matched against the set of potential fault scenarios, to produce what is referred to herein as a matchset for this actual fault scenario, with a potential fault scenario being a member of a matchset if it is matched to the actual fault scenario.

This matchset may then be refined based on attributes of the matching potential fault scenarios and other information. As referred to herein, attributes include any information and/or relationships related to the matching potential fault scenarios such as relationships between symptoms of matches, identity of matches, and/or confidence levels of matches. The root cause faults associated with the entries in the refined matchset may then be output, constituting the result of the root cause analysis. This root cause analysis may produce a set of potential root causes that likely will include the actual root cause fault or root cause faults.

Network Example—multiple potential fault scenario. An example based on FIG. 7 is a symptom of the current symptoms for a network is "loss of signal" being reported by a computer network switch on a particular one of its interfaces.

The actual fault scenario of a "loss of signal" being reported by SW0 (702) on interface I1-a (704) may match to a fault scenario FS1 corresponding to there being a link failure in link a (722) between switch SW0 (702) and switch SW1 (742). However, the same symptoms may also match to a fault scenario FS2 in which the two interfaces (704), (744) at either end of the link have failed at the same time. It may also match to a fault scenario FS3 corresponding to the link failure in link a (722), but without ancillary symptoms considered, such as the symptoms corresponding to power loss at SW0 sensor (706) and SW1 sensor (746) being known to be false. Consequently, in this example, the matchset consists of FS1, FS2 and FS3. A tabular expression of this is:

| | Metadata | |
| --- | --- | --- |
| Label | Symptoms | Root Cause |
| FS1 | Loss of signal on (704) & no power loss at (706) & no power loss at (746). | Link a (722) failure |
| FS2 | Loss of signal on (704) & no power loss at (706) & no power loss at (746). | Both interfaces (702), (744) failed at same time. |
| FS3 | Loss of signal on (704). | Link a (722) failure |

Subsuming base scenarios by their associated derived scenarios. In one embodiment, an attribute of a potential fault scenario indicates when one potential fault scenario FSa is subsumed by another potential fault scenario FSb. That is, whenever FSb is matched, FSa would also be matched. As referred to herein, FSa is a base scenario and FSb is a derived scenario. In the case that both FSa and FSb are matched, a refinement of the matchset is to remove FSa from the matchset before translating the fault scenarios to their associated root causes.

To illustrate this case, the match refinement step would recognize, continuing the Network Example of FIG. 7, that FS3 is subsumed by FS1 because FS3 is requiring matching only a subset of the symptoms that FS1 is requiring.

| | Metadata | |
| --- | --- | --- |
| Label | Symptoms | Root Cause Identifier |
| FS1 (derived scenario) | Loss of signal on (704) & no power loss at (706) & no power loss at (746). | Link a (722) failure |
| FS2 | Loss of signal on (704) & no power loss at (706) & no power loss at (746). | Both interfaces (702), (744) failed at same time. |
| ~~FS3~~ (base scenario subsumed by FS1) | ~~Loss of signal on (704).~~ | ~~Link a (722) failure~~ |

Another simple example of a base scenario being subsumed by a derived scenario is a medical example:

a potential fault scenario FSm shows a root cause of flu given the symptoms of high body temperature and aches with an 80% confidence level; and a potential fault scenario FSn shows a root cause of flu given the symptoms of high body temperature, aches, and headache with a 90% confidence level.

| | Metadata | | |
| --- | --- | --- | --- |
| Label | Symptoms | Root Cause Identifier | Confidence Level |
| FSm (base scenario) | High body temperature & aches | Flu | 80% |
| FSn (derived scenario) | High body temperature & aches & headache. | Flu | 90% |

Thus, with an actual fault scenario including symptoms of high body temperature, aches, and headache, FSm is recognized as a base scenario subsumed by a derived scenario, FSn, and thus a root cause of flu with a 90% confidence level is output.

| | Metadata | | |
| --- | --- | --- | --- |
| Label | Symptoms | Root Cause Identifier | Confidence Level |
| ~~FSm~~ ~~(base scenario)~~ Subsumed by FSn | ~~aches~~ | ~~Flu~~ | ~~80%~~ |
| FSn (derived scenario) | High body temperature & aches & headache. | Flu | 90% |

Combination of output probabilities. In one embodiment, a refinement may recognize that two potential fault scenarios that are present in the matchset are actually two different set of symptoms for the same root cause, and in fact may both be true, so the output contains that potential root cause, possibly with an associated probability that is a combination of the probabilities of the two potential fault scenarios. For example, FSn may be a potential fault scenario showing a root cause of flu given symptoms of high body temperature, aches, and headache with a 90% confidence level and FSp may be a potential fault scenario showing a root cause of flu given symptoms of runny nose and ear aches with a 5% confidence level.

| | Metadata | | |
| --- | --- | --- | --- |
| Label | Symptoms | Root Cause Identifier | Confidence Level |
| FSn | High body temperature & aches & headache. | Flu | 90% |
| FSp | Runny nose & ear aches. | Flu | 5% |

A patient with symptoms of high body temperature, aches, headache, runny nose, and ear aches may be recognized as a combination with an associated probability being a combination of the 90% confidence level and 5% confidence level. In one embodiment, the confidence levels may be linearly summed.

| | Metadata | | |
|---|---|---|---|
| Label | Symptoms | Root Cause Identifier | Confidence Level |
| FSn | High body temperature & aches & headache. | Flu | 90% |
| FSp | Runny nose & ear aches. | Flu | 5% |
| Combination (FSn, FSp) | High body temperature & aches & headache & runny nose & ear aches. | Flu | 95% |

Alternative explanations. In one embodiment, an attribute of a potential fault scenario indicates when one potential fault scenario FSc is an alternative possibility to another potential fault scenario FSd. Thus, when both FSc and FSd occur in the matchset, the refinement would indicate these as part of a subset of alternative potential root causes for the actual fault scenario, as opposed to indicating the two matches as two separate possible faults and/or indicating the two matches as part of different root cause groups. In an embodiment, the attribute indicating a potential root cause as an alternative can be computed by comparing the symptoms of the two potential root causes. It is an alternative has a subset of the symptoms of the other potential root cause and it is not a base root cause of same, it is an alternative.

For example, using the Network Example of FIG. 7, refinement would indicate FS1 and FS2 as alternatives to each other, given that both scenarios correspond to a common set or subset of symptoms.

| | Metadata | |
|---|---|---|
| Label | Symptoms | Root Cause Identifier |
| FS1 (derived scenario) | Loss of signal on (704) & no power loss at (706) & no power loss at (746). | Link a (722) failure |
| FS2 (alternative explanation to FS1) | Loss of signal on (704) & no power loss at (706) & no power loss at (746). | Both interfaces (702), (744) failed at same time. |

Another simple example of an alternative explanation is a medical example:
 a potential fault scenario FSn shows a root cause of flu given the symptoms of high body temperature, aches, and headache with a 90% confidence level; and
 a potential fault scenario FSq shows a root cause of hayfever given symptoms of high body temperature, aches, and headache with a 3% confidence level;

| | Metadata | | |
|---|---|---|---|
| Label | Symptoms | Root Cause Identifier | Confidence Level |
| FSn | High body temperature & aches & headache. | Flu | 90% |
| FSq | High body temperature & aches & headache. | Hayfever | 3% |

Thus with an actual fault scenario including symptoms of high body temperature, aches, and headache, FSq is recognized as an alternative explanation to FSn.

| | Metadata | | |
|---|---|---|---|
| Label | Symptoms | Root Cause Identifier | Confidence Level |
| FSn | High body temperature & aches & headache. | Flu | 90% |
| FSq (alternative explanation to FSn) | High body temperature & aches & headache. | Hayfever | 3% |

In one embodiment, another attribute of a potential fault scenario is the probability of this fault scenario relative to its associated alternative fault scenarios. To illustrate, using the Network Example of FIG. 7, the probability of FS1 may be 0.95 and the probability of FS2 as an alternative to FS1 may be assigned 0.05. The matchset refinement may then order the associated root causes according to the probabilities associated with each of the alternatives. Thus, in the Network Example of FIG. 7, the refined root cause set may be:

[RC1:0.95, RC2:0.05]

wherein RC1 corresponds to the root cause associated with fault scenario FS1 and RC2 corresponds to the root cause associated with fault scenario FS2. The refinement eliminates a third entry because FS3 is subsumed by FS1.

| | Metadata | | |
|---|---|---|---|
| Label | Symptoms | Root Cause Identifier | Confidence Level |
| FS1 (derived scenario) | Loss of signal on (704) & no power loss at (706) & no power loss at (746). | Link a (722) failure | 95% |
| FS2 (alternative explanation to FS1) | Loss of signal on (704) & no power loss at (706) & no power loss at (746). | Both interfaces (702), (744) failed at same time. | 5% |

Associating probabilities with the potential fault scenarios may be more feasible than the input probabilities approach because each fault scenario represents a situation in which a top-level failure requires remediation. Therefore, operational data may indicate the frequency with which a given root cause occurred compared to that of the alternatives, namely those with the same symptoms. For example, resuming Network Example of FIG. 7, if a broken link a (722) is the actual root cause 95 out of 100 times that the associated symptoms were observed, and only 5 out of those 100 times was it the case that it was actually the two interfaces (704), (744) failing at the same time, recorded operational data provides the basis of weighting and ordering these two alternative root causes with these probabilities.

Therefore, remedial action that first treats the output result as detecting a broken link a (722) would immediately address the actual root cause failure most of the time, and only 5 percent of the time, would require going to the alternative fault remedial action. In some cases, such as the case of simultaneous failure of two interfaces (704), (744), a user may estimate the probability based mean time to repair for an interface and the frequency of an individual interface failing and the number of interfaces, further qualifying with the likelihood that two interfaces failing within the same recovery window are actually on either ends of a link. Note that it is possible, although unlikely, that both the link has failed and the two interfaces have failed. That is, the alternative root causes may not be mutually exclusive. In this case, remedial actions for both faults are required.

Matching. In one embodiment, the matching of an actual fault scenario to potential fault scenario, as performed by a matching mechanism, is exact in the sense that each matched potential fault scenario may be required to be such that the actual fault scenario satisfies for each symptom the symptom requirement specified in the matched potential fault scenario.

For example, if the potential fault scenario specifies a symptom S1 to be the temperature of an oven being greater than 100 Celsius, the actual fault scenario should include this symptom being reported as greater than 100 Celsius.

This matching contrasts with the input probability approach used for example, in SMARTS, in which there is some probability that the symptom is true, even if the sensor is not reporting this, given the uncertainty about the sensor as captured by the associated probability. It also contrasts with the various seemingly arbitrary "distance-based" approaches such as the Hamming distance approach, in which the ARCA system is selecting a "best match" based on the distance by some metric between the actual symptoms and the symptoms associated with a root cause, analogous to a potential fault scenario. In one embodiment, generation of the matchset is performed by a ternary matching mechanism as described herein with the ternary RCT representation.

The unrefined fault scenario matchset may include multiple members even with matching a single actual fault in part because the set of potential fault scenarios should cover the cases in which some telemetry is missing or wrong. For example, FS3 in the Network Example above is provided so that there is some match even if telemetry for ancillary symptoms is not complete or incorrect. That is, it would be unacceptable to not be able to diagnose a link failure in link a (722) just because one (702) or the other of the switches (742) was unable to report on power (706), (746) to an interface.

In general, matching may be efficient to implement and able to match multiple independent root causes simultaneously as described in the above application regarding ternary fault scenario representation. Matching has the disadvantage that it fails to match when any specified symptom in the potential fault scenario that corresponds to the actual fault scenario does not match the symptoms determined from the telemetry. This may arise even when a human evaluation of the symptoms might quickly conclude what the root cause is.

Figure 9:
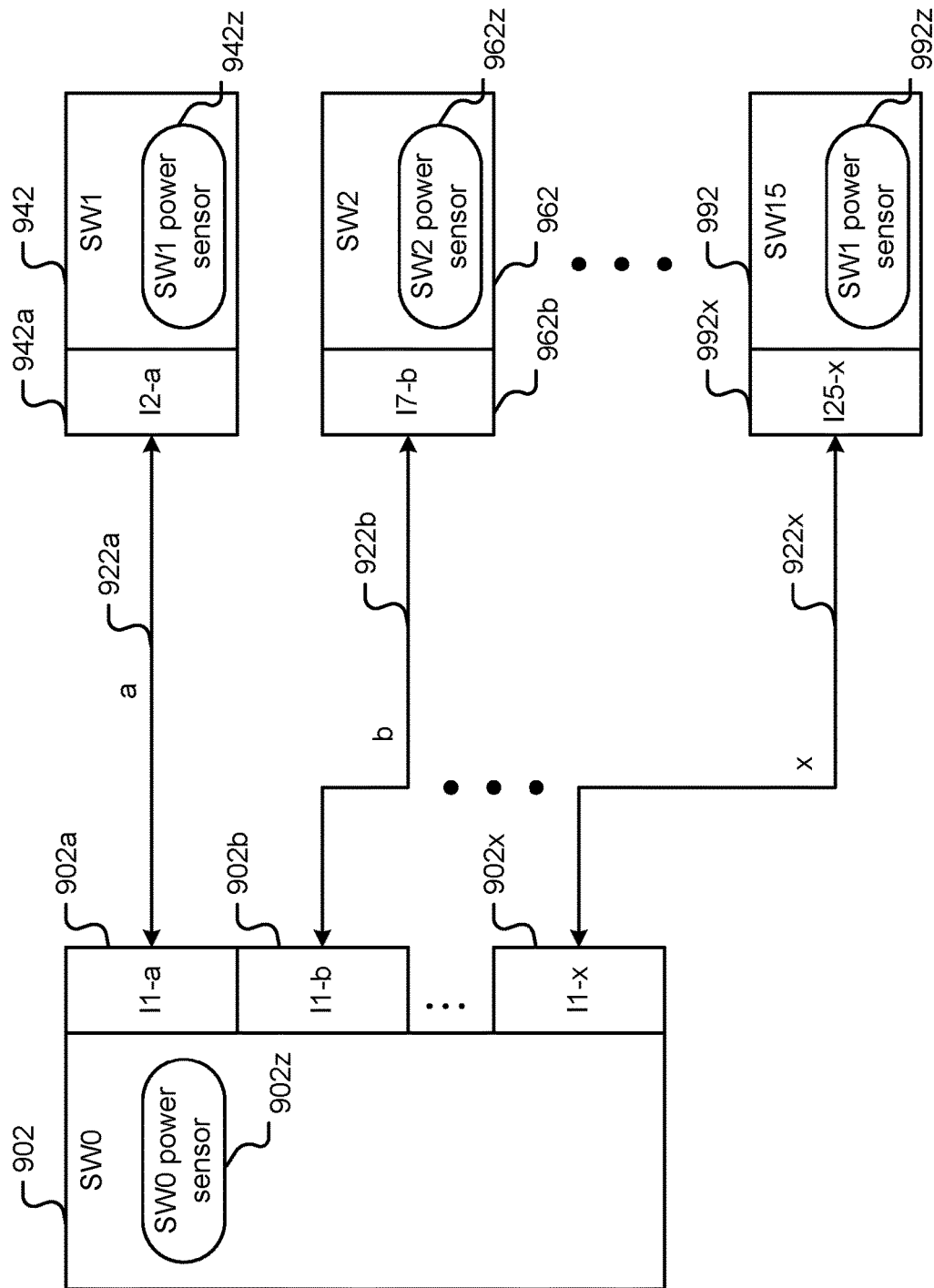
FIG. 9 is a block diagram illustrating an embodiment of a power example.

FIG. 9 is a block diagram illustrating an embodiment of a power example. In this Power Example, a switch SW0 (902) is fully coupled via interfaces and links to 24 other switches SW1 (942), SW2 (962) through SW15 (992). As shown before in FIG. 9, each switch for example switch SW0 (902) comprises a power sensor (902z) as well as one or more interfaces I1-a (902a), I1-b (902b), I1-x (902x) each corresponding to a link a (922a), b (922b), . . . , x (922x).

If the power to a computer network switch SW0 (902) including SW0 power sensor (902z) fails, one would expect that each interface to which the switch is connected over a link would detect a loss of signal. However, if the switch in question is connected over links to 24 separate interfaces I2-a (942a), I3-b (962b), I25-x (992x), but only 23 of these interfaces are reporting loss of signal and a 24th one I25-x (992x) is missing from the telemetry, matching would fail matching to a potential fault scenario that specified all 24 separate interfaces having the symptom loss of power—even though any reasonable person may conclude from the symptoms that the switch had failed, and furthermore failed due to lack of power if that switch SW0 power sensor (902z) reported loss of power.

As shown herein, leveraging the ability of such matching to match to multiple fault scenarios at the same time in order to compensate for this disadvantage is important. In particular, besides having a potential fault scenario that corresponds to all the symptoms, there are potential fault scenarios specified that correspond to partial matches for the same root cause. The extension to associated attributes with potential fault scenarios allows a refinement of the matchset to reduce number of potential root causes that are actually output.

In particular, when a match to the full potential fault scenario occurs, the potential fault scenarios corresponding to partial matches of the same root cause are eliminated and/or subsumed. Similarly, the probability attribute associated with a potential fault scenario allows the output to efficiently indicate a lower confidence for a root cause in the output when it is present only because of what is effectively a partial match.

In one embodiment, another technique for allowing partial matches is termed "approximate matching" and is used for a case in which not all features, for example subconditions, are necessarily known. Approximate matching can thus be used in conjunction with partial matching.

In one embodiment, approximate matching is provided by specifying a distance threshold parameter and outputting rows as matching if they are within the distance threshold according some distance metric defined between a row and the mask. Processing extra matches to reduce and organize matches for efficiency in interpretation may be improved by approximate matching in part by treating an approximate match at distance D, for example, as a base root cause relative to a match at distance D−1.

Partial-Match Potential Fault Scenarios (PMPFSs). A PMPFS is referred to herein as a potential fault scenario added to effectively handle partial matches with a matching mechanism. There are various techniques to define PMPFSs.

A PMPFS that omits one symptom. First, for each full potential fault scenario for a root cause, there may be for each symptom a PMPFS that omits one of the symptoms. For example, using the Power Example of FIG. 9, there may be a PMPFS for each neighboring interface which omits this interface as a symptom or alternately designates this symptom as a "don't care". For example, a PMPFS may omit I25-x (992x) as a "don't care" and thus with I2-a (942a), I3-b (962b), . . . , I24-w (not shown in FIG. 9) reporting a loss of signal, the system may conclude the switch SW0 (902) has failed.

It may be possible to go further and provide a PMPFS for a subset of symptoms of the full potential fault scenario. For example, create a PMPFS for both I24-*w* and I25-*x* (992*x*) as "don't care". However, that may lead to an impractical number of PMPFSs in systems of realistic complexity. For example, in the example of a switch with 32 direct neighbor switches, there are basically 2 to the power of 32 or roughly 4 billion possible subsets. Here, approximate matching may solve the issue with excessive number of PMPFS. Put another way, partial matching may be thought of as adding extra rows that are less complete, whereas approximate match is relaxing the match criteria so one can match rows that do not exactly match the mask, or actual complete set of symptoms.

A PMPFS that excludes a range of values. One method to effectively support partial matches while avoiding an exponential explosion in the number of PMPFSs is to allow a potential fault scenario to specify a given symptom as excluding some value, or a range of values. Typically values are used that would contradict the associated fault being the root cause. In the Power Example of FIG. 9, a PMPFS may be specified as requiring the lossOfSignal symptom to be either true or not known. Then, a match occurs as long as no neighbor switch is claiming to receive a signal from the switch that has supposedly lost power. That is, the match still takes place if this symptom is not known for some of the neighbor switches, for example I25-*x* (992*x*) which was unknown.

In one embodiment, the representation of a PMPFS allows the specification of exclusion-based matches, not just inclusion, in range specifications. For example, in the referenced disclosure, the binary representation of a ternary value can use the "unknown but true" value (i.e. 01) that is otherwise unused to designate "not known to be true". In general, there exist traditional techniques for data representation that may be used to efficiently encode extra information that correspond to exclusion as well as inclusion.

Restricting scope of a PMPFS. Another method to effectively support partial matches while avoiding an exponential explosion in the number of PMPFSs is to restrict the scope of a PMPFS and its symptoms and corresponding reduce the probability associated with it. In the Power Example of FIG. 9, a PMPFS may be generated that matches on the current power failure sensor (902*z*) for the switch SW0 (902) and specifies "don't care" in effect for the telemetry of the neighbor switches (942*a*), (962*b*), (992*x*). This PMPFS then matches if the power sensor (902*z*) reports a power failure yet there is contradictory information from one or more neighbor switches, such as an "unknown" for I25-*x* (992*x*), which may be incorrect or stale.

On the other hand, if the above PMPFS for the same switch SW0 (902) matches with an exclusion-based match, this lower probability match is filtered out by the refinement step. In general, the generation of a PMPFS may restrict the scope based on relationship to other elements, the types of the other elements, specific properties of these elements and other attributes.

Defining an aggregate symptom. Another method to effectively support partial matches while avoiding an exponential explosion in the number of PMPFSs is to define an aggregate symptom that is set based on telemetry across multiple sensor inputs. In the Power Example of FIG. 9, one may define an aggregate symptom that corresponds to more than some threshold K of neighboring switches SW1 (942), SW2 (962), . . . , SW15 (992) having loss signal from a given switch SW0 (902). Then, a PMPFS for switch loss of power may specify this aggregate symptom so that the switch has deemed to have had a power failure if most of its direct neighbors have loss signal from it. To be clear, the benefit of incorporating this information from its direct neighbors is that it helps disambiguate this case from that in which the current sensor on the switch has failed, not the power itself.

Back propagation of symptoms. Another method to efficient support partial matches is to exclude from a PMPFS symptom requirements that have been determined by what is referred herein as back propagation, short for "back propagation of symptoms". In the Network Example of FIG. 7, one likely explanation for a signal not being received at the far/SW1 end (742) of link *a* (722) is a broken network cable. An alternative explanation for a signal not being received at the far end of the link is that the interface I1-*a* (704) at the near/SW0 end (702) has lost power. This is because loss of power at an interface at one end of a link (722) effectively propagates a loss of signal symptom to the interface at the other end of the link.

Using back propagation of symptoms, the full fault scenario of symptoms for this scenario requires that the loss of power symptom for each interface and/or switch (706), (746) is false. However, this back propagation also means that if the current power sensor (706) for this switch SW0 is faulty, the ARCA may fail to match to the full fault scenario and thus not determine the root cause unless there are matching PMPFSs. In this case, there may be a PMPFS that excludes these symptoms arising from this back propagation, typically with an associated lower probability given the uncertainty introduced by ignoring the symptoms that would otherwise be required because of the back propagation.

Combinations using back propagation of symptoms. Each of the earlier techniques or methods may also be applied to back propagation of symptoms, including: 1) using a subset of the back-propagated symptoms 2) using an aggregate of the back-propagated symptoms, and 3) using exclusion of symptoms values, rather than an inclusive range.

In general, PMPFSs allow an engineering trade-off between accuracy of root cause analysis and the computer memory/processing for a large number of PMPFSs. That is, computer memory requirements may be reduced and/or computer processing speed may be increased with fewer number of PMPFSs. More accurate analysis requires more compute resources than a less accurate analysis. However, beyond a point there are diminishing returns for using more PMPFSs, as the uncertainty with correctness and availability of telemetry limits the certainty of any analysis.

Using the techniques herein recognizes and addresses a major fallacy in the traditional approach to ARCA; the assumption of a single root cause and the assumption that determining that the actual root cause is feasible to determine with certainty from sensor input. Sensor input may be incorrect. Generating a set of potential root causes based on matching potential fault scenarios, some of which may correspond to the same root cause fault, and then providing a refinement step to produce a curated set of potential root causes may thus be one way of selecting the RBS action based at least in part on probability.

In one embodiment, the model may specify that the actions are commutative in the sense of "may be performed in any order and do not affect the evaluation of conditions", and this is referred to herein as a commutative action RBS (CARBS). In one embodiment, when the model so indicates, the implementation may perform the action associated with each of the multiple entries in the matchset without rematching. For example, in the self-driving case, the matching may identify both "enteringGreenBlockedIntersection" and "aboutToTurnRight" with the action associated with the first condition being "comeToStop" and the action associated with the second condition being "turnOnRightSignal". It makes sense to perform both actions in this case.

In one embodiment, one or more scenarios in the matchset may be identified as alternatives of a given scenario S, using matchset refinement as described above. In this case, the scenario that is identified with the greatest confidence and possibly other criteria may have its action performed, while suppressing or not performing the actions of the alternatives.

In one embodiment, it may be necessary to ensure that some action is not executed repeatedly when the associated rule condition remains true. There are various techniques to avoid re-execution. For example, the implementation may record the time of the condition match that it last executed the associated action and not re-execute the action until the condition has become false and then true again. That is, if there has been no update to the match timestamp, the action is not re-executed.

One alternative approach is to make an action idempotent. That is, if the action procedure is executed more than once in the same scenario, it has the same effect as being executed once. For example, the action of "comeToStop" may be made idempotent by having it continue applying the brakes if it is already applying the brakes, so invoking this action multiple times has the same effect as invoking it once, that is "idempotent" as referred to herein. An idempotent action may be re-executed on each match, but has no effect in second and subsequent matches.

In general, there are a variety of means to separate the action implementation from the classification of scenarios, to parameterize the action implementation in terms of the triggering scenario, and to perform conflict resolution and/or matchset refinement and deal with action re-execution. Moreover, these techniques may be independent of the actual model being specified so are not strictly dependent on automatic code generation. This is evident from the above code snippets in which the action mapping code is not specific to any aspect of the model, unlike the condition code itself.

That said, automatic code generation may perform various optimizations in the action mapping, such as eliminating the code for conflict resolution when the model is specified as a CARBS instance. The action itself is assumed explicitly specified as a procedure or similar, so may not necessarily require or entail automatic code generation herein. Therefore, rule condition code generation is described below.

Automatically Generation of Rule Condition Code. The automatic generation of rule condition matching code may be more sophisticated than that outlined above for realistic application models. For instance, the previous example suggested there being a single trafficLightDetector, an intersectionDetector and obstacleDetector. However, in reality there may be numerous traffic lights and intersections in the area that the AV is traveling. Thus, the intersection detector needs to be pointed at the one relevant to the position and velocity of the AV, same with the trafficLightDetector and the obstacleDetector. That is, the obstacle detector may need to detect obstacles on the path that the AV is travelling.

In a table-based embodiment, this issue is addressed by generating a symptom per element instance and generating a row in the RCT for each combination of trafficLightDetector, intersectionDetector and obstacleDetector-specific symptoms for those that are colocated. The example used earlier from the network domain further illustrates this approach. The RCT approach generates a row for each pair of connected interfaces, with the symptoms specific to those interfaces set to indicate loss of signal, along with a row for each uni-directional cable failure. In effect, there is a DAG as illustrated in FIG. 8B for each pair of connected interfaces, with the corresponding row containing the leaf subconditions for that DAG. Thus, if there are 10,000 cables in a data center network, there are 10,000 rows associated with this one logical fault, one for each pair of interfaces. This approach of separate actual symptoms and rows for different parameter values in effect for a condition is an approach used for automated root cause analysis.

In one embodiment, explicit condition evaluation code is generated instead of relying on table matching. Each non-const rule may thus have a code snippet generated that evaluates the associated rule condition that is parameterized in terms of the elements involved, and there is an associated data structure that provides these elements as parameters. The evaluation of the condition for this logical root cause is then performed by iterating over this collection, invoking the code snippet for each set of parameters, as indicated in this data structure. For example, there may be a collection of the pairs of connected interfaces which is then used to invoke the code snippet associated with detecting a cable fault. Iterating over this collection, invoking the code snippet on each pair then detects if there is a cable fault.

Note that, using this example, there may be 10,000 entries in this collection for the 10,000 cables in the data center network, similar in space overhead to some degree to the 10,000 rows in the RCT associated with this fault. However, if there is a second root cause fault that is associated with connected pairs of interfaces, the same collection of pairs may be used to iterate with this second root cause code snippet, whereas with an RCT, there is necessarily a second set of 10,000 rows associated with this second root cause fault. For example, if there is a root cause that implies from one interface to the other, as opposed to bidirectional implication from the cable, this same collection may be used to evaluate this other root cause. For instance, if one direction of a cable is broken then one interface detects a loss of signal but the other interface does not. This root cause fault may be identified using the same collection of interface pairs, similar to that shown in FIG. 9.

In one embodiment, when multiple conditions use the same or a subset of the parameters of a given logical root cause, these multiple conditions are combined into a single code snippet that may be invoked as part of the iteration of these parameters, evaluating the set of conditions for each step of the iteration. For example, each step of the iteration might detect if there is a broken cable, half-broken cable, excessive packet corruption and excessive packet drop in a single invocation of the associated code snippet.

In some applications, there is a need, independent of the rule execution, to maintain data structures that correspond to the elements, their attributes and their relationships. For example, a network management application may require maintaining an object per switch in the network that stores attributes of the switch and its relationships to other elements in the network, including how it is connected to other switches.

In one embodiment, when the application maintains objects corresponding to the elements and their relationships, these data structures are used to provide the parameters for one or more of the RC code snippets. For example, continuing the above example, the rule engine may iterate over the element objects, determining for each one, the other element(s) to which it is connected, thereby generating the pairs of connected interfaces that are required for rule condition evaluation in the above example. Then, a separate collection of connected interface pairs is not required. In this case, given the application is storing this information for other purposes, the explicit rule condition code generation approach does not generate extra space overhead by its need for these parameters for its code snippet. On the other hand, it does not seem feasible to capitalize on the application state associated with elements and relationships to reduce space when the table-based approach is used, so the latter likely incurs more space overhead in these applications.

In other realizations of automatic root cause analysis with an RCT, the current symptoms are periodically matched against the table to check for root cause faults as illustrated in FIG. 5D. Similarly, a rule engine normally repeated polls the entire rule set to check for rule conditions that are true, in order to detect that a rule action may be triggered. However, this approach suffers from the typical trade-off between the overhead of rapid polling and delay to detect conditions that may trigger actions. In particular, higher frequency polling to minimize delay in triggering an action introduces significant overhead whereas lower frequency polling to reduce this overhead increases the delay to trigger after a condition becomes true. An alternative approach supported with explicit rule condition code is to have a reactive implementation in which an input attribute change triggers an immediate re-evaluation of the rule conditions that are dependent on this input. Thus, the action may be performed without delay if the rule condition for that action has now become true. Such a reactive implementation is described below.

Reactive Rule Engine Implementation. In one embodiment, a compiler outputs code that implements a reactive rule engine. It may be reactive in the sense that it directly reacts to input changes and performs the actions associated with rule conditions that have become true as a result of the input change, if any.

Figure 10:
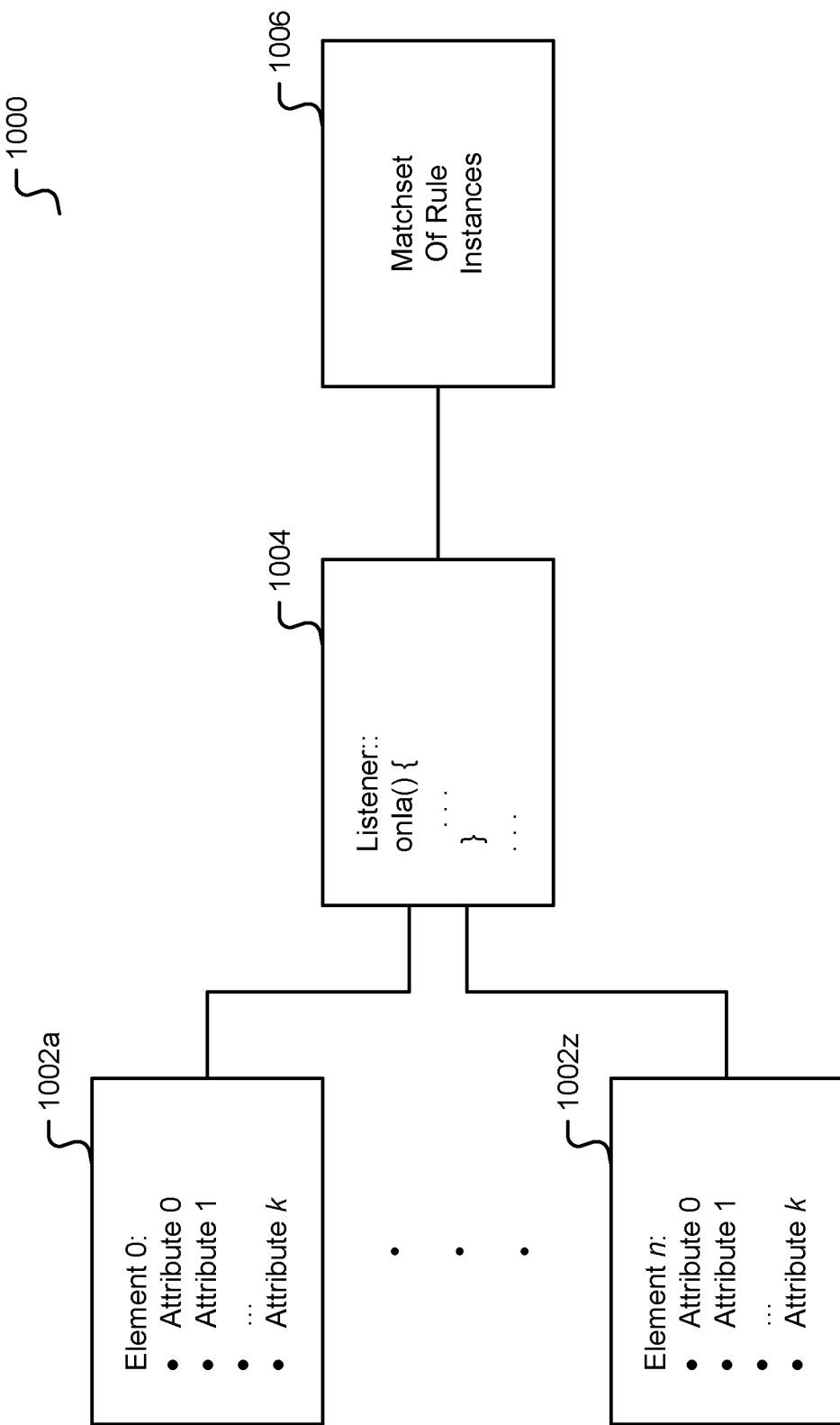
FIG. 10 is an illustration of an embodiment of a reactive rule engine.

FIG. 10 is an illustration of an embodiment of a reactive rule engine. In one embodiment, the reactive rule engine is realized as a "listener" module (1004), as shown in FIG. 10. The "listener" or equivalently "observer" (1004) is a traditional software design pattern in object-oriented programming. In essence, a listener (1004) is a module that is notified by a callback when some attribute of interest in one of the "listened-to" objects (1002) has changed. Thus, the listener (1004) reacts to element attribute (1002) changes, adding a rule instance to the matchset (1006) if the rule condition is true.

There are established techniques for manually implementing a listener module in C++ and other languages. Overall, in this embodiment, the compiler portion generates the code for the element types and callback notifications using other techniques, including those disclosed in U.S. patent application Ser. No. 12/154,354 entitled DYNAMIC COLLECTION ATTRIBUTE-BASED COMPUTER PROGRAMMING LANGUAGE METHODS filed May 21, 2008 which is incorporated herein by reference for all purposes. It further generates a listener module (804) using the techniques in U.S. patent application Ser. No. 12/154,399 entitled NOTIFICATION-BASED CONSTRAINT SET TRANSLATION TO IMPERATIVE EXECUTION filed May 21, 2008 which is incorporated herein by reference for all purposes, with a callback procedure for each callback notification, namely for each modifiable attribute that is required for evaluating an observable subcondition. In this context, a rule may be regarded as a constraint between the model and a matchset of action labels that requires the action label for the rule to be in the matchset collection if the rule condition is true.

In one embodiment, the listener module (1004) is generated to listen to each input attribute of each element (1002a, 1002b, . . . 1002z) that is instantiated in the model. Thus, in C++ terminology, the compiler defines a class with a data member that points to each element to which this module needs to listen or react, either as a single pointer or as a collection of pointers if there are multiple such elements of the same type. For each input attribute ia, the compiler also generates a callback function "onIa( )". Following standard practice in C++, this callback may be in a separate class that is a derived class of the callback interface, which then calls into the actual main listener module class. The callback function is generated with code to evaluate each of the rule conditions specified in the model that is effected by this input attribute ia changing. Consequently, when attribute "ia" changes, this Listener::onIa( ) (1004) procedure is invoked. This procedure evaluates the rule conditions that are dependent on this input and outputs the action labels for each rule condition that evaluates to true (1006).

Note that especially with more complicated rules, the relationship between objects clarify and/or indicate connections. The compiler also generates the necessary data members and collections in the listener module to allow these rule conditions to be evaluated. For example, returning to the example of the computer network model, the rule condition corresponding to a broken link needs to know the "other" interface, the one at the other end of the link, to evaluate the rule condition as illustrated by the following code:

```
otherInterface = getOtherInterface(notifier( ));
if(notifier( )->lossOfSignal( )&&(otherInterface-
>lossOfSignal( ))    {
        indicateCableBreak( );
}
```

The generation of the "if" condition in the above code snippet is straight-forward because it is just the conjunction of the observable subconditions that are the leaves of the DAG rooted at the rule condition, as was illustrated in FIG. 8B.

In the above, "notifier" corresponds to the interface element that is performing the callback and otherInterface is the interface to which it is connected (indirectly through Link and Unilink objects), as returned by getOtherInterface. Thus, the compiler may generate code to store and maintain a collection in this listener module that may hold the connected interface pairs. Consequently, when the above condition is to be evaluated as part of executing this callback function, the "otherInterface" variable in the above code is set to the interface that the "notifier" interface is connected to by accessing this collection.

Note that an input attribute is specified as input in the model but may be a complex calculation from actual system inputs. For example, an input attribute may be a weighted moving average of some raw sensor value that is only updated when the average changes by a significant amount. Thus, the actual input may be changing more frequently and with more significant changes that the input attribute used in the model.

In one embodiment, the listener module (1004) is realized as a derived class (in C++ terminology) of a base class that defines and implements the action procedures. For example, the actions may be manually specified in C++ as follows:

```
class ActionModule {protected:
    void indicateCableBreak( Interface * intf0, Interface * intf1
);
    void indicateUndirectionalCableBreak( Interface * intf0 );
...
}
```

The procedure bodies may be specified separately as is typical practice in C++. Then, the rule model may be generated as a derived class of this ActionModule, e.g.

```
class RuleModule : public ActionModule {
    ...
}
```

That is, the (generated) RuleModule is a derived class of the ActionModule which may be explicitly programmed so it is able to access the "protected" action procedures provided by the latter module. Then, the rule evaluation code may be generated for each input attribute as described earlier, and the calls to the action procedures just invoke those specified in the ActionModule, which is incorporated by inheritance into the Rule Module.

In one embodiment, selected portions of the listener module code may be provided by manual programming. For example, by specifying "external" in a rule condition, the automatic generation does not generate a rule condition for that rule, but instead assumes/relies on manually specified code that handles this condition. This provision recognizes that there often a need for a few special optimizations for a particular application that are beyond that supported by the compiler.

Figure 11:
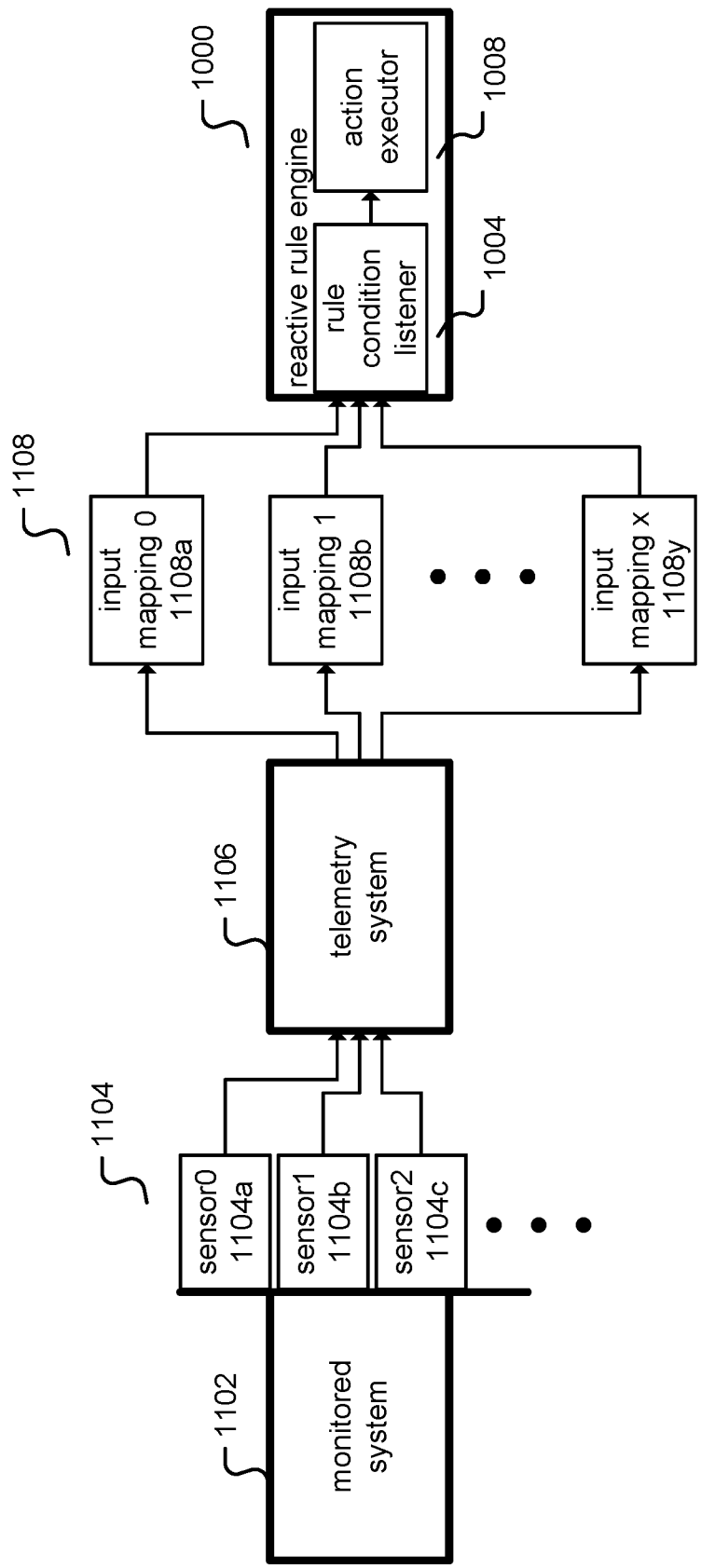
FIG. 11 is an illustration of an embodiment of a reactive rule engine in a monitored system.

FIG. 11 is an illustration of an embodiment of a reactive rule engine in a monitored system. FIG. 11 shows how the reactive rule engine (1000), structured as a listener module (1004) and an action execution module (1008), is connected to a monitored system (1102 to 1108). In FIG. 11, sensors (1104) provide measurements of values associated with the monitored system (1102), such as temperature, humidity, and so on. These values are collected by a telemetry system (1106) that delivers these values for input processing (1108), which may take several actions on the inputs. For example, it may translate the sensor input values from one measure to another, such as from A/D units to temperature in Celsius. It may also interpolate or extrapolate sensor values in the case of missing values or smooth or correct sensor values in the case of spikes or erroneous values that may be due to sensor transients. In that vein, it may provide a computed value from the inputs, such as a weighted moving average on some input. It may also discretize the input stream into a small number of discrete values defined by thresholds, such as for example cold, cool, warm and hot for a temperature reading. Thus, the reactive rule engine (1000) is only reacting to changes of temperature that cross a threshold. Finally, it may withhold input values from the listener (1004) until some specified period or round, to support periodic polling for rules, rather than reacting to each input changes, as described later. That is, mapping may restrict the reactive rule engine to only reacting to threshold crossings to reduce noise, withhold input value to reduce noise, and so on.

In one embodiment, if multiple rule conditions are dependent on the same input attribute, the compiler generates these rule conditions in the same callback function.

To recognize a rule condition in the matchset that is no longer valid, a periodic process may test the set of matched rule conditions and delete it from this collection if it is no longer valid and/or when an element "bar" changes, it may prompt the re-evaluation of any RC in the set that is dependent on this element. In an embodiment in which only a single independent rule condition should be true at any time, the matching to a different rule condition can immediately delete the existing rule condition, if any, from the match set.

In one embodiment, as an optimization, the compiler may recognize the case of objects in the model that exist entirely for const rules and do not correspond to any inputs. For example, a cable in the network typically has no sensors on it, and thus is modeled without input indicators. It exists only to provide a context to specify one or more rule conditions and their implications. In these cases, the compiler may optimize these objects out by collapsing the relationships so the evaluation takes place directly to the objects with observed symptoms. For instance, in the example of a computer network, the Link and Unilink objects may be optimized out and the interconnection between interfaces may be recorded directly in the Interface objects. In particular, with this optimization, an interface contains an attribute "otherInterface" which points to the interface it is connected to. In the special case of a relationship like "parent", the parent is easily determined from the component element by the usual parent back pointer.

A non-binary relationship may be decomposed into binary relationships, so the above approach may be used to handle ternary relationships/parameters as well. When the reactive rule engine software is initially executed, the generated objects may be instantiated with initial values for the input attributes that do not occur in practice. The rule engine process and these input attributes may then be connected to the actual telemetry which causes these input attributes to be changed to different values, causing the reactive behavior to match the rule conditions as described earlier, and then invoking the relevant rule(s), if any.

In one embodiment, the compiler optimizes the generated code in the callback function to reduce the execution time and the code size. For example, in the above code snippet, if another rule condition requires the "otherInterface", the generated code is optimized to access this value once from the above collection and use this value for both rule conditions.

As another candidate optimization, the subexpression involving this notifying input attribute may be tested first before performing actions necessary to evaluate the rest of the rule condition. For example, the above code snippet may be optimized as follows:

```
if(notifier( )->lossOfSignal( )) {
    otherInterface = getOtherInterface(notifier( ));
    if(otherInterface->lossOfSignal( )) {
        indicateCableBreak( );
    }
}
``` where getOtherInterface is a procedure that returns the other interface.

Nesting the getting of the otherInterface within an "if" block means that getOtherInterface procedure call is only executed if the notifier's lossOfSignal attribute is true. In the expected common case, this attribute may be false, thereby saving the cost of this call A further optimization is to recognize common subexpressions in the rule conditions that are being evaluated. For example, the rule condition corresponding to unidirectional cable break corresponds to loss of signal at one end but not the other. I.e.

```
if(notifier( )->lossOfSignal( )) {
    otherInterface = getOtherInterface(notifier( ));
    if(!otherInterface->lossOfSignal( )) {
        indicateUndirectionalCableBreak( );
    }
}
```

By recognizing common subexpressions, this rule condition may be optimized as per the following code:

```
if(notifier( )->lossOfSignal( )) {
    otherInterface = getOtherInterface(notifier( ));
    if(otherInterface->lossOfSignal( )) {
        indicateCableBreak( );
    }
    else {
        indicateUndirectionalCableBreak( );
    }
}
```

In one embodiment, the compiler can determine that one or more arguments for rule expression can be determined from attributes in one or more of the elements. For example, in the running example of a network, an Interface instance can have a pointer to the Unilink instance to which it is connected and the Unilink instance can have a pointer to the Interface to which it is connected. Plus, the interface necessarily specifies an inverse relationship, such as the connectedToBy relationship in the Interface. Therefore, the compiler can generate a C++-like implementation of the getOtherInterface as:

```
Interface::Ptr
getOtherInterface( intf ) {
    auto unilink = intf->connectedToBy( );
    return unilink->connectsTo( );
}
```

This procedure follows these pointers to return the "otherInterface" using the state in these network elements rather than having a separate collection of interface pairs, thereby avoiding the associated state overhead.

In one embodiment, the referenced attribute is a collection. For example, in a broadcast network, an interface may be regarded as being connected to multiple different interfaces. In such a case, the rule condition may be evaluated in an iteration loop, where the value of "otherInterface" is set to the next other interface for each iteration of the loop.

In one embodiment, an element type may be defined as a derived type of another element type, similar to the inheritance mechanism in most object-oriented languages. A derived type may add additional subconditions over those in the base type. It may also extend or override the subcondition implications provided in the base type. In a particular case, a derived type subcondition may correspond to an extended or refined version of a rule condition in the base type. Such a derived rule condition may extend or refine the observed subconditions of the base rule condition. For instance, a base rule may specify its rule condition to imply observed subconditions SC0 and SC1, so its condition expression is:

(SC0 && SC1)

whereas the derived rule may specify subcondition implication that further leads to SC2, so its condition expression is:

(SC0 && SC1 && SC2)

In one embodiment, a rule condition may be specified in the same type by specifying that it "extends" an existing rule condition, allowing a derived rule condition to be defined in the same element type as the base rule condition.

The derived versus base rule conditions may be used to effectively specify partial matching of subconditions. Or conversely, it may be used to avoid the case of a rule condition failing to match when one or more subconditions are missing even though the intended scenario is very likely the case. For example, a base rule condition for an object being a stop sign may be it having the observed subcondition of being octagonal as well as being red. A derived rule condition may specify the additional subcondition of the sign being inscribed with the word "stop". An object may still be recognized as a stop sign even if the inscription may not be read yet recognized with greater confidence as a stop sign if the inscription may be read. The derived relationship between these rule conditions provides an indication to suppress the match to the base rule condition when the derived rule condition is matched.

In one embodiment, the compiler may automatically generate derived rule conditions based on inference, that is back propagation of subconditions, as described above as back propagation of symptoms. In particular, the compiler may add observed subconditions in a derived rule condition that may be false, thereby disambiguating the specified rule condition from other rule conditions that otherwise overlap in the observed subconditions that cause them to trigger.

The optimizations described above may be used to optimize the code for handling the base condition and the derived condition(s) evaluation. In the simple case, the code is structured as:

```
if( <baseCondition> ) {
    if( <additionalDerivedCondition> ) {
        performDerivedAction( );
    }
    else {
        performBaseAction( );
    }
}
```

That is, the derived rule condition is evaluated only if the base rule condition holds.

In one embodiment, the action mapping/conflict resolution recognizes the case of both the base and derived actions labels being present and only executes the action associated with the most derived rule condition.

In one embodiment, an input subcondition may be defined as an expression in terms of actual input attributes. For example, rather than the Switch::lossOfSignalIn Boolean input attribute, a switch may have a Switch::signalInLevel attribute. Then, loss of signal from input is indicated by the expression switch→signalInLevel( )<minSignalLevel( )

In the model, this may be expressed as:

```
lossOfSignalIn : Subcondition {
    = signalInLevel( )<minSignalLevel( );
}
```

In one embodiment with input subcondition expressions, the compiler, as an optimization, generates code such that it performs the check that the subcondition associated with the notification is true on notification before performing the associated rule evaluation. That is, as an example, if notified of a change in the signalInLevel, the callback returns immediately if the value greater than or equal to "minSignalLevel".

In one embodiment as above, the compiler, as an optimization, generates code that evaluates this input subcondition before invoking the callback and only invokes the callback procedure if true.

The method used by the compiler to generate the rule evaluation code may be described as follows:

```
for each rule condition RC {
  1. follow the implication of subconditions from rule
condition RC to generate a set
    of observable subconditions, the observable subcondition set
(OSS).
    2. for each observable subcondition OSC in OSS {
      2.1 for each input/notifying attribute IA in OSC {
        2.1.1 find the callback procedure body data structure
for the "onIa" procedure,
          declaring this callback procedure if not already
declared.
        2.1.2 find an existing "if-else" statement in this
procedure that tests the subcondition associated with IA.
        2.1.3 if not found, instantiate this "if-else"
statement
        2.1.4 embed the rest of the subconditions in OSS in the
"if" block if a true subcondition
          and otherwise in the associated "else" block.
        2.1.5 insert the action or action label in the
resulting block that is entered
          if this condition evaluates to true.
      }
    }
}
```

Step 1 populates the OSS with the leaves of the DAG associated with rule condition RC, referring to the DAG representations of rule conditions illustrated in FIG. 8B.

In Step 2 above, the standard compiler technique of having an internal data structure representation of an "if" and "else" statement is assumed. Moreover, OSS is just a data structure representing the logical conjunction of the subconditions, similar to the parse tree structure found internal to many compilers. With this representation, additional statements may be added to the body of an "if" statement in the same way as such a data structure is normally built up by parsing input. The primary difference is that rule condition is embedded in an "if" or "else" statement that is conditioned on input attribute IA rather than being placed exactly as dictated by the parsed input as in a normal programming language. Also, the compiler needs to determine the access path to other values required to evaluate the rule condition, e.g. in our network example, determine how to access the "otherInterface". However, this access path may be determined by the relationships across which the current rule condition transits to this subcondition and the relationships from the current rule condition to these other subconditions In particular, for each other subcondition SCi, it uses the inverse relationships to access back to the rule condition scope and than the implication relationships to these other subconditions to build a path to access the data required for each subcondition. In one embodiment, the compiler has to evaluate the access path, in part to find the other interface. Thus, the compiler may use the DAGs to determine this access path through inverting relationships.

The steps to generate the code for finding the corresponding element or elements for a given argument to a condition are:
a. make the input subcondition be the current subcondition
b. find the inverse relationship for the relationship across which the current subcondition is implied. (The inverse relationship is indicated as such in the model, as illustrated by the connectedToBy relationship specified in FIG. 6)
c. generate code that processes each element in this inverse relationship as follows (either a "for" loop if a collection or an "if" condition if a singleton (to allow for this singleton being null)):
  i. get the subcondition that implied the current subcondition, if any. There is often a single such subcondition, so this is specified as such in the code in these cases.
  ii. follow the implying relationships across which this subcondition implies, forward to the input attributes, excluding the relationship corresponding to the inverse relationship just traversed. (In the "otherInterface" case, there is no other relationship except for the case of the rule condition itself.) Record the input attribute values to use as arguments to the condition.
  iii. if this subcondition corresponds to a rule condition, the argument generation is complete.
  iv. otherwise, invoke this procedure recursively on this subcondition.

For instance, in the case of the example computer network, the input attribute of "lossOfSignalInEth14" is known to be implied by interface named "eth14" from the "lossOfSignalIn" subcondition. The latter has no other implications. The inverse relationship to that implying this subcondition is the connectedToBy attribute, which then provides the in-bound Unilink object. The Unilink::lossOfSignal subcondition has an inverse relationship that is implied by the Link::cableBreak subcondition which is a rule condition, thus terminating the back propagation across inverse relationships. This rule condition implies across the components of Link that are of type Unilink. Because there are two such components, it is evident that there is a single "other" component, namely the other Unilink instance, given one may correspond to the relationship that is inverse to the other to get to this rule condition. Doing forward traversing on this "other" Unilink component yields the "other" interface to which this Unilink component is connected, which is the argument required in this case for condition evaluation. The generated code may be optimized to bypass the Link level and recognize the connectedTo Unilink instance as the inverse containing the pointer to the "otherInterface". The result is code that finds the "otherInterface" by a minimal number of memory references.

This same internal compiler data structure representation of this generated code may be used to perform various optimizing transformations to reduce the code size and improve execution performance using standard compile optimization techniques as well as others made possible by the structure and specification in the model.

The implementing of the rest of the subconditions described in the above sequence includes generating code to access the values used by these other subconditions, along the lines described for the "otherInterface" in the earlier examples.

In one embodiment, the model is expressed in a general-purpose object-oriented language in which the concept of a subcondition, and subcondition implication have been added. In another, a rule construct is added and the implications are indicated as Boolean expressions. The compiler is then extended to perform code generation on these rules, subconditions and implications, as described above.

To avoid excessive callback overhead, an input value may be discretized in the input attribute to a condition so that notification only takes place when the value crosses some threshold relevant to the condition. For instance, if a condition specifies the temperature as being hot as a subcondition, the temperature sensor may provide a discretized attribute that indicates only "hot" or "cold". Thus, a notification does not occur on each minor change in temperature but only when the input value changes from "cold" to "hot".

Polling and Polling Optimization. In some applications, a reactive execution of a rule engine incurs excessive overhead because of the rapid change in input values, most of which not leading to any rule triggering. For example, if the rule engine is performing root cause analysis and only triggers a rule when there is a system fault and a system fault rarely occurs, the vast majority of the reactions do not result in useful processing. Moreover, in some applications, the rules only need to be invoked when a condition persists for some time rather than only occurring transiently. This applies in the root cause analysis use case. After a fault occurs, the condition that indicates the fault tends to persist until the fault is remedied. With this assumption, it is not necessary to react to every input change. Instead, the rule engine may periodically re-evaluate the rule conditions rather than reacting to every input change. In one embodiment, the rule engine may invoke the same generated code to periodically evaluation all rule conditions.

In one embodiment, a periodic evaluation and triggering of rules is provided by only updating the input attributes to their current values at the start of each period. These updates causes the rule conditions that are dependent on input attributes that are changed as a result of updating to be (re-)evaluated on the current inputs. Thus, rather than reactive to each input attribute change, the same rule engine may be executed periodically and still operate correctly. In fact, the same generated code may be invoked to be reactive or to be invoked periodically, depending on how the input processing is configured. That is, the input processing may be configured to update input attributes as the input is received or only at a poll period interval. Note that the above processing assumes that in this application, not triggering an action in response to an intermediate change to an input between these periods is not a problem when the triggering condition is not true at the start of the next period. That is, the application allows skipping an action when its condition is only transiently true between periods of execution. In one embodiment, this may be done by freezing all inputs for a period of time and updating at a discrete time period later.

In an alternative implementation, the compiler generates a procedure PP that, when invoked, invokes each of the reactive procedures with each of the possible parameters. In this embodiment, this PP procedure is invoked at the start of each period.

In one embodiment, the implementation of the procedure is optimized to minimize or avoid duplicate rule evaluation. For example, considering the previous example of the rule condition associated with a broken link, the procedure may recognize that the evaluation of the rule condition with the pair of interface (intfj,intfi) is the same as evaluating the rule condition with the pair of interface (intfi,intfj) so only one of these is executed as part of this procedure execution. This embodiment can generate a single optimized pollEvaluate procedure that implements all the rule conditions when invoked, outputting an indication of the rule conditions that are true.

Overall, the same code generation techniques may be used to generate rule engine code for a periodic polling form of execution as well as for the reactive execution described earlier, and in one embodiment dynamically switch. One of ordinary skill in the art of software programming may recognize that a variety of optimizations may be implemented beyond the ones detailed here, allowing efficient execution in the case of polling form of execution.

Back Propagation and Automatic Checking of Rules. In one embodiment, the compiler checks for ambiguity of the rule conditions. Two conditions are partially ambiguous if there is a subset of inputs on which both match. The two conditions are fully ambiguous if the two conditions match on the same subset of inputs.

In one embodiment, the compiler checks for this ambiguity. One method of doing so entails generating the equivalent of a root cause table for the specified model and conditions. In particular, there is a column for each specific instance of an observable subcondition. For each rule, there is a row that represents the condition in terms of observable subconditions, where the entry for a given subcondition is true if the subcondition is true in the condition, false if the subcondition is false in the condition, and "don't care" in the case of a ternary matching RCT and the subcondition is not specified in the generated condition.

With this generated table, the compiler then performs a pair-wise match of each pair of rows in the RCT. If Ri matches Rj, then Rj is partially ambiguous to Ri. I.e. Ri matches whenever Ri matches. Similarly, if Rj matches Ri, then Ri is partially ambiguous to Rj. If the pair matches both ways, they are fully ambiguous.

In one embodiment, the compiler may output a warning message whenever it determines that a pair of rules are ambiguous, either partially or fully. The rule set maintainer may then choose to refine the model and the associated rule conditions to eliminate this ambiguity.

In one embodiment, the compiler may try to disambiguate a pair of rule conditions Ci and Cj that are ambiguous. In one approach, the compiler traces back from each subcondition SCk that is part of generating the rule condition Ci to any other subconditions may cause this subcondition SCi to be true that is not true for Ci condition. For such separate subcondition SCI, it forward traverses from that subcondition to an observable subcondition SCm and adds the negation of this subcondition SCm to the condition Ci. This addition ensures that Ci and Cj are no longer ambiguous.

Figure 12:
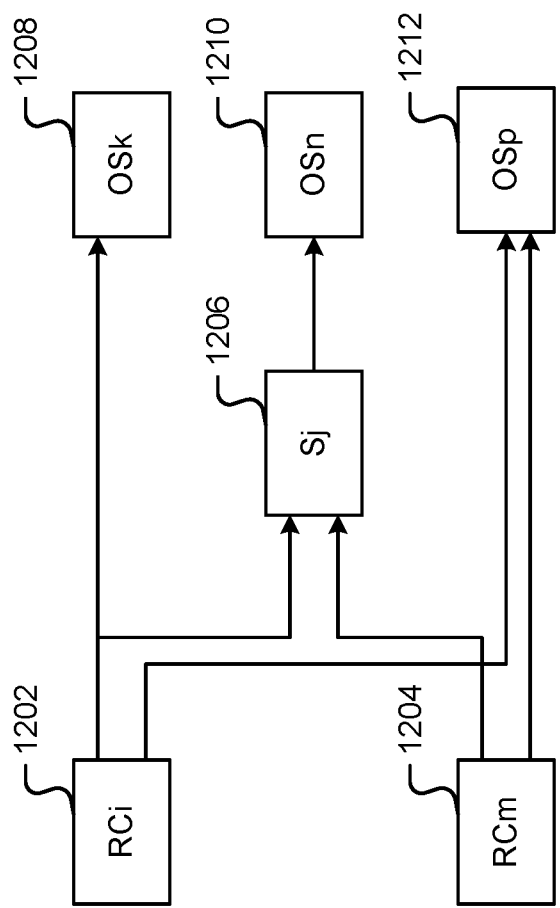
FIG. 12 is an illustration of an example of back propagation of subconditions.

FIG. 12 is an illustration of an example of back propagation of subconditions. RCi (1202) and RCm (1204) each imply observable subconditions OSk (1208) and OSp (1212), respectively. RCi (1202) and RCm (1204) also imply Sj (1206). RCi(1202) further implies OSp(1212). Thus, the compiler may add "not OSk" to the generated rule condition for RCm (1204) to further differentiate it from RCi (1202). That is, OSk (1208) being false means that RCi (1202) cannot be true. As a further example, considering a network of FIG. 7, a power failure on both switch interfaces can cause the same symptoms of lost of signal at each end as for a broken link. Therefore, back propagation would add a false entry for loss of power on interface for each interface to the row corresponding to cableBreak rule condition if the interface power symptom was added to the model.

In one embodiment, the compiler only reports as a warning the ambiguity of pairs of rule conditions that it is unable to disambiguate. Subsequent processing can determine the action to perform when this case arises.

Benefits of automatic generation of a rule set implementation. A first benefit of automatic generation of a rule set implementation is that it allows the implementation of a rule engine in which the rule condition evaluation is efficient because the forward and backward inference searching of others is removed from run-time overhead by compiling the rule conditions, either into a table or "if . . . else" statements.

A second benefit of automatic generation of a rule set implementation is that it allows a reactive rule engine implementation, that is, one in which it reacts to immediately to an input attribute change by re-evaluating the rule conditions that are dependent on this input attribute. This reactive approach works well when fast response is critical, and avoids the trade-off between overhead of rapid polling and slow response time.

A third benefit of automatic generation of a rule set implementation is that it allows automatic checking for under-specification and over-specification of rule conditions and disambiguation of under-specified rule conditions in some cases using back propagation. This facility reduces the difficulty of maintaining and extending complex rule sets. It also teaches how to completely embed the rule set in an application-specific object model, further aiding the development and extensions of complex rule sets. As can be seen from the above description, the detailed specification of the relationships between objects, as provided by the model, is a key aspect in the correct evaluation of rule conditions.

In the explicit code approach, as opposed to the table-based approach, there are further benefits. In particular, the explicit code approach makes it feasible to change the relationship between elements without having to recompile the model. It is a matter of modifying the collection(s) indicating a given relationship that has changed. For example, using the network example, a new interface pair (Ii,Ij) may be dynamically added when a new link is added between these interfaces without any recompilation.

Also, memory is saved in some applications because there is one instance of code to evaluate a condition rather than the N entries in an RCT and there is no need for a "working memory". For example, there is one snippet of code that checks for cable break, rather than N entries in the RCT, one for each pair of interfaces, i.e for each cable. This benefit is magnified when there are several conditions that use the same relationship(s). This is because the relationship is stored once but used multiple times whereas with an RCT, the number of rows corresponds to the number of conditions times the number of entries in this relationship. This approach is particularly attractive when the associated parameters and relationships are already being stored by the application and it is feasible to use this state to extract the parameters for each associated scenario. Thus, an advantage of this is that it may be faster and use less space in some cases.

One might consider the specification of subconditions and subcondition implication as just a distributed specification of the rule condition. To some degree this is true. However, a key aspect of the above is considering the entire rule set during compilation. This allows determination and handling of the relationship between rule conditions to be made explicit, allowing the rule set to be checked automatically for consistency and ambiguity. This enables ensuring that these conditions are consistent or at least allowing these conditions to be automatically checked for consistency. Moreover, the rule conditions may be automatically disambiguated by back propagation, to the degree possible within the model specification.

As described above, a rule set may be automatically checked for ambiguity, for example when two or more rules that trigger in response to the same subconditions. It may be important to avoid the case of the RBS causing two maneuvers to be triggered. It may also detect other cases, such as subconditions that are not specified in any rule condition or lane subconditions that are contradictory and thus the containing rule condition may never be matched.

As also described above, matchset-based ARCA and associated techniques like those associated with PMPFS may be used to eliminate subsumed conditions to reduce the number of triggered maneuvers.

With a lane rule set, there occur certain scenarios that the vehicle is unable to navigate through. For example, if the road is partially blocked from outside the road in the driving lane and partially blocked from outside of the road in the opposite lane, it may be impossible to transit the road by being in either the driving lane or the opposite lane. In this particular case, refining the vocabulary of lane maneuvers to include the maneuver of changing to straddling the center divider and adding the appropriate subconditions to trigger this maneuver may allow this scenario to be navigated.

As stated earlier, there is a trade-off between the complexity of the vocabulary of lane maneuvers and the scenarios that the vehicle can navigate. One recommended approach is to have the vocabulary of maneuvers be sufficiently comprehensive to allow all the expected scenarios to be navigated and a default maneuver for the case of no match for other scenarios, where this default maneuver may be getting human assistance, or switching to an alternative goal/route. Again, this is the same as with human drivers. If a driver cannot handle the vehicle in a given scenario, they can turn over the driving to another person, or change the intended destination.

A lane rule set may be developed iteratively, successively expanding the set of scenarios that it can handle properly and correcting problems that are pointed out by the compilation process. There may also be separate lane rule sets for different categories of scenarios, as described later, to avoid excessive complexity/matching cost, in each rule set.

Automatic Navigation Using A Lane-Structured Rule Set. A basic algorithm for automatic navigation, after developing one or more lane-structured rule sets, and accepting an intended destination for which there is optionally route guidance is:

Step 1. Update the lane subcondition indications from the sensor inputs, perception system and route guidance;
Step 2. Determine the rule conditions that are satisfied or matched to these updated lane subconditions;
Step 3. Initiate the maneuver(s) that correspond to these matched rule conditions, terminating any maneuvers that are in progress that correspond to conditions that are no longer are matched; and
Step 4. Repeat, starting at Step 1, once the lane subcondition indications could have changed.

The last step may be taken after a suitable delay given the subconditions may have changed as a result of the vehicle change or movement, if for no other reason. Alternatively, it can be triggered by a change in the sensor inputs, or another trigger. As described above with regards to ternary fault scenario representation, subconditions may be formed into a mask and matched against a table or provided to generate code that reactively indicates the one or more maneuvers selected.

A default maneuver may be provided for the case that the subconditions do not match any rule condition. This situation corresponds to the control system not understanding the current situation. A default maneuver may be to alert a human operator and/or take some precautionary action. For instance, in the case of a self-driving vehicle, the default maneuver can be to bring the vehicle to a safe stop.

In one embodiment, rule conditions may be further qualified by subconditions that indicate whether a particular subcondition relates to a known/understood element in the environment or not. For example, when an object appears in the right lane beside a self-driving vehicle, the rule condition matched may be different if the object is unknown versus known to be another car traveling in the adjacent lane. In the former case, the rule condition matched may initiate a precautionary maneuver whereas in the latter case, it is normally sufficient to just continue maintaining speed in the current lane. With this structure/feature, the vehicle may react immediately to sensing a new but unknown object rather than having its response delayed by a perception system. It may then use the more detailed and complex perception capabilities to reduce false positive precautionary moves when events occur with objects whose type and behavior are understood. In this sense, the system may react before understanding, rather than having to understand before reacting.

This behavior is applicable and important in other settings too. For example, in the medical treatment domain, detecting an adverse reaction or sudden degradation in condition in a patient calls for immediate remedial/precautionary action even before there is a full understanding of the cause of the adverse reaction.

Using Multiple Navigational Rule Sets. For modularity, to avoid excessive complexity in a given rule set and to minimize the rule condition evaluation cost, there may be a separate rule set for each different category of navigation scenarios. For example, with a self-driving vehicle, there may be separate rule sets for highway driving, city business district driving, and residential driving. There may also be different maneuvers and rule set for different weather conditions. For example, there may be a rule set for driving in slippery conditions and a different rule set for dry road conditions.

In a stock trading application, there may be different rule sets for bull market environments, high volatility markets, end-of-year trading, and so forth. In a medical treatment scenario, there may be different rule sets for different categories of patients, for example young, old, teenage, male, and female, as well as based on the apparent seriousness of the condition.

In one embodiment, a separate rule set may be used to select the rule set to use for navigation. For example, in a stock trading application, the rule set may be selected based on the trends with key leading stock indexes. With a driving application, the rule set may be selected based on the driving region such as a residential driving region or a commercial driving region, and the road conditions. In this embodiment, for each rule used for this selection, the rule condition is the condition under the associated rule set that may be used and the rule action, when triggered is to switch to using this rule set.

Handling a Lane-less Environment. In one embodiment, the vehicle control system includes a module that dynamically generates "virtual lanes" in an area with no lanes, based at least in part on general rules between vehicles as to how this is done. For example, if two self-navigating ships are travelling through the ocean, there may be general rules such as: the ship yields to the ship that is to starboard, and an overtaking ship yields to the ship in front and passes on the port side. Exploring this example more deeply: In many commercial shipping routes, there are established shipping lanes that effectively provide actual lanes to be followed, even if only designated by latitude and longitude. Thus, the default lane may be a shortest path to destination that is consistent with established shipping lanes and this virtual lane is then updated when overtaking another vessel to pass that vessel on the port side.

In general, an environment may be structured or partially structured by the imposition of lanes. A completely unstructured environment with dynamic events may mean that navigation has to be severely constrained or else the controlled element has to be able to react extremely quickly relative to the occurrence of an event and its own dynamic capabilities in comparison to a structured environment.

In summary, lanes represent a structuring and discretizing of the environment that correspond to a bounded number of actions, namely the lane maneuvers and correspondingly, a bounded number or lane subconditions.

Advantages. A first key advantage of using a lane-structured dynamic environment for rule-based automated control is fast reaction time. With fast rule condition evaluation, the system may provide fast reaction times. Using the table representation of the rule conditions and suitable hardware/software support, it appears that the rule condition evaluation may be performed in far less than 250 milliseconds, thus providing reaction times that are superior to normal human reaction times. Because local planning is eliminated, there is no delay introduced when an unexpected/dynamic event occurs that would otherwise have invalidated any local plans. With local planning eliminated, there is no delay to fully "understand" the current scenario after a dynamic event. The rule condition evaluation approach is open to numerous optimizations to make the evaluation both fast and efficient. By contrast, local planning computations with their dependence on complex perception, prediction, and constraint evaluation appear much more challenging to accelerate.

A second key advantage is that a lane-structured rule set may be pre-verified to select at most one maneuver in response to any set of subconditions so there is no need for so-called conflict resolution as in a conventional RBS. There is also no need to re-evaluate the rule set immediately based on taking an action because the actions have no direct effect on the subconditions, unlike the behavior of a general RBS.

A third key advantage is that lane-structuring results in a simplified rule set based on restricting the actions to lane maneuvers and the rule conditions as a logical expression in terms of lane subconditions. This lane-structuring simplification also means the automatic dynamic navigation is more understandable, predictable and explainable. On the latter, a maneuver or series of maneuver may be traced back to the one or more rules that caused each maneuver.

As a rule-based approach, using a lane-structured dynamic environment for rule-based automated control has all the advantages of an RBS, namely predictable explainable behavior. It also means that that the system may detect when no rule matches, when the vehicle does not "understand" the current scenario. The correct action in that situation is to notify an operator and possibly take some precautionary action such as bringing the vehicle to a safe stop. That is, because of the rule-based decision making, the system can know when it does not know. Moreover, those situations may be enumerated based on the non-matching scenarios relative to the rule set conditions. By contrast, probabilistic/statistics based approaches such as so-called machine learning (ML) do not provide this key property.

The key disadvantage of this approach is that it requires the environment to be structured into lanes. Therefore, it cannot deal with an unstructured environment. However, in many practical applications, the environment is already structured into lanes. Most physical vehicles travel on-road and there, the road system is structured into lanes. There are also logical lanes in medical treatment, stock trading and other applications. Also, in some cases when the environment is not pre-structured into lanes, a vehicle subsystem can impose lanes on an unstructured environment.

The lane-structuring of the environment is important because, without lanes, the environment is unstructured so the number of possible maneuvers that this vehicle and other vehicles may perform is unbounded, so the number of rule conditions is unbounded, and thus infeasible to implement.

Figure 13A:
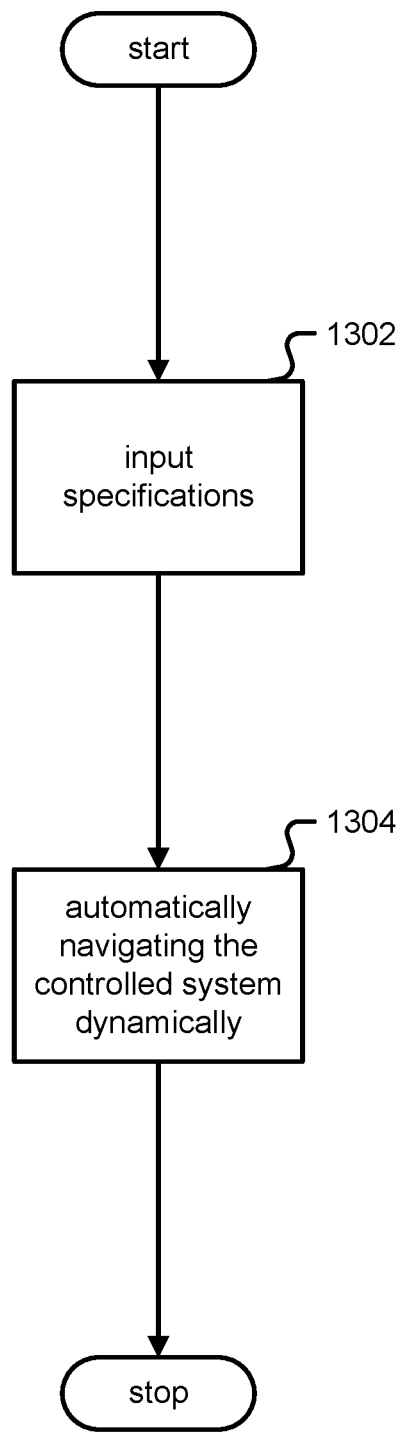
FIG. 13A is a flow chart illustrating an embodiment of a process for using a lane-structured dynamic environment for rule-based automated control.

FIG. 13A is a flow chart illustrating an embodiment of a process for using a lane-structured dynamic environment for rule-based automated control. In one embodiment, the process of FIG. 13A is carried out by the system of FIG. 1.

Figure 13B:
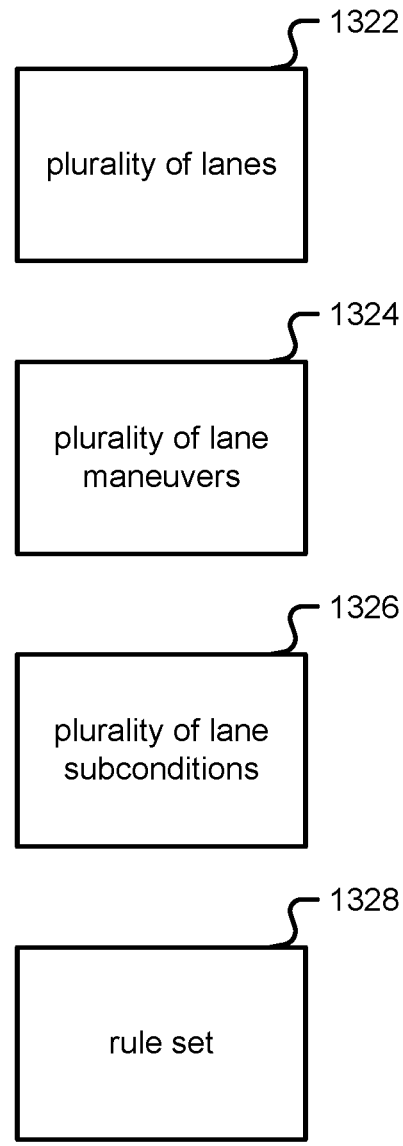
FIG. 13B is an illustration of an example of specifications.

In step (1302), specifications are input. FIG. 13B is an illustration of specifications. In one embodiment, the illustration of FIG. 13B is part of the specifications of FIG. 13A (1302). The specifications comprise:

- a plurality of lanes, including their adjacencies, in an environment for a controlled system (1322), for example in FIG. 2 lanes in an AV application (210), (214), (216), or in FIG. 3A lanes in a stock trading application (304), (306), (308), or in FIG. 3D lanes in a medical application (354), (356), (358). In one embodiment, the lane maneuvers, subconditions, rule sets, lanes and adjacencies are specified at "development time". In one embodiment, the lane maneuvers, subconditions, and rule sets are specified at "development time" and/or "compile time", while the specific lanes and their adjacencies are loaded at "run time" depending on circumstances, for example where the vehicle is located and/or driving, to improve efficiency;
- a plurality of lane maneuvers/rule actions associated with the plurality of lanes (1324), for example in FIG. 4 accelerate (408), switch to an adjacent lane (412), (414), or decelerate (410);
- a plurality of lane subconditions/rule conditions associated with the controlled system (1326), for example in FIG. 4 the subcondition of AV (402) being in the middle lane of a five-lane unidirectional road with no vehicles in adjacent lanes; and
- one or more rule sets, each rule set comprising a plurality of rules (1328), wherein a rule in the rule set specifies a rule condition and a rule action to take when the rule condition is satisfied, wherein the rule condition comprises a corresponding set of lane subconditions, and wherein the rule action comprises a corresponding lane maneuver, for example in FIG. 4 a rule indicating that when route guidance is indicating to exit, and no vehicles are in adjacent lanes, the AV may maneuver to the right adjacent lane (414).

Figure 13C:
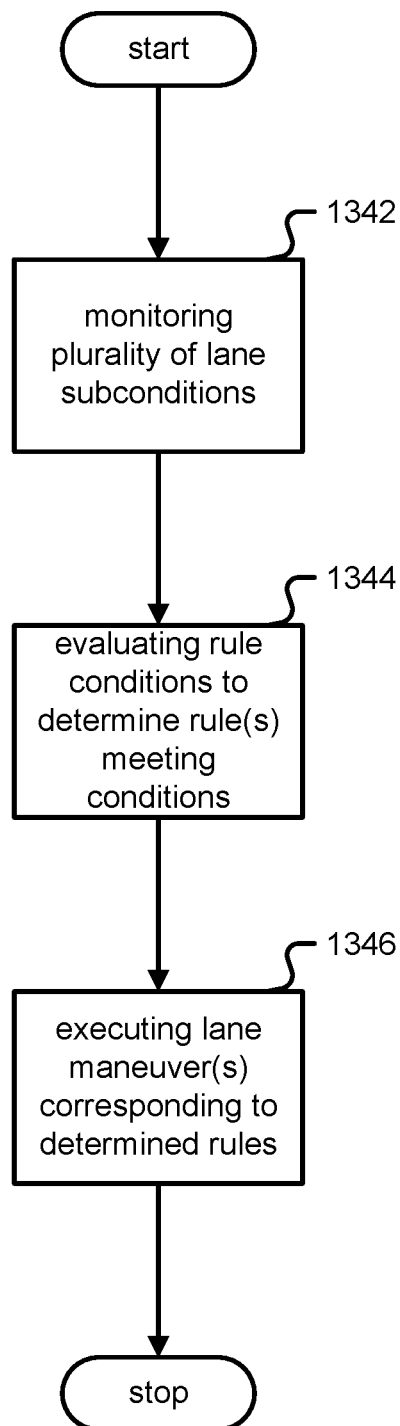
FIG. 13C is a flow chart illustrating an embodiment of a process for dynamic automatic navigation.

In step (1304), the controlled system is automatically navigated dynamically. FIG. 13C is a flow chart illustrating an embodiment of a process for dynamic automatic navigation. In one embodiment, the flow chart of FIG. 13C is part of the step (1304) of FIG. 13A. In step (1342), the plurality of lane subconditions are monitored, for example by polling a set of subconditions for changes in subconditions such as "noVehicleInAdjacentLanes", or using a more interrupt-driven logic such as having a sensor interrupt when a state changes, such as a vehicle moving into an adjacent lane. In step (1344), rule conditions associated with the plurality of rules in the rule set are evaluated to determine one or more rules whose corresponding rule conditions has been met. The evaluation may be done periodically or in response to a state change. In step (1346), one or more lane maneuvers that correspond to the one or more determined rules are executed, for example in FIG. 4 a rule indicating that when route guidance is indicating to exit, and no vehicles are in adjacent lanes, the AV may maneuver to the right adjacent lane (414).

In one embodiment, automatically navigating further comprises: receiving one or more inputs from the environment for the controlled system; and in response to receiving the one or more inputs, dynamically updating a status of the plurality of subconditions. An example of input may be microwave radar of cars ahead, camera sensor input of lane markers, and/or lidar of objects behind an AV. A status may be whether objects are immediately behind an AV, which may be important for updates when reversing the AV for parallel parking, causing the AV to brake to avoid running over the dynamic object going behind the vehicle.

In one embodiment, representation of a lane subcondition in the plurality of lane subconditions comprises a value having one of a plurality of states, and wherein the plurality of states comprises a state of "don't care", with the other state being "false" or "true". In one embodiment, the value is represented by a single bit. In one embodiment, the value is represented by a single bit and an ANDN hardware instruction is used to match two values in an efficient way to match lane subconditions and produce lane maneuvers. In one embodiment, the value is represented by two bits. One benefit of using one bit is the halving of storage when compared to two bits.

In one embodiment, a first lane in the plurality of lanes is adjacent to a second lane in the plurality of lanes. A lane maneuver in the plurality of lane maneuvers comprises a change between the first lane to the second lane. For example in FIG. 4, the AV (402) changes between the middle lane to a right lane using a lane maneuver (414).

In one embodiment, the environment for the controlled system is a constrained environment comprising a discretized lane-structured environment wherein the controlled system proceeds in a current lane or switches to a lane adjacent to the current lane. The plurality of lane subconditions comprises a route guidance subcondition. For example, in FIG. 5B, this route guidance subcondition provides another column (527) for matching the table. The plurality of lane maneuvers comprises a preemptable lane maneuver, as when a new maneuver may be triggered immediately even though another maneuver is being executed. For example, the maneuver of changing to a passing lane and accelerating may be triggered previously but before this action is completed, a dynamic obstacle is detected that triggers the maneuver to slow down and return to the driving lane.

In one embodiment, a lane in the plurality of lanes is a discretized directional path segment that the controlled system can transit along.

In one embodiment, automatically navigating the controlled system dynamically comprises controlling a behavior (e.g., an operation) of a self-driving physical vehicle. In one embodiment, the plurality of lanes comprises a road lane for driving.

In one embodiment, automatically navigating the controlled system dynamically comprises controlling a behavior of an automatic stock trading platform. In one embodiment, the plurality of lanes comprises a hierarchical lane based at least in part on classification of stocks in different industry segments. For example, in FIG. 3C an initial rule may be: Do not allow the portfolio to have more than X percent of its value in any single stock, represented by lanes (324), (326), (328). A rule for increasing a stock position or selecting the amount to buy may need to avoid having the amount exceed this X percent of the value of the portfolio. However, if the value of one stock goes up significantly or the value of the rest of the portfolio falls significantly, it is possible that this X percent threshold is again exceeded and needs corrective action.

In one embodiment, automatically navigating the controlled system dynamically comprises controlling a behavior of an automatic medical diagnosis and treatment application. In one embodiment, the plurality of lanes comprises a lane representing a medical treatment plan. For example, in FIG. 3D a medical application (352) may currently be in an "aspirin treatment regime" lane (354), with a possible lane maneuver be to switch to a "no treatment regime" (356) before a second lane maneuver into a "fentanyl treatment regime" (360).

In one embodiment, the rule set is received in a different representation, wherein the different representation is at least one of the following: a code realization and a compiled table with a column per observable subcondition and each row associated with a maneuver.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
   inputting specifications comprising:
   a plurality of lanes in an environment for a controlled system;
   a plurality of lane maneuvers associated with the plurality of lanes;
   a plurality of lane subconditions associated with the controlled system; and
   a rule set comprising a plurality of rules, wherein a rule in the rule set specifies a rule condition and a rule action to take when the rule condition is satisfied, wherein the rule condition comprises a corresponding set of lane subconditions, and wherein the rule action comprises a corresponding lane maneuver; and
   automatically navigating the controlled system dynamically, including:
   monitoring the plurality of lane subconditions;
   evaluating rule conditions associated with the plurality of rules in the rule set to determine one or more rules whose corresponding rule conditions has been met; and
   executing one or more lane maneuvers that correspond to the one or more determined rules.

2. The method of claim 1, wherein automatically navigating further comprises:
   receiving one or more inputs from the environment for the controlled system; and
   in response to receiving the one or more inputs, dynamically updating a status of the plurality of subconditions.

3. The method of claim 1, wherein a representation of a lane subcondition in the plurality of lane subconditions comprises a value having one of a plurality of states, and wherein the plurality of states comprises a state of "don't care".

4. The method of claim 3, wherein the value is represented by a single bit.

5. The method of claim 3, wherein the value is represented by a single bit and an ANDN hardware instruction is used to match two values.

6. The method of claim 3, wherein the value is represented by two bits.

7. The method of claim 1, wherein a first lane in the plurality of lanes is adjacent to a second lane in the plurality of lanes.

8. The method of claim 7, wherein a lane maneuver in the plurality of lane maneuvers comprises a change between the first lane to the second lane.

9. The method of claim 1, wherein the environment for the controlled system is a constrained environment comprising a discretized lane-structured environment wherein the controlled system proceeds in a current lane or switches to a lane adjacent to the current lane.

10. The method of claim 1, wherein the plurality of lane subconditions comprises a route guidance subcondition.

11. The method of claim 1, wherein the plurality of lane maneuvers comprises a preemptable lane maneuver.

12. The method of claim 1, wherein a lane in the plurality of lanes is a discretized directional path segment that the controlled system can transit along.

13. The method of claim 1, wherein automatically navigating the controlled system dynamically comprises controlling a behavior of a self-driving physical vehicle.

14. The method of claim 13, wherein the plurality of lanes comprises a road lane for driving.

15. The method of claim 1, further comprising receiving the rule set in a different representation, wherein the different representation is at least one of the following: a compiled table and a code realization.

16. The method of claim 1, wherein specifications further includes one or more additional rule sets.

17. A system, comprising:
   an interface configured to receive specifications comprising:
   a plurality of lanes in an environment for a controlled system;
   a plurality of lane maneuvers associated with the plurality of lanes;
   a plurality of lane subconditions associated with the controlled system; and
   a rule set comprising a plurality of rules, wherein a rule in the rule set specifies a rule condition and a rule action to take when the rule condition is satisfied, wherein the rule condition comprises a corresponding set of lane subconditions, and wherein the rule action comprises a corresponding lane maneuver; and
   a processor coupled to the interface and configured to automatically navigate the controlled system dynamically at least in part by:
   monitoring the plurality of lane subconditions;
   evaluating rule conditions associated with the plurality of rules in the rule set to determine one or more rules whose corresponding rule conditions has been met; and
   executing one or more lane maneuvers that correspond to the one or more determined rules; and
   a memory coupled to the processor and configured to provide the processor with instructions.

18. A computer program product, the computer program product being embodied in a non-transitory computer readable storage medium and comprising computer instructions for:
- inputting specifications comprising:
  - a plurality of lanes in an environment for a controlled system;
  - a plurality of lane maneuvers associated with the plurality of lanes;
  - a plurality of lane subconditions associated with the controlled system; and
  - a rule set comprising a plurality of rules, wherein a rule in the rule set specifies a rule condition and a rule action to take when the rule condition is satisfied, wherein the rule condition comprises a corresponding set of lane subconditions, and wherein the rule action comprises a corresponding lane maneuver; and
- automatically navigating the controlled system dynamically at least in part by:
  - monitoring the plurality of lane subconditions;
  - evaluating rule conditions associated with the plurality of rules in the rule set to determine one or more rules whose corresponding rule conditions has been met; and executing one or more lane maneuvers that correspond to the one or more determined rules.

* * * * *